United States Patent
Mezo et al.

(10) Patent No.: US 8,101,186 B2
(45) Date of Patent: Jan. 24, 2012

(54) PEPTIDES THAT BLOCK THE BINDING OF IGG TO FCRN

(75) Inventors: Adam R. Mezo, Waltham, MA (US); Kevin A. McDonnell, Waltham, MA (US); Cristina A. Tan Hehir, Niskayuna, NY (US); Alfredo Castro, Winchester, MA (US)

(73) Assignee: Syntonix Pharmaceuticals, Inc., Waltham, MA (US)

( * ) Notice: Subject to any disclaimer, the term of this patent is extended or adjusted under 35 U.S.C. 154(b) by 715 days.

(21) Appl. No.: 11/676,148

(22) Filed: Feb. 16, 2007

(65) Prior Publication Data

US 2007/0254831 A1 Nov. 1, 2007

Related U.S. Application Data

(60) Provisional application No. 60/805,634, filed on Jun. 23, 2006, provisional application No. 60/774,853, filed on Feb. 17, 2006.

(51) Int. Cl.
- A61K 39/00 (2006.01)
- A61K 38/08 (2006.01)
- A61K 38/10 (2006.01)
- A61K 38/16 (2006.01)

(52) U.S. Cl. .................. 424/185.1; 514/21.3; 514/21.4; 514/21.5; 514/21.6; 514/21.7; 530/300

(58) Field of Classification Search ........................ None
See application file for complete search history.

(56) References Cited

U.S. PATENT DOCUMENTS

| | | | |
|---|---|---|---|
| 3,941,763 A | 3/1976 | Sarantakis | |
| 4,179,337 A | 12/1979 | Davis et al. | |
| 4,215,051 A | 7/1980 | Schroeder et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,671,958 A | 6/1987 | Rodwell et al. | |
| 4,713,339 A | 12/1987 | Levinson et al. | |
| 4,791,192 A | 12/1988 | Nakagawa et al. | |
| 4,867,973 A | 9/1989 | Goers et al. | |
| 5,252,714 A | 10/1993 | Harris et al. | |
| 5,326,856 A | 7/1994 | Coughlin et al. | |
| 5,449,761 A | 9/1995 | Belinka et al. | |
| 5,623,053 A | 4/1997 | Gastinel et al. | |
| 5,691,154 A | 11/1997 | Callstrom et al. | |
| 5,846,728 A | 12/1998 | Haralambidis et al. | |
| 5,888,512 A | 3/1999 | Clayberger et al. | |
| 5,981,216 A | 11/1999 | Kenten et al. | |
| 6,015,881 A | 1/2000 | Kang et al. | |
| 6,030,613 A | 2/2000 | Blumberg et al. | |
| 6,086,875 A | 7/2000 | Blumberg et al. | |
| 6,121,022 A | 9/2000 | Presta et al. | |
| 6,197,526 B1 | 3/2001 | Yu et al. | |
| 6,212,022 B1 | 4/2001 | Kamikubo | |
| 6,281,331 B1 | 8/2001 | Kang et al. | |
| 6,469,136 B1 | 10/2002 | Bray et al. | |
| 6,472,506 B1 | 10/2002 | Moreau et al. | |
| 6,541,669 B1 | 4/2003 | Moran et al. | |
| 6,685,179 B2 | 2/2004 | Kita | |
| 6,900,292 B2 | 5/2005 | Sun et al. | |
| 6,992,234 B2 | 1/2006 | Roopenian | |
| 7,141,676 B1 | 11/2006 | Wilbur et al. | |
| 7,176,185 B2 | 2/2007 | Hilfinger et al. | |
| 7,232,805 B2 | 6/2007 | Weinshenker et al. | |
| 2002/0138863 A1 | 9/2002 | Roopenian | |
| 2005/0027109 A1 | 2/2005 | Mezo et al. | |
| 2005/0079169 A1 | 4/2005 | Balthasar et al. | |
| 2006/0228348 A1 | 10/2006 | Stefano | |
| 2007/0092507 A1 | 4/2007 | Balthasar et al. | |

FOREIGN PATENT DOCUMENTS

| | | |
|---|---|---|
| EP | 0 154 316 | 9/1985 |
| EP | 0 394 827 | 10/1990 |
| EP | 0 401 384 | 12/1990 |
| WO | WO 92/16221 | 10/1992 |
| WO | WO 95/34326 | 12/1995 |
| WO | WO 02/43658 | 6/2002 |
| WO | WO 2006/000213 | 1/2006 |
| WO | WO 2007/098420 | 8/2007 |
| WO | WO 2009/020867 | 2/2009 |

OTHER PUBLICATIONS

Sanchez et al, Biochemistry 38: 9471-9476, 1999.*
Mezo et al, Bioorganic & Medical Chemistry 16(12):6394-6405; Jun. 2008, Epub May 2008.*
Bain et al., *Tetrahedron* 47(14/15):2389-2400 (1991).
Baldassarre et al., *Theriogenology* 59:831-839 (2003).
Biernat et al., *Bioconjugate Chem.* 17:1116-1124 (2006).
Bodanszky, *Principles of Peptide Synthesis*, 1st ed. Chapter 7 (1984).
Bodanszky, *Principles of Peptide Synthesis*, 2nd revised ed., Chapter 7 (1984).
Boder et al., *Nature Biotechnol.* 15:553-557 (1997).
Brambell et al., *Nature* 203:1352-1355 (1964).
Brinster et al., *Nature* 306:332-336 (1983).
Brinster et al., *Proc. Natl. Acad. Sci. USA* 82:4438-4442 (1985).
Brisson et al., *Nature* 310:511-514 (1984).
Broglie et al., *Science* 224:838-843 (1984).
Burmeister et al., *Nature* 372:336-343 (1994).
Burmeister et al., *Nature* 372:379-383 (1994).
Chamow et al., *Bioconjugate Chem.* 5:133-140 (1994).
Chaudhury et al., *J. Exp. Med.* 197(3):315-322 (2003).
Christianson et al., *J. Immunol.* 159(10):4781-4792 (1997).
Chuang et al., *Pharm. Res.* 19(5):569-577 (2002).
Coruzzi et al., *EMBO J.* 3(8):1671-1679 (1984).
Costagliola et al., *J. Immunol.*, pp. 1458-1465 (1998).
Davis et al., *Biochem. Intl.* 10(3):395-404 (1985).
Dawson et al., *Annu. Rev. Biochem.* 69:923-960 (2000).
Dawson et al., *J. Peptide Sci.* 6:19-25 (2000).
Erickson et al., *The Proteins* (3d ed.) 2:255-527 (1976).
Etzkorn et al., *J. Am. Chem. Soc.* 116:10412-10425 (1994).
Evans et al., *J. Med. Chem.* 30:1229-1239 (1987).
Fauchere, *Adv. Drug Res.* 15:29-69 (1986).

(Continued)

Primary Examiner — Phuong Huynh
(74) *Attorney, Agent, or Firm* — Finnegan, Henderson, Farabow, Garrett & Dunner, LLP

(57) ABSTRACT

The invention relates to peptides which bind to human FcRn and inhibit binding of the Fc portion of an IgG to an FcRn, thereby modulating serum IgG levels. The disclosed compositions and methods may be used for example, in treating autoimmune diseases and inflammatory disorders. The invention also relates to methods of using and methods of making the peptides of the invention.

33 Claims, 24 Drawing Sheets

OTHER PUBLICATIONS

Finn et al., *The Proteins* (3d ed.) 2:105-253 (1976).
Fountoulakis et al., *J. Biol. Chem.* 270(8):3958-3964 (1995).
Francis, *Focus on Growth Factors* 3(2):4-10 (1992).
Freidinger et al., *J. Org. Chem.* 47:104-109 (1982).
Freidinger, *J. Med. Chem.* 46(26):5553-5566 (2003).
Gavilondo et al., *Biotechniques* 29(1):128-145 (2000).
Ghetie et al., *Eur. J. Immunol.* 26:690-696 (1996).
Greene, *Protective Groups in Organic Synthesis*, Ch. 5 Protection for The Carboxyl Group, pp. 152-192 (1991).
Grierson et al., Ch. 7-9, *Plant Molecular Biology*, 2d ed., Blackie, London (1988).
Gurley et al., *Mol. Cell. Biol.* 6(2):559-565 (1986).
Gussow et al., *J. Immunol.* 139(9):3132-3138 (1987).
Hanessian et al., *Tetrahedron* 53(38):12789-12854 (1997).
Hansen et al., *Blood* 100(6):2087-2093 (2002).
Hansen et al., *Thromb. Haemost.* 88:898-899 (2002).
Haslam, Chapter 5, *Protective Groups in Organic Chemistry*, J.G.W. McOmie, Ed., Planum Press, NY (1973).
Houghten et al., *Nature* 354:84-86 (1991).
International Search Report as issued in related International Application No. PCT/US2007/062349, as mailed on Dec. 3, 2007.
Israel et al., *Immunology* 92(1):69-74 (1997).
Israel et al., *J. Immunol.* pp. 6246-6251 (1995).
Johnson et al., *Chem. Biol.* 4(12):939-950 (1997).
Junghans et al., *Proc. Natl. Acad. Sci. USA* 93:5512-5516 (1996).
Junghans, *Immunol. Res.* 16(1):29-57 (1997).
Kelley et al., *Biotechnol. Bioeng.* 87(3):400-412 (2004).
Kim et al., *Diabetes* 52:751-759 (2003).
Kinstler et al., *Adv. Drug Del. Rev.* 54:477-485 (2002).
Knudsen et al., *J. Med. Chem.* 43:1664-1669 (2000).
Kobayashi et al., *Am. J. Renal Physiol.* 282:F358-F365 (2002).
Kolonin et al., *Proc. Natl. Acad. Sci. USA* 99(20):13055-13060 (2002).
Kyte et al., *J. Mol. Biol.* 157:105-132 (1982).
Lam et al., *Nature* 354:82-84 (1991).
Lamb et al., Ch. 2, Commercial Production of Radioisotopes for Nuclear Medicine, *Radiotracers for Medical Applications* vol. 1, Rayudu (Ed.), CRC Press, Inc., Boca Raton, pp. 17-62.
Leach et al., *J. Immunol.* 157:3317-3322 (1996).
Li et al., *J. Clin. Invest.* 115(12):3440-3450 (2005).
Liu et al., *J. Exp. Med.* 186(5):777-783 (1997).
Logan et al., *Proc. Natl. Acad. Sci. USA* 81:3655-3659 (1984).
Mackett et al., *J. Virol.* 49(3):857-864 (1984).
Mackett et al., *Proc. Natl. Acad. Sci. USA* 79:7415-7419 (1982).
Malassagne et al., *Xenotransplantation* 10(3):267-277 (2003).
Malik et al., *Exp. Hematol.* 20:1028-1035 (1992).
Mcknight et al., *Cell* 34:335-341 (1983).
Merrifield, *Chemical Polypeptides*, Katsoyannis and Panayotis eds., Ch. 16, pp. 335-361 (1973).
Merrifield, *J. Am. Chem. Soc.* 85:2149-2154 (1963).
Monaghan et al., ARKIVOC 2001, pp. 46-53 (2001).
Neumann et al., *EMBO J.* 1(7):841-845 (1982).
Panicali et al., *Proc. Natl. Acad. Sci. USA* 79:4927-4931 (1982).
Posnett et al., *J. Biol. Chem.* 263(4):1719-1725 (1988).
Raghavan et al., *Immunity* 1(4):303-315 (1994).
Ritchie et al., *Nature* 312:517-520 (1984).
Rizo et al., *Annu. Rev. Biochem.* 61:387-418 (1992).
Roberts et al., *Proc. Nat. Acad. Sci. USA* 94:12297-12302 (1997).
Robl et al., *Theriogenology* 59:107-113 (2003).
Rogers et al., *Methods for Plant Molecular Biology*, Academic Press NY, Section VIII, pp. 423-463 (1988).
Roopenian et al., *J. Immunol.* 170:3528-3532 (2003).
Rose, *J. Am. Chem. Soc.* 116:30-33 (1994).
Ruther et al., *EMBO J.* 2(10):1791-1794 (1983).
Schlachetzki et al., *J. Neurochem.* 81:203-206 (2002).
Simister et al., *Eur. J. Immunol.* 26:1527-1531 (1996).
Simonsen et al., *Proc. Natl. Acad. Sci. USA* 80:2495-2499 (1983).
Smith et al., *Chem. Rev.* 97:391-410 (1997).
Smith et al., *J. Virol.* 46(2):584-593 (1983).
Story et al., *J. Exp. Med.* 180:2377-2381 (1994).
Subasinghe et al., *J. Med. Chem.* 36:2356-2361 (1993).
Takamatsu et al., *EMBO J.* 6(2):307-311 (1987).
Thornton et al., *Nature* 354:105-106 (1991).
Thumshirn et al., *Chem. Eur. J.* 9:2717-2725 (2003).
Traunecker et al., *Nature* 331:84-86 (1988).
Veber et al., *Trends Neurosci.* 392-396 (1985).
Wagner et al., *Proc. Natl. Acad. Sci. USA* 78(10):6376-6380 (1981).
Wang et al., *J. Am. Chem. Soc.*, 125(11):3192-3193 (2003).
Ward et al., *Int Immunol.* 15(2):187-195 (2002).
Wigler et al., *Cell* 14:725-731 (1978).
Zobel et al., *Bioorg. Med. Chem. Lett.* 13:1513-1515 (2003).
Mezo et al., "Reduction of IgG in nonhuman primates by a peptide antagonist of the neonatal Fc receptor FcRn," *Proc. Natl. Acad. Sci. USA* 105(7):2337-2342 (2008).
U.S. Appl. No. 61/085,547, filed Aug. 1, 2008, Inventors: Adam R. Mezo et al.

\* cited by examiner

FIGURE 1

Human Full length FcRn DNA sequence (ORF) (SEQ ID NO:15)

```
ATGGGGGTCCCGCGGCCTCAGCCCTGGGCGCTGGGGCTCCTGCTCTTTCTCCTTCCTGGGAGCCTGGGCGCAGAAAGCCA
CCTCTCCCTCCTGTACCACCTTACCGCGGTGTCCTCGCCTGCCCCGGGGACTCCTGCCTTCTGGGTGTCCGGCTGGCTGG
GCCCGCAGCAGTACCTGAGCTACAATAGCCTGCGGGGCGAGGCGGAGCCCTGTGGAGCTTGGGTCTGGGAAAAACCAGGTG
TCCTGGTATTGGGAGAAAGAGACCACAGATCTGAGGATCAAGGAGAAGCTCTTTCTGGAAGCTTTCAAAGCTTTGGGGGG
AAAAGGTCCCTACACTCTGCAGGGCCTGCTGGGCTGTGAACTGGGCCCTGACAACACCTCGGTGCCCACCGCCAAGTTCG
CCCTGAACGGCGAGGAGTTCATGAATTTCGACCTCAAGCAGGGCACCTGGGGTGGGGACTGGCCCGAGGCCCTGGCTATC
AGTCAGCGGTGGCAGCAGCAGGACAAGGCGGCCAACAAGGAGCTCACCTTCCTGCTATTCTCCTGCCCGCACCGCCTGCG
GGAGCACCTGGAGAGGGGCCGCGGAAACCTGGAGTGGAAGGAGCCCCCCTCCATGCGCCTGAAGGCCCGACCCAGCAGCC
CTGGCTTTTCCGTGCTTACCTGCAGCGCCTTCTCCTTCTACCCTCCGGAGCTGCAACTTCGGTTCCTGCGGAATGGGCTG
GCCGCTGGCACCGGCCAGGGTGACTTCGGCCCCAACAGTGACGGATCCTTCCACGCCTCGTCGTCACTAACAGTCAAAAG
TGGCGATGAGCACCACTACTGCTGCATTGTGCAGCACGCGGGGCTGGCGCAGCCCCTCAGGGTGGAGCTGGAATCTCCAG
CCAAGTCCTCCGTGCTCGTGGTGGGAATCGTCATCGGTGTCTTGCTACTCACGGCAGCGGCTGTAGGAGGAGCTCTGTTG
TGGAGAAGGATGAGGAGTGGGCTGCCAGCCCCTTGGATCTCCCTTCGTGGAGACGACACCGGGGTCCTCCTGCCCACCCC
AGGGGAGGCCCAGGATGCTGATTTGAAGGATGTAAATGTGATTCCAGCCACCGCCTGA
```

Human β-2M DNA sequence (ORF) (SEQ ID NO:16)

```
ATGTCTCGCTCCGTGGCCTTAGCTGTGCTCGCGCTACTCTCTCTTTCTGGCCTGGAGGCTATCCAGCGTACTCCAAAGAT
TCAGGTTTACTCACGTCATCCAGCAGAGAATGGAAAGTCAAATTTCCTGAATTGCTATGTGTCTGGGTTTCATCCATCCG
ACATTGAAGTTGACTTACTGAAGAATGGAGAGAGAATTGAAAAAGTGGAGCATTCAGACTTGTCTTTCAGCAAGGACTGG
TCTTTCTATCTCTTGTACTACACTGAATTCACCCCCACTGAAAAAGATGAGTATGCCTGCCGTGTGAACCATGTGACTTT
GTCACAGCCCAAGATAGTTAAGTGGGATCGAGACATGTAA
```

NH2-RF-Pen-TGHFG-Sar-NMeLeu-YPC-rink resin    (protected peptide)

1. Succinic anhydride, DIEA/DMF
2. 2,2-dimethyl-1,3-dioxolane-4-methamine (Aldrich Cat #: 483117)
   PyBOP/ DIEA in DMF
3. TFA/TIS resin cleavage
4. $I_2$ oxidation (AcOH/$H_2O$)
5. HPLC Purify (C18 column)

N-terminal diol

1. NaIO$_4$
   AcOH / H$_2$O
2. Sep/Pak C18

N-terminal aldehyde containing peptide monomer

N-terminal sarcosine containing peptide monomer

N-terminal aldehyde containing peptide monomer

Peptide No. 270

Peptide No. 100

Peptide No. 122

Peptide No. 283

Peptide No. 280

Peptide No. 252

```
                       SEQUENCE LISTING

<160> NUMBER OF SEQ ID NOS: 322

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Arg Phe Cys Thr Gly His Phe Gly Gly Leu Tyr Pro Cys Asn Gly
1               5                   10                  15

Pro

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Cys Val Thr Gly His Phe Gly Gly Ile Tyr Cys Asn Tyr
1               5                   10                  15

Gln

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ile Ile Cys Ser Pro Gly His Phe Gly Gly Met Tyr Cys Gln Gly
1               5                   10                  15

Lys

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Ser Tyr Cys Ile Glu Gly His Ile Asp Gly Ile Tyr Cys Phe Asn
1               5                   10                  15

Ala
```

```
<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Ser Phe Cys Arg Gly Arg Pro Gly His Phe Gly Gly Cys Tyr Leu
1               5                   10                  15

Phe

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Gly Gln Arg Phe Cys Thr Gly His Phe Gly Gly Leu Tyr Pro Cys
1               5                   10                  15

Asn Gly Pro Gly Thr Gly Gly Gly Lys
            20                  25

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Gly Gly Gly Cys Val Thr Gly His Phe Gly Gly Ile Tyr Cys Asn
1               5                   10                  15

Thr Gln Gly Thr Gly Gly Gly Lys
            20

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gly Lys Ile Ile Cys Ser Pro Gly His Phe Gly Gly Met Tyr Cys
1               5                   10                  15

Gln Gly Lys Gly Thr Gly Gly Gly Lys
            20                  25

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Gly Pro Ser Tyr Cys Ile Glu Gly His Ile Asp Gly Ile Tyr Cys
1               5                   10                  15
```

```
Phe Asn Ala Gly Thr Gly Gly Gly Lys
        20                  25

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Gly Asn Ser Phe Cys Arg Gly Arg Pro Gly His Phe Gly Gly Cys
1               5                   10                  15

Tyr Leu Phe Gly Thr Gly Gly Gly Lys
            20                  25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cggcgcaact atcggtatca agctg                                           25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catgtaccgt aacactgagt ttcgtc                                          26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gataaaccga tacaattaaa ggctcc                                          26

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Variable amino acid

<400> SEQUENCE: 14

Gly His Phe Gly Gly Xaa Tyr
1               5

<210> SEQ ID NO 15
```

<211> LENGTH: 1098
<212> TYPE: DNA
<213> ORGANISM: Homo sapiens
<400> SEQUENCE: 15

| | | | | | |
|---|---|---|---|---|---|
| atggggtcc | cgcggcctca | gccctgggcg | ctggggctcc | tgctctttct | ccttcctggg | 60 |
| agcctgggcg | cagaaagcca | cctctccctc | ctgtaccacc | ttaccgcggt | gtcctcgcct | 120 |
| gccccgggga | ctcctgcctt | ctgggtgtcc | ggctggctgg | gcccgcagca | gtacctgagc | 180 |
| tacaatagcc | tgcggggcga | ggcggagccc | tgtggagctt | gggtctggga | aaaccaggtg | 240 |
| tcctggtatt | gggagaaaga | gaccacagat | ctgaggatca | aggagaagct | ctttctggaa | 300 |
| gctttcaaag | ctttgggggg | aaaaggtccc | tacactctgc | agggcctgct | gggctgtgaa | 360 |
| ctgggccctg | acaacacctc | ggtgcccacc | gccaagttcg | ccctgaacgg | cgaggagttc | 420 |
| atgaatttcg | acctcaagca | gggcacctgg | ggtggggact | ggcccgaggc | cctggctatc | 480 |
| agtcagcggt | ggcagcagca | ggacaaggcg | ccaacaagg | agctcacctt | cctgctattc | 540 |
| tcctgcccgc | accgctgcg | ggagcacctg | gagaggggcc | gcggaaacct | ggagtggaag | 600 |
| gagcccccct | ccatgcgcct | gaaggccga | cccagcagcc | ctggcttttc | cgtgcttacc | 660 |
| tgcagcgcct | tctccttcta | ccctccggag | ctgcaacttc | ggttcctgcg | gaatgggctg | 720 |
| gccgctggca | ccggccaggg | tgacttcggc | cccaacagtg | acggatcctt | ccacgcctcg | 780 |
| tcgtcactaa | cagtcaaaag | tggcgatgag | caccactact | gctgcattgt | gcagcacgcg | 840 |
| gggctggcgc | agcccctcag | ggtggagctg | aatctccag | ccaagtcctc | cgtgctcgtg | 900 |
| gtgggaatcg | tcatcggtgt | cttgctactc | acggcagcgg | ctgtaggagg | agctctgttg | 960 |
| tggagaagga | tgaggagtgg | gctgccagcc | ccttggatct | cccttcgtgg | agacgacacc | 1020 |
| ggggtcctcc | tgcccacccc | agggaggcc | caggatgctg | atttgaagga | tgtaaatgtg | 1080 |
| attccagcca | ccgcctga | | | | | 1098 |

<210> SEQ ID NO 16
<211> LENGTH: 360
<212> TYPE: DNA
<213> ORGANISM: Homo sapiens
<400> SEQUENCE: 16

| | | | | | |
|---|---|---|---|---|---|
| atgtctcgct | ccgtggcctt | agctgtgctc | gcgctactct | ctctttctgg | cctggaggct | 60 |
| atccagcgta | ctccaaagat | tcaggtttac | tcacgtcatc | cagcagagaa | tggaaagtca | 120 |
| aatttcctga | attgctatgt | gtctgggttt | catccatccg | acattgaagt | tgacttactg | 180 |
| aagaatggag | agagaattga | aaaagtggag | cattcagact | tgtctttcag | caaggactgg | 240 |
| tctttctatc | tcttgtacta | cactgaattc | accccccactg | aaaaagatga | gtatgcctgc | 300 |
| cgtgtgaacc | atgtgacttt | gtcacagccc | aagatagtta | agtgggatcg | agacatgtaa | 360 |

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 17

Cys Thr Gly His Phe Gly Gly Leu Tyr Pro Cys Asn Gly Pro
1               5                   10

<210> SEQ ID NO 18

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Arg Phe Cys Thr Gly His Phe Gly Gly Leu Tyr Pro Cys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Thr Gly His Phe Gly Gly Leu Tyr Pro Cys
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Gly His Phe Gly Gly Leu Tyr Pro
1               5

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Phe Cys Thr Gly His Phe Gly Gly Leu Tyr Pro Cys Asn Gly Pro
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Cys Thr Gly His Phe Gly Gly Leu Tyr Pro Cys Asn Gly Pro
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Arg Phe Cys Thr Gly His Phe Gly Gly Leu Tyr Pro Cys Asn Gly
```

```
                1               5                  10                 15
```

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Gln Arg Phe Cys Thr Gly His Phe Gly Gly Leu Tyr Pro Cys Asn
1               5                  10                 15
```

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Gln Ala Phe Cys Thr Gly His Phe Gly Gly Leu Tyr Pro Cys Asn Gly
1               5                  10                 15

Pro
```

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Gln Arg Ala Cys Thr Gly His Phe Gly Gly Leu Tyr Pro Cys Asn Gly
1               5                  10                 15

Pro
```

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gln Arg Phe Cys Ala Gly His Phe Gly Gly Leu Tyr Pro Cys Asn Gly
1               5                  10                 15

Pro
```

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Gln Arg Phe Cys Thr Ala His Phe Gly Gly Leu Tyr Pro Cys Asn Gly
1               5                  10                 15

Pro
```

```
<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Arg Phe Cys Thr Gly Ala Phe Gly Gly Leu Tyr Pro Cys Asn Gly
1               5                   10                  15

Pro

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Arg Phe Cys Thr Gly His Ala Gly Gly Leu Tyr Pro Cys Asn Gly
1               5                   10                  15

Pro

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Arg Phe Cys Thr Gly His Phe Ala Gly Leu Tyr Pro Cys Asn Gly
1               5                   10                  15

Pro

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Arg Phe Cys Thr Gly His Phe Gly Ala Leu Tyr Pro Cys Asn Gly
1               5                   10                  15

Pro

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Arg Phe Cys Thr Gly His Phe Gly Gly Ala Tyr Pro Cys Asn Gly
1               5                   10                  15

Pro
```

```
<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Arg Phe Cys Thr Gly His Phe Gly Gly Leu Ala Pro Cys Asn Gly
1               5                   10                  15

Pro

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Arg Phe Cys Thr Gly His Phe Gly Gly Leu Tyr Ala Cys Asn Gly
1               5                   10                  15

Pro

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Arg Phe Cys Thr Gly His Phe Gly Gly Leu Tyr Pro Cys Ala Gly
1               5                   10                  15

Pro

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: homocysteine

<400> SEQUENCE: 37

Gln Arg Phe Cys Thr Gly His Phe Gly Gly Leu Tyr Pro Xaa Asn Gly
1               5                   10                  15

Pro

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: homocysteine
```

```
<220> FEATURE:
<221> NAME/KEY: MOD_RES
<222> LOCATION: (14)..(14)
<223> OTHER INFORMATION: homocysteine

<400> SEQUENCE: 38

Gln Arg Phe Xaa Thr Gly His Phe Gly Gly Leu Tyr Pro Xaa Asn Gly
1               5                   10                  15

Pro

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Cys

<400> SEQUENCE: 39

Gln Arg Phe Xaa Thr Gly His Phe Gly Gly Leu Tyr Pro Cys Asn Gly
1               5                   10                  15

Pro

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: D-Cys

<400> SEQUENCE: 40

Gln Arg Phe Cys Thr Gly His Phe Gly Gly Leu Tyr Pro Xaa Asn Gly
1               5                   10                  15

Pro

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Cys
<220> FEATURE:
<221> NAME/KEY: MOD_RES
<222> LOCATION: (14)..(14)
<223> OTHER INFORMATION: D-Cys

<400> SEQUENCE: 41

Gln Arg Phe Xaa Thr Gly His Phe Gly Gly Leu Tyr Pro Xaa Asn Gly
1               5                   10                  15

Pro

<210> SEQ ID NO 42
<211> LENGTH: 17
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 42

Gln Arg Phe Xaa Thr Gly His Phe Gly Gly Leu Tyr Pro Cys Asn Gly
1               5                   10                  15

Pro

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Pen

<400> SEQUENCE: 43

Gln Arg Phe Cys Thr Gly His Phe Gly Gly Leu Tyr Pro Xaa Asn Gly
1               5                   10                  15

Pro

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (14)..(14)
<223> OTHER INFORMATION: Pen

<400> SEQUENCE: 44

Gln Arg Phe Xaa Thr Gly His Phe Gly Gly Leu Tyr Pro Xaa Asn Gly
1               5                   10                  15

Pro

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (14)..(14)
<223> OTHER INFORMATION: homocysteine

<400> SEQUENCE: 45

Gln Arg Phe Xaa Thr Gly His Phe Gly Gly Leu Tyr Pro Xaa Asn Gly
```

```
1               5                  10                  15
Pro

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: homocysteine
<220> FEATURE:
<221> NAME/KEY: MOD_RES
<222> LOCATION: (14)..(14)
<223> OTHER INFORMATION: Pen

<400> SEQUENCE: 46

Gln Arg Phe Xaa Thr Gly His Phe Gly Gly Leu Tyr Pro Xaa Asn Gly
1               5                  10                  15
Pro

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Pro
<220> FEATURE:
<221> NAME/KEY: MOD_RES
<222> LOCATION: (14)..(14)
<223> OTHER INFORMATION: Pen

<400> SEQUENCE: 47

Gln Arg Phe Xaa Thr Gly His Phe Gly Xaa Leu Tyr Pro Xaa Asn Gly
1               5                  10                  15
Pro

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeAla

<400> SEQUENCE: 48

Gln Arg Phe Cys Xaa Gly His Phe Gly Gly Leu Tyr Pro Cys Asn Gly
1               5                  10                  15
Pro

<210> SEQ ID NO 49
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 49

Gln Arg Phe Xaa Thr Gly His Phe Gly Gly Leu Tyr Pro Cys Asn Gly
1               5                   10                  15

Pro

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (6)..(6)
<223> OTHER INFORMATION: Sar

<400> SEQUENCE: 50

Gln Arg Phe Xaa Thr Xaa His Phe Gly Gly Leu Tyr Pro Cys Asn Gly
1               5                   10                  15

Pro

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: NMeHis

<400> SEQUENCE: 51

Arg Phe Xaa Thr Gly Xaa Phe Gly Gly Leu Tyr Pro Cys
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: NMePhe

<400> SEQUENCE: 52
```

```
Gln Arg Phe Xaa Thr Gly His Xaa Gly Gly Leu Tyr Pro Cys Asn Gly
1               5                   10                  15

Pro

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: Sar

<400> SEQUENCE: 53

Gln Arg Phe Xaa Thr Gly His Phe Xaa Gly Leu Tyr Pro Cys Asn Gly
1               5                   10                  15

Pro

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: Sar

<400> SEQUENCE: 54

Gln Arg Phe Xaa Thr Gly His Phe Gly Xaa Leu Tyr Pro Cys Asn Gly
1               5                   10                  15

Pro

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (11)..(11)
<223> OTHER INFORMATION: NMeLeu

<400> SEQUENCE: 55

Gln Arg Phe Xaa Thr Gly His Phe Gly Gly Xaa Tyr Pro Cys Asn Gly
1               5                   10                  15

Pro

<210> SEQ ID NO 56
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: NMeTyr

<400> SEQUENCE: 56

Gln Arg Phe Xaa Thr Gly His Phe Gly Gly Leu Xaa Pro Cys Asn Gly
1               5                   10                  15

Pro

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (10)..(10)
<223> OTHER INFORMATION: NMeLeu

<400> SEQUENCE: 57

Arg Phe Xaa Thr Gly His Phe Gly Gly Xaa Tyr Pro Cys Asn Gly Pro
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar

<400> SEQUENCE: 58

Arg Phe Xaa Thr Gly His Phe Gly Xaa Tyr Pro Cys Asn Gly Pro
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
```

```
<222> LOCATION: (10)..(10)
<223> OTHER INFORMATION: Sar
<220> FEATURE:
<221> NAME/KEY: MOD_RES
<222> LOCATION: (11)..(11)
<223> OTHER INFORMATION: NMeLeu

<400> SEQUENCE: 59

Gln Arg Phe Xaa Thr Gly His Phe Gly Xaa Xaa Tyr Pro Cys Asn Gly
1               5                   10                  15

Pro

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 60

Arg Phe Xaa Thr Gly His Phe Gly Xaa Xaa Tyr Pro Cys
1               5                   10

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 61

Gln Arg Phe Xaa Thr Gly His Phe Gly Gly Leu Tyr Pro Cys Asn Gly
1               5                   10                  15

Pro

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pen

<400> SEQUENCE: 62

Phe Xaa Thr Gly His Phe Gly Gly Leu Tyr Pro Cys
1               5                   10

<210> SEQ ID NO 63
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pen

<400> SEQUENCE: 63

Phe Xaa Thr Gly His Phe Gly Gly Leu Tyr Pro Cys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen

<400> SEQUENCE: 64

Arg Phe Xaa Thr Gly His Phe Gly Gly Leu Tyr Pro Cys
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Pro

<400> SEQUENCE: 65

Gln Arg Phe Xaa Thr Gly His Phe Gly Xaa Leu Tyr Pro Cys
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: D-Pro

<400> SEQUENCE: 66

Arg Phe Xaa Thr Gly His Phe Gly Xaa Leu Tyr Pro Cys
1               5                   10

<210> SEQ ID NO 67
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (8)..(8)
<223> OTHER INFORMATION: D-Pro

<400> SEQUENCE: 67

Phe Xaa Thr Gly His Phe Gly Xaa Leu Tyr Pro Cys
1               5                   10

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: D-Pro

<400> SEQUENCE: 68

Arg Phe Xaa Thr Gly His Phe Gly Xaa Leu Tyr Pro Cys Asn Gly Pro
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (8)..(8)
<223> OTHER INFORMATION: D-Pro

<400> SEQUENCE: 69

Phe Xaa Thr Gly His Phe Gly Xaa Leu Tyr Pro Cys Asn Gly Pro
1               5                   10                  15

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 70

Gln Arg Phe Xaa Thr Gly His Phe Gly Gly Leu Tyr Pro Cys Asn Gly
```

```
1               5                   10                  15
Pro

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Pro

<400> SEQUENCE: 71

Gln Arg Phe Xaa Thr Gly His Phe Gly Xaa Leu Tyr Pro Cys Asn Gly
1               5                   10                  15
Pro

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Arg

<400> SEQUENCE: 72

Gln Arg Phe Xaa Thr Gly His Phe Gly Xaa Leu Tyr Pro Cys Asn Gly
1               5                   10                  15
Pro

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-His

<400> SEQUENCE: 73

Gln Arg Phe Xaa Thr Gly His Phe Gly Xaa Leu Tyr Pro Cys Asn Gly
1               5                   10                  15
Pro

<210> SEQ ID NO 74
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Ile

<400> SEQUENCE: 74

Gln Arg Phe Xaa Thr Gly His Phe Gly Xaa Leu Tyr Pro Cys Asn Gly
1               5                   10                  15

Pro

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Phe

<400> SEQUENCE: 75

Gln Arg Phe Xaa Thr Gly His Phe Gly Xaa Leu Tyr Pro Cys Asn Gly
1               5                   10                  15

Pro

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Tyr

<400> SEQUENCE: 76

Gln Arg Phe Xaa Thr Gly His Phe Gly Xaa Leu Tyr Pro Cys Asn Gly
1               5                   10                  15

Pro

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
```

```
<220> FEATURE:
<221> NAME/KEY: MOD_RES
<222> LOCATION: (10)..(10)
<223> OTHER INFORMATION: Aib

<400> SEQUENCE: 77

Gln Arg Phe Xaa Thr Gly His Phe Gly Xaa Leu Tyr Pro Cys Asn Gly
1               5                   10                  15

Pro

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Asp

<400> SEQUENCE: 78

Gln Arg Phe Xaa Thr Gly His Phe Xaa Gly Leu Tyr Pro Cys Asn Gly
1               5                   10                  15

Pro

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Pro

<400> SEQUENCE: 79

Gln Arg Phe Xaa Thr Gly His Phe Xaa Gly Leu Tyr Pro Cys Asn Gly
1               5                   10                  15

Pro

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Arg

<400> SEQUENCE: 80

Gln Arg Phe Xaa Thr Gly His Phe Xaa Gly Leu Tyr Pro Cys Asn Gly
```

```
                  1               5                  10                  15
Pro

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-His

<400> SEQUENCE: 81

Gln Arg Phe Xaa Thr Gly His Phe Xaa Gly Leu Tyr Pro Cys Asn Gly
  1               5                  10                  15
Pro

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ile

<400> SEQUENCE: 82

Gln Arg Phe Xaa Thr Gly His Phe Xaa Gly Leu Tyr Pro Cys Asn Gly
  1               5                  10                  15
Pro

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe

<400> SEQUENCE: 83

Gln Arg Phe Xaa Thr Gly His Phe Xaa Gly Leu Tyr Pro Cys Asn Gly
  1               5                  10                  15
Pro

<210> SEQ ID NO 84
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Tyr

<400> SEQUENCE: 84

Gln Arg Phe Xaa Thr Gly His Phe Xaa Gly Leu Tyr Pro Cys Asn Gly
1               5                   10                  15

Pro

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: Aib

<400> SEQUENCE: 85

Gln Arg Phe Xaa Thr Gly His Phe Xaa Gly Leu Tyr Pro Cys Asn Gly
1               5                   10                  15

Pro

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Ala

<400> SEQUENCE: 86

Gln Arg Phe Xaa Thr Gly His Phe Gly Xaa Leu Tyr Pro Cys Asn Gly
1               5                   10                  15

Pro

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
```

```
<220> FEATURE:
<221> NAME/KEY: MOD_RES
<222> LOCATION: (9)..(9)
<223> OTHER INFORMATION: D-Ala

<400> SEQUENCE: 87

Gln Arg Phe Xaa Thr Gly His Phe Xaa Gly Leu Tyr Pro Cys Asn Gly
1               5                   10                  15

Pro

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(10)
<223> OTHER INFORMATION: D-Ala

<400> SEQUENCE: 88

Gln Arg Phe Xaa Thr Gly His Phe Xaa Xaa Leu Tyr Pro Cys Asn Gly
1               5                   10                  15

Pro

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (10)..(10)
<223> OTHER INFORMATION: D-Pro

<400> SEQUENCE: 89

Gln Arg Phe Xaa Thr Gly His Phe Xaa Xaa Leu Tyr Pro Cys Asn Gly
1               5                   10                  15

Pro

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe
```

```
<220> FEATURE:
<221> NAME/KEY: MOD_RES
<222> LOCATION: (10)..(10)
<223> OTHER INFORMATION: D-Pro

<400> SEQUENCE: 90

Gln Arg Phe Xaa Thr Gly His Phe Xaa Xaa Leu Tyr Pro Cys Asn Gly
1               5                   10                  15

Pro

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe
<220> FEATURE:
<221> NAME/KEY: MOD_RES
<222> LOCATION: (10)..(10)
<223> OTHER INFORMATION: D-Ala

<400> SEQUENCE: 91

Gln Arg Phe Xaa Thr Gly His Phe Xaa Xaa Leu Tyr Pro Cys Asn Gly
1               5                   10                  15

Pro

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(10)
<223> OTHER INFORMATION: D-Pro

<400> SEQUENCE: 92

Gln Arg Phe Xaa Thr Gly His Phe Xaa Xaa Leu Tyr Pro Cys Asn Gly
1               5                   10                  15

Pro

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe
```

```
<220> FEATURE:
<221> NAME/KEY: MOD_RES
<222> LOCATION: (11)..(11)
<223> OTHER INFORMATION: NMeLeu

<400> SEQUENCE: 93

Gln Arg Phe Xaa Thr Gly His Phe Xaa Gly Xaa Tyr Pro Cys Asn Gly
1               5                  10                  15

Pro

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (11)..(11)
<223> OTHER INFORMATION: NMeLeu

<400> SEQUENCE: 94

Gln Arg Phe Xaa Thr Gly His Phe Xaa Gly Xaa Tyr Pro Cys Asn Gly
1               5                  10                  15

Pro

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe

<400> SEQUENCE: 95

Gln Arg Phe Xaa Thr Gly His Phe Xaa Gly Pro Tyr Pro Cys Asn Gly
1               5                  10                  15

Pro

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Pro
```

<400> SEQUENCE: 96

Gln Arg Phe Xaa Thr Gly His Phe Xaa Pro Leu Tyr Pro Cys Asn Gly
1               5                   10                  15

Pro

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe

<400> SEQUENCE: 97

Gln Arg Phe Xaa Thr Gly His Phe Xaa Pro Leu Tyr Pro Cys Asn Gly
1               5                   10                  15

Pro

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (10)..(10)
<223> OTHER INFORMATION: Sar

<400> SEQUENCE: 98

Gln Arg Phe Xaa Thr Gly His Phe Xaa Xaa Leu Tyr Pro Cys Asn Gly
1               5                   10                  15

Pro

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 99

Gln Arg Phe Xaa Thr Gly His Phe Gly Gly Leu Tyr Pro Cys Asn Gly
1               5                   10                  15

Pro

```
<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MOD_RES
<222> LOCATION: (4)..(4)
<223> OTHER INFORMATION: Pen

<400> SEQUENCE: 100

Gln Arg Xaa Xaa Thr Gly His Phe Gly Gly Leu Tyr Pro Cys Asn Gly
1               5                   10                  15

Pro

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 101

Gln Arg Tyr Xaa Thr Gly His Phe Gly Gly Leu Tyr Pro Cys Asn Gly
1               5                   10                  15

Pro

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 102

Gln Arg Trp Xaa Thr Gly His Phe Gly Gly Leu Tyr Pro Cys Asn Gly
1               5                   10                  15

Pro

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 103

Gln Arg Phe Xaa Thr Gly His Phe Gly Gly Leu Tyr Pro Cys Asn Gly
```

```
<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 104

Gln Arg Phe Xaa His Gly His Phe Gly Gly Leu Tyr Pro Cys Asn Gly
1               5                   10                  15

Pro

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 105

Gln Arg Phe Xaa Gly Gly His Phe Gly Gly Leu Tyr Pro Cys Asn Gly
1               5                   10                  15

Pro

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (5)..(5)
<223> OTHER INFORMATION: NMeAla

<400> SEQUENCE: 106

Gln Arg Phe Xaa Xaa Gly His Phe Gly Gly Leu Tyr Pro Cys Asn Gly
1               5                   10                  15

Pro

<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
```

```
<220> FEATURE:
<221> NAME/KEY: MOD_RES
<222> LOCATION: (10)..(10)
<223> OTHER INFORMATION: Sar
<220> FEATURE:
<221> NAME/KEY: MOD_RES
<222> LOCATION: (11)..(11)
<223> OTHER INFORMATION: NMeLeu

<400> SEQUENCE: 107

Gln Arg Phe Xaa Thr Gly His Phe Gly Xaa Xaa Tyr Pro Cys Asn Gly
1               5                   10                  15

Pro

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (10)..(10)
<223> OTHER INFORMATION: Sar
<220> FEATURE:
<221> NAME/KEY: MOD_RES
<222> LOCATION: (11)..(11)
<223> OTHER INFORMATION: NMeLeu

<400> SEQUENCE: 108

Gln Arg Phe Xaa Thr Gly His Phe Xaa Xaa Xaa Tyr Pro Cys Asn Gly
1               5                   10                  15

Pro

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 109

Arg Phe Xaa Thr Gly His Phe Gly Xaa Xaa Tyr Pro Cys
1               5                   10

<210> SEQ ID NO 110
<211> LENGTH: 13
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 110

Arg Phe Xaa Thr Gly His Phe Xaa Xaa Xaa Tyr Pro Cys
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Val
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 111

Arg Phe Xaa Thr Gly His Phe Xaa Xaa Xaa Tyr Pro Cys
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Leu
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 112
```

Arg Phe Xaa Thr Gly His Phe Xaa Xaa Xaa Tyr Pro Cys
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Trp
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 113

Arg Phe Xaa Thr Gly His Phe Xaa Xaa Xaa Tyr Pro Cys
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Thr
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 114

Arg Phe Xaa Thr Gly His Phe Xaa Xaa Xaa Tyr Pro Cys
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Ser

```
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 115

Arg Phe Xaa Thr Gly His Phe Xaa Xaa Xaa Tyr Pro Cys
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Asp
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 116

Arg Phe Xaa Thr Gly His Phe Xaa Xaa Xaa Tyr Pro Cys
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Asn
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 117

Arg Phe Xaa Thr Gly His Phe Xaa Xaa Xaa Tyr Pro Cys
1               5                   10

<210> SEQ ID NO 118
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 118

Arg Phe Xaa Thr Gly His Phe Xaa Xaa Xaa Tyr Pro Cys
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Gln
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 119

Arg Phe Xaa Thr Gly His Phe Xaa Xaa Xaa Tyr Pro Cys
1               5                   10

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 120

Gln Arg Phe Xaa Thr Gly His Phe Gly Gly Leu Tyr Pro Cys Asn Gly
1               5                   10                  15

Pro

<210> SEQ ID NO 121
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 4-amino-Phe

<400> SEQUENCE: 121

Gln Arg Phe Xaa Thr Gly His Xaa Gly Gly Leu Tyr Pro Cys Asn Gly
1               5                   10                  15

Pro

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 4-methoxy-Phe

<400> SEQUENCE: 122

Gln Arg Phe Xaa Thr Gly His Xaa Gly Gly Leu Tyr Pro Cys Asn Gly
1               5                   10                  15

Pro

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: pentafluoro-Phe

<400> SEQUENCE: 123

Gln Arg Phe Xaa Thr Gly His Xaa Gly Gly Leu Tyr Pro Cys Asn Gly
1               5                   10                  15

Pro

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
```

```
<222> LOCATION: (8)..(8)
<223> OTHER INFORMATION: 2-pyridylalanine

<400> SEQUENCE: 124

Gln Arg Phe Xaa Thr Gly His Xaa Gly Gly Leu Tyr Pro Cys Asn Gly
1               5                   10                  15

Pro

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 3-pyridylAla

<400> SEQUENCE: 125

Gln Arg Phe Xaa Thr Gly His Xaa Gly Gly Leu Tyr Pro Cys Asn Gly
1               5                   10                  15

Pro

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 4-nitro-Phe

<400> SEQUENCE: 126

Gln Arg Phe Xaa Thr Gly His Xaa Gly Gly Leu Tyr Pro Cys Asn Gly
1               5                   10                  15

Pro

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 1-napthylalanine

<400> SEQUENCE: 127

Gln Arg Phe Xaa Thr Gly His Xaa Gly Gly Leu Tyr Pro Cys Asn Gly
1               5                   10                  15
```

-continued

Pro

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 2-napthylalanine

<400> SEQUENCE: 128

Gln Arg Phe Xaa Thr Gly His Xaa Gly Gly Leu Tyr Pro Cys Asn Gly
1               5                   10                  15

Pro

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 2-MePhe

<400> SEQUENCE: 129

Gln Arg Phe Xaa Thr Gly His Xaa Gly Gly Leu Tyr Pro Cys Asn Gly
1               5                   10                  15

Pro

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 3-MePhe

<400> SEQUENCE: 130

Gln Arg Phe Xaa Thr Gly His Xaa Gly Gly Leu Tyr Pro Cys Asn Gly
1               5                   10                  15

Pro

<210> SEQ ID NO 131
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 4-MePhe

<400> SEQUENCE: 131

Gln Arg Phe Xaa Thr Gly His Xaa Gly Gly Leu Tyr Pro Cys Asn Gly
1               5                   10                  15

Pro

<210> SEQ ID NO 132
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: homoPhe

<400> SEQUENCE: 132

Gln Arg Phe Xaa Thr Gly His Xaa Gly Gly Leu Tyr Pro Cys Asn Gly
1               5                   10                  15

Pro

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: Cha

<400> SEQUENCE: 133

Gln Arg Phe Xaa Thr Gly His Xaa Gly Gly Leu Tyr Pro Cys Asn Gly
1               5                   10                  15

Pro

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES

```
<222> LOCATION: (8)..(8)
<223> OTHER INFORMATION: PheNHAc

<400> SEQUENCE: 134

Gln Arg Phe Xaa Thr Gly His Xaa Gly Gly Leu Tyr Pro Cys Asn Gly
1               5                   10                  15

Pro

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 135

Gln Arg Phe Xaa Thr Gly His Trp Gly Gly Leu Tyr Pro Cys Asn Gly
1               5                   10                  15

Pro

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: phenylGly

<400> SEQUENCE: 136

Gln Arg Phe Xaa Thr Gly His Xaa Gly Gly Leu Tyr Pro Cys Asn Gly
1               5                   10                  15

Pro

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: Tic

<400> SEQUENCE: 137

Gln Arg Phe Xaa Thr Gly His Xaa Gly Gly Leu Tyr Pro Cys Asn Gly
1               5                   10                  15

Pro

<210> SEQ ID NO 138
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 2MePhe

<400> SEQUENCE: 138

Gln Arg Phe Asp Thr Gly His Xaa Gly Gly Leu Tyr Pro Lys Asn Gly
1               5                   10                  15

Pro

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 2-Cl-Phe

<400> SEQUENCE: 139

Arg Phe Xaa Thr Gly His Xaa Gly Gly Leu Tyr Pro Cys
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 3-Cl-Phe

<400> SEQUENCE: 140

Arg Phe Xaa Thr Gly His Xaa Gly Gly Leu Tyr Pro Cys
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 4-Cl-Phe

<400> SEQUENCE: 141
```

Arg Phe Xaa Thr Gly His Xaa Gly Gly Leu Tyr Pro Cys
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 3,3-Di-Phe

<400> SEQUENCE: 142

Arg Phe Xaa Thr Gly His Xaa Gly Gly Leu Tyr Pro Cys
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 4,4-Bi-Phe

<400> SEQUENCE: 143

Arg Phe Xaa Thr Gly His Xaa Gly Gly Leu Tyr Pro Cys
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 4-t-butyl-Phe

<400> SEQUENCE: 144

Arg Phe Xaa Thr Gly His Xaa Gly Gly Leu Tyr Pro Cys
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: betamethylPhe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 145

Arg Phe Xaa Thr Gly His Xaa Gly Xaa Xaa Tyr Pro Cys
1               5                   10

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Arg Phe Cys Thr Gly His Phe Gly Gly Leu Phe Pro Cys Asn Gly
1               5                   10                  15

Pro

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 147

Gln Arg Phe Xaa Thr Gly His Phe Gly Gly Leu Tyr Pro Cys Asn Gly
1               5                   10                  15

Pro

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 4-amino-Phe

<400> SEQUENCE: 148

Gln Arg Phe Xaa Thr Gly His Phe Gly Gly Leu Xaa Pro Cys Asn Gly
1               5                   10                  15

Pro
```

```
<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 4-methoxyPhe

<400> SEQUENCE: 149

Gln Arg Phe Xaa Thr Gly His Phe Gly Gly Leu Xaa Pro Cys Asn Gly
1               5                   10                  15

Pro

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: pentafluoroPhe

<400> SEQUENCE: 150

Gln Arg Phe Xaa Thr Gly His Phe Gly Gly Leu Xaa Pro Cys Asn Gly
1               5                   10                  15

Pro

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 2-pyridylAla

<400> SEQUENCE: 151

Gln Arg Phe Xaa Thr Gly His Phe Gly Gly Leu Xaa Pro Cys Asn Gly
1               5                   10                  15

Pro

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 3-pyridylAla

<400> SEQUENCE: 152

Gln Arg Phe Xaa Thr Gly His Phe Gly Gly Leu Xaa Pro Cys Asn Gly
1               5                   10                  15
Pro

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 4-nitro-Phe

<400> SEQUENCE: 153

Gln Arg Phe Xaa Thr Gly His Phe Gly Gly Leu Xaa Pro Cys Asn Gly
1               5                   10                  15
Pro

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 2-nitro-Tyr

<400> SEQUENCE: 154

Gln Arg Phe Xaa Thr Gly His Phe Gly Gly Leu Xaa Pro Cys Asn Gly
1               5                   10                  15
Pro

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 4-fluoro-Phe
```

<400> SEQUENCE: 155

Gln Arg Phe Xaa Thr Gly His Phe Gly Gly Leu Xaa Pro Cys Asn Gly
1               5                   10                  15
Pro

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 156

Gln Arg Phe Xaa Thr Gly His Phe Gly Gly Leu Tyr Pro Cys Asn Gly
1               5                   10                  15
Pro

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 157

Gln Arg Phe Xaa Thr Gly His Phe Gly Gly His Tyr Pro Cys Asn Gly
1               5                   10                  15
Pro

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 158

Gln Arg Phe Xaa Thr Gly His Phe Gly Gly Ile Tyr Pro Cys Asn Gly
1               5                   10                  15
Pro

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 159

Gln Arg Phe Xaa Thr Gly His Phe Gly Gly Phe Tyr Pro Cys Asn Gly
1               5                   10                  15

Pro

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 160

Gln Arg Phe Xaa Thr Gly His Phe Gly Gly Trp Tyr Pro Cys Asn Gly
1               5                   10                  15

Pro

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 161

Gln Arg Phe Xaa Thr Gly His Phe Gly Gly Met Tyr Pro Cys Asn Gly
1               5                   10                  15

Pro

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 162

Gln Arg Phe Xaa Thr Gly His Phe Gly Gly Leu Tyr Pro Cys Asn Gly
1               5                   10                  15

Pro

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen

<400> SEQUENCE: 163

Arg Phe Xaa Thr Gly His Phe Gly Gly Trp Tyr Pro Cys
1               5                   10

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: Sar

<400> SEQUENCE: 164

Gln Arg Phe Xaa Thr Gly His Phe Gly Xaa Trp Tyr Pro Cys Asn Gly
1               5                   10                  15

Pro

<210> SEQ ID NO 165
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 165

Gln Arg Phe Xaa Thr Gly His Phe Gly Gly Gly Leu Tyr Pro Cys Asn
1               5                   10                  15

Gly Pro

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: Variable amino acid; see specification as filed
      for detailed embodiments

<400> SEQUENCE: 166

Gln Arg Phe Xaa Thr Gly His Phe Gly Xaa Tyr Pro Cys Asn Gly Pro
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: Variable amino acid; see specification as filed
      for detailed embodiments

<400> SEQUENCE: 167

Gln Arg Phe Xaa Thr Gly His Phe Gly Xaa Tyr Pro Cys Asn Gly Pro
1               5                   10                  15

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Dab

<400> SEQUENCE: 168

Gln Arg Phe Cys Thr Gly Xaa Phe Gly Gly Leu Tyr Pro Cys Asn Gly
1               5                   10                  15

Pro

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 169

Gln Arg Phe Xaa Thr Gly His Phe Gly Gly Leu Tyr Pro Cys Asn Gly
1               5                   10                  15

Pro

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: Thz

<400> SEQUENCE: 170

Gln Arg Phe Xaa Thr Gly Xaa Phe Gly Gly Leu Tyr Pro Cys Asn Gly
1               5                   10                  15

Pro
```

```
<210> SEQ ID NO 171
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: Dap

<400> SEQUENCE: 171

Gln Arg Phe Xaa Thr Gly Xaa Phe Gly Gly Leu Tyr Pro Cys Asn Gly
1               5                   10                  15

Pro

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: Dap(Guanyl)

<400> SEQUENCE: 172

Gln Arg Phe Xaa Thr Gly Xaa Phe Gly Gly Leu Tyr Pro Cys Asn Gly
1               5                   10                  15

Pro

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: (1Me)His

<400> SEQUENCE: 173

Gln Arg Phe Xaa Thr Gly Xaa Phe Gly Gly Leu Tyr Pro Cys Asn Gly
1               5                   10                  15

Pro

<210> SEQ ID NO 174
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: Dab

<400> SEQUENCE: 174

Gln Arg Phe Xaa Thr Gly Xaa Phe Gly Gly Leu Tyr Pro Cys Asn Gly
1               5                   10                  15

Pro

<210> SEQ ID NO 175
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: NMeHis

<400> SEQUENCE: 175

Arg Phe Xaa Thr Gly Xaa Phe Gly Gly Leu Tyr Pro Cys
1               5                   10

<210> SEQ ID NO 176
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: Thz
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 176

Arg Phe Xaa Thr Gly Xaa Phe Gly Xaa Xaa Tyr Pro Cys
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
```

```
<220> FEATURE:
<221> NAME/KEY: MOD_RES
<222> LOCATION: (6)..(6)
<223> OTHER INFORMATION: 2PyridylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 177

Arg Phe Xaa Thr Gly Xaa Phe Gly Xaa Xaa Tyr Pro Cys
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 3PyridylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 178

Arg Phe Xaa Thr Gly Xaa Phe Gly Xaa Xaa Tyr Pro Cys
1               5                   10

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: ThienylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 179

Arg Phe Xaa Thr Gly Xaa Phe Gly Xaa Xaa Tyr Pro Cys
1               5                   10

<210> SEQ ID NO 180
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: Dab
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 180

Arg Phe Xaa Thr Gly Xaa Phe Gly Xaa Xaa Tyr Pro Cys
1               5                   10

<210> SEQ ID NO 181
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 181

Arg Phe Xaa Thr Gly Xaa Phe Gly Xaa Xaa Tyr Pro Cys
1               5                   10

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 182
```

```
Arg Phe Xaa Thr Gly Lys Phe Gly Xaa Xaa Tyr Pro Cys
1               5                   10
```

<210> SEQ ID NO 183
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 183

```
Arg Phe Xaa Thr Gly Arg Phe Gly Xaa Xaa Tyr Pro Cys
1               5                   10
```

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4GuanylPhe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 184

```
Arg Phe Xaa Thr Gly Xaa Phe Gly Xaa Xaa Tyr Pro Cys
1               5                   10
```

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4-aminoPhe
<220> FEATURE:
<221> NAME/KEY: MOD_RES
<222> LOCATION: (9)..(9)
<223> OTHER INFORMATION: Sar

```
<220> FEATURE:
<221> NAME/KEY: MOD_RES
<222> LOCATION: (10)..(10)
<223> OTHER INFORMATION: NMeLeu

<400> SEQUENCE: 185

Arg Phe Xaa Thr Gly Xaa Phe Gly Xaa Xaa Tyr Pro Cys
1               5                   10

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: His(Me)

<400> SEQUENCE: 186

Arg Phe Xaa Thr Gly Xaa Phe Gly Gly Leu Tyr Pro Cys
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: His(Me)2

<400> SEQUENCE: 187

Arg Phe Xaa Thr Gly Xaa Phe Gly Gly Leu Tyr Pro Cys
1               5                   10

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: PropargylGly
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 188
```

Arg Phe Xaa Thr Gly Xaa Phe Gly Xaa Xaa Tyr Pro Cys
1               5                   10

<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 2-PyrrolidinylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 189

Arg Phe Xaa Thr Gly Xaa Phe Gly Xaa Xaa Tyr Pro Cys
1               5                   10

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 3-PiperidyalAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 190

Arg Phe Xaa Thr Gly Xaa Phe Gly Xaa Xaa Tyr Pro Cys
1               5                   10

<210> SEQ ID NO 191
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4-PiperidylAla

```
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 191

Arg Phe Xaa Thr Gly Xaa Phe Gly Xaa Xaa Tyr Pro Cys
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 192

Arg Phe Xaa Thr Gly Phe Phe Gly Xaa Xaa Tyr Pro Cys
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 193

Arg Phe Xaa Thr Gly Ala Phe Gly Xaa Xaa Tyr Pro Cys
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
```

<222> LOCATION: (6)..(6)
<223> OTHER INFORMATION: 4-PyridylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 194

Arg Phe Xaa Thr Gly Xaa Phe Gly Xaa Xaa Tyr Pro Cys
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: Thz(Me)
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 195

Arg Phe Xaa Thr Gly Xaa Phe Gly Xaa Xaa Tyr Pro Cys
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: trizolylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 196

Arg Phe Xaa Thr Gly Xaa Phe Gly Xaa Xaa Tyr Pro Cys
1               5                   10

<210> SEQ ID NO 197
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Ala

<400> SEQUENCE: 197

Gln Arg Phe Cys Thr Gly His Phe Xaa Gly Leu Tyr Pro Cys Asn Gly
1               5                   10                  15

Pro

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Ala

<400> SEQUENCE: 198

Gln Arg Phe Cys Thr Gly His Phe Gly Xaa Leu Tyr Pro Cys Asn Gly
1               5                   10                  15

Pro

<210> SEQ ID NO 199
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: D-Ala

<400> SEQUENCE: 199

Gln Arg Phe Cys Thr Gly His Phe Xaa Xaa Leu Tyr Pro Cys Asn Gly
1               5                   10                  15

Pro

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: beta-Ala

<400> SEQUENCE: 200

Gln Arg Phe Cys Gly His Phe Xaa Leu Tyr Pro Cys Asn Gly Pro
1               5                   10                  15

<210> SEQ ID NO 201
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Apa

<400> SEQUENCE: 201

Gln Arg Phe Cys Thr Gly His Phe Xaa Leu Tyr Pro Cys Asn Gly Pro
1               5                   10                  15

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen

<400> SEQUENCE: 202

Arg Phe Xaa Thr Gly His Phe Gly Gly Leu Tyr Pro Cys
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 4-aminomethyl-benzoic acid

<400> SEQUENCE: 203

Arg Phe Xaa Thr Gly His Phe Xaa Leu Tyr Pro Cys
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: (3-aminomethyl)-benzoic acid

<400> SEQUENCE: 204

Arg Phe Xaa Thr Gly His Phe Xaa Leu Tyr Pro Cys
1               5                   10

<210> SEQ ID NO 205
<211> LENGTH: 12
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 4-aminophenyl acetic acid

<400> SEQUENCE: 205

Arg Phe Xaa Thr Gly His Phe Xaa Leu Tyr Pro Cys
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-aminophenyl acetic acid

<400> SEQUENCE: 206

Arg Phe Xaa Thr Gly His Phe Xaa Leu Tyr Pro Cys
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-amino-2-oxo-1-piperidine-acetic acid

<400> SEQUENCE: 207

Arg Phe Xaa Thr Gly His Phe Xaa Leu Tyr Pro Cys
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-amino-2-oxo-1-piperidine-acetic acid

<400> SEQUENCE: 208

Arg Phe Xaa Thr Gly His Phe Xaa Leu Tyr Pro Cys
```

<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: (3S)-3-amino-2-oxo-1-piperidine-acetic acid

<400> SEQUENCE: 209

Arg Phe Xaa Thr Gly His Phe Xaa Leu Tyr Pro Cys
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-amino-N-1-carboxymethyl-2,3,4,5-tetrahydro-
      1H-[1]-benzazepine-2-one

<400> SEQUENCE: 210

Arg Phe Xaa Thr Gly His Phe Xaa Leu Tyr Pro Cys
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-amino-N-1-carboxymethyl-2,3,4,5-tetrahydro-
      1H-[1]-benzazepine-2-one

<400> SEQUENCE: 211

Arg Phe Xaa Thr Gly His Phe Xaa Leu Tyr Pro Cys
1               5                   10

<210> SEQ ID NO 212
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 5,5-bicyclic dipeptide mimic

<400> SEQUENCE: 212

Arg Phe Xaa Thr Gly His Phe Xaa Leu Tyr Pro Cys
1               5                   10

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 5,5-bicyclic dipeptide mimic

<400> SEQUENCE: 213

Arg Phe Xaa Thr Gly His Phe Xaa Leu Tyr Pro Cys
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 6,5-bicyclic dipeptide mimic

<400> SEQUENCE: 214

Arg Phe Xaa Thr Gly His Phe Xaa Leu Tyr Pro Cys
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(S)-3-amino-2-oxo-1-azepine acetic acid

<400> SEQUENCE: 215

Arg Phe Xaa Thr Gly His Phe Xaa Leu Tyr Pro Cys
1               5                   10

<210> SEQ ID NO 216
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(S)-3-amino-2-oxo-1-pyrrolidine acetic acid

<400> SEQUENCE: 216

Arg Phe Xaa Thr Gly His Phe Xaa Leu Tyr Pro Cys
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: (3R)-3-amino-1-carboxymethyl-valerolactam
<220> FEATURE:
<221> NAME/KEY: MOD_RES
<222> LOCATION: (9)..(9)
<223> OTHER INFORMATION: NMeLeu

<400> SEQUENCE: 217

Arg Phe Xaa Thr Gly His Phe Xaa Xaa Tyr Pro Cys
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (4)..(4)
<223> OTHER INFORMATION: NMeAla
<220> FEATURE:
<221> NAME/KEY: MOD_RES
<222> LOCATION: (8)..(8)
<223> OTHER INFORMATION: (3R)-3-amino-1-carboxymethyl-valerolactam
<220> FEATURE:
<221> NAME/KEY: MOD_RES
<222> LOCATION: (9)..(9)
<223> OTHER INFORMATION: NMeLeu

<400> SEQUENCE: 218

Arg Phe Xaa Xaa Gly His Phe Xaa Xaa Tyr Pro Cys
1               5                   10

<210> SEQ ID NO 219
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(S)-3-amino-2-oxo-1-azepine acetic acid
<220> FEATURE:
<221> NAME/KEY: MOD_RES
<222> LOCATION: (9)..(9)
<223> OTHER INFORMATION: NMeLeu

<400> SEQUENCE: 219

Arg Phe Xaa Thr Gly His Phe Xaa Xaa Tyr Pro Cys
1               5                   10

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Dab

<400> SEQUENCE: 220

Gln Arg Phe Asp Thr Gly His Phe Gly Gly Leu Tyr Pro Xaa Asn Gly
1               5                   10                  15

Pro

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln Arg Phe Asp Thr Gly His Phe Gly Gly Leu Tyr Pro Lys Asn Gly
1               5                   10                  15

Pro

<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab

<400> SEQUENCE: 222

Gln Arg Phe Xaa Thr Gly His Phe Gly Gly Leu Tyr Pro Glu Asn Gly
1               5                   10                  15

Pro

<210> SEQ ID NO 223
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gln Arg Phe Lys Thr Gly His Phe Gly Gly Leu Tyr Pro Glu Asn Gly
1               5                   10                  15

Pro

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gln Arg Phe Glu Thr Gly His Phe Gly Gly Leu Tyr Pro Lys Asn Gly
1               5                   10                  15

Pro

<210> SEQ ID NO 225
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Dab

<400> SEQUENCE: 225

Gln Arg Phe Glu Thr Gly His Phe Gly Gly Leu Tyr Pro Xaa Asn Gly
1               5                   10                  15

Pro

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Dap

<400> SEQUENCE: 226

Gln Arg Phe Glu Thr Gly His Phe Gly Gly Leu Tyr Pro Xaa Asn Gly
1               5                   10                  15

Pro

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (14)..(14)
<223> OTHER INFORMATION: Dap

<400> SEQUENCE: 227

Gln Arg Phe Asp Thr Gly His Phe Gly Gly Leu Tyr Pro Xaa Asn Gly
1               5                   10                  15

Pro

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln Arg Phe Lys Thr Gly His Phe Gly Gly Leu Tyr Pro Asp Asn Gly
1               5                   10                  15

Pro

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab

<400> SEQUENCE: 229

Gln Arg Phe Xaa Thr Gly His Phe Gly Gly Leu Tyr Pro Asp Asn Gly
1               5                   10                  15

Pro

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Orn

<400> SEQUENCE: 230

Gln Arg Phe Asp Thr Gly His Phe Gly Gly Leu Tyr Pro Xaa Asn Gly
1               5                   10                  15

Pro

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Orn

<400> SEQUENCE: 231
```

Gln Arg Phe Glu Thr Gly His Phe Gly Gly Leu Tyr Pro Xaa Asn Gly
1               5                   10                  15

Pro

<210> SEQ ID NO 232
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gln Arg Phe Asp Thr Gly His Phe Gly Gly Leu Tyr Lys Asn Gly Pro
1               5                   10                  15

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Ala

<400> SEQUENCE: 233

Gln Arg Phe Asp Thr Gly His Phe Gly Xaa Leu Tyr Pro Lys Asn Gly
1               5                   10                  15

Pro

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Ala

<400> SEQUENCE: 234

Gln Arg Phe Asp Thr Gly His Phe Xaa Gly Leu Tyr Pro Lys Asn Gly
1               5                   10                  15

Pro

<210> SEQ ID NO 235
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Asp Thr Gly His Phe Gly Gly Leu Tyr Pro Lys Asn Gly Pro
1               5                   10

<210> SEQ ID NO 236
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 236

Phe Asp Thr Gly His Phe Gly Gly Leu Tyr Pro Lys Asn Gly Pro
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Arg Phe Asp Thr Gly His Phe Gly Gly Leu Tyr Pro Lys Asn Gly Pro
1               5                   10                  15

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gln Arg Phe Asp Thr Gly His Phe Gly Gly Leu Tyr Pro Lys Asn Gly
1               5                   10                  15

Pro

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gln Arg Phe Asp Thr Gly His Phe Gly Gly Leu Tyr Pro Lys Asn
1               5                   10                  15

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dap

<400> SEQUENCE: 240

Gln Arg Phe Xaa Thr Gly His Phe Gly Gly Leu Tyr Pro Asp Asn Gly
1               5                   10                  15

Pro

<210> SEQ ID NO 241
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (4)..(4)
<223> OTHER INFORMATION: Dap

<400> SEQUENCE: 241

Gln Arg Phe Xaa Thr Gly His Phe Gly Gly Leu Tyr Pro Glu Asn Gly
1               5                   10                  15

Pro

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Orn

<400> SEQUENCE: 242

Gln Arg Phe Xaa Thr Gly His Phe Gly Gly Leu Tyr Pro Asp Asn Gly
1               5                   10                  15

Pro

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Orn

<400> SEQUENCE: 243

Gln Arg Phe Xaa Thr Gly His Phe Gly Gly Leu Tyr Pro Glu Asn Gly
1               5                   10                  15

Pro

<210> SEQ ID NO 244
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Arg Phe Asp Thr Gly His Phe Gly Gly Leu Tyr Pro Lys
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Arg Phe Asp Thr Gly His Phe Gly Gly Leu Tyr Pro Lys
1               5                   10
```

```
<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 246

Gln Arg Phe Asp Thr Gly His Phe Gly Xaa Leu Tyr Pro Lys Asn Gly
1               5                   10                  15

Pro

<210> SEQ ID NO 247
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gln Arg Phe Ser Thr Gly His Phe Gly Gly Leu Tyr Pro Ser Asn Gly
1               5                   10                  15

Pro

<210> SEQ ID NO 248
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: D-Pro

<400> SEQUENCE: 248

Gln Arg Phe Val Thr Gly His Phe Xaa Xaa Leu Tyr Pro Ala Asn Gly
1               5                   10                  15

Pro

<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 249

Gln Arg Phe Val Thr Gly His Phe Gly Xaa Leu Tyr Pro Ala Asn Gly
1               5                   10                  15

Pro

<210> SEQ ID NO 250
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 250

Gln Arg Phe Val Thr Gly His Phe Xaa Gly Leu Tyr Pro Ala Asn Gly
1               5                   10                  15

Pro

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 251

Gln Arg Phe Leu Thr Gly His Phe Gly Xaa Leu Tyr Pro Ala Asn Gly
1               5                   10                  15

Pro

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 252

Gln Arg Phe Ile Thr Gly His Phe Gly Xaa Leu Tyr Pro Ala Asn Gly
1               5                   10                  15

Pro

<210> SEQ ID NO 253
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 253

Gln Arg Phe Phe Thr Gly His Phe Gly Xaa Leu Tyr Pro Ala Asn Gly
1               5                   10                  15

Pro

<210> SEQ ID NO 254
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 254

Gln Arg Phe Tyr Thr Gly His Phe Gly Xaa Leu Tyr Pro Ala Asn Gly
1               5                   10                  15

Pro

<210> SEQ ID NO 255
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 255

Gln Arg Phe Trp Thr Gly His Phe Gly Xaa Leu Tyr Pro Ala Asn Gly
1               5                   10                  15

Pro

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 256

Gln Arg Phe Val Thr Gly His Phe Gly Xaa Leu Tyr Pro Val Asn Gly
1               5                   10                  15

Pro

<210> SEQ ID NO 257
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 257

Gln Arg Phe Val Thr Gly His Phe Gly Xaa Leu Tyr Pro Leu Asn Gly
1               5                   10                  15

Pro

<210> SEQ ID NO 258
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 258

Gln Arg Phe Val Thr Gly His Phe Gly Xaa Leu Tyr Pro Ile Asn Gly
1               5                   10                  15
Pro

<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 259

Gln Arg Phe Val Thr Gly His Phe Gly Xaa Leu Tyr Pro Phe Asn Gly
1               5                   10                  15
Pro

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 260

Gln Arg Phe Val Thr Gly His Phe Gly Xaa Leu Tyr Pro Tyr Asn Gly
1               5                   10                  15
Pro

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 261

Gln Arg Phe Val Thr Gly His Phe Gly Xaa Leu Tyr Pro Trp Asn Gly
1               5                   10                  15
Pro

<210> SEQ ID NO 262
<211> LENGTH: 17
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 262

Gln Arg Phe Val Thr Gly His Phe Gly Xaa Val Tyr Pro Ala Asn Gly
1               5                   10                  15

Pro

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 263

Gln Arg Phe Val Thr Gly His Phe Gly Xaa Ile Tyr Pro Ala Asn Gly
1               5                   10                  15

Pro

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 264

Gln Arg Phe Val Thr Gly His Phe Gly Xaa Phe Tyr Pro Ala Asn Gly
1               5                   10                  15

Pro

<210> SEQ ID NO 265
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 265

Gln Arg Phe Val Thr Gly His Phe Gly Xaa Tyr Tyr Pro Ala Asn Gly
1               5                   10                  15

Pro

<210> SEQ ID NO 266
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 266

Gln Arg Phe Val Thr Gly His Phe Gly Xaa Trp Tyr Pro Ala Asn Gly
1               5                   10                  15

Pro

<210> SEQ ID NO 267
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 267

Gln Arg Phe Val Thr Gly His Phe Gly Xaa Trp Tyr Pro Ile Asn Gly
1               5                   10                  15

Pro

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 268

Arg Phe Val Thr Gly His Phe Gly Xaa Trp Tyr Pro
1               5                   10

<210> SEQ ID NO 269
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 269

Arg Phe Val Thr Gly His Phe Gly Xaa Trp Tyr Pro Ala Asn Gly Pro
1               5                   10                  15

<210> SEQ ID NO 270
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (8)..(8)
<223> OTHER INFORMATION: D-Pro

<400> SEQUENCE: 270

Phe Val Thr Gly His Phe Gly Xaa Trp Tyr Pro Ala
1               5                   10

<210> SEQ ID NO 271
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Pro

<400> SEQUENCE: 271

Val Thr Gly His Phe Gly Xaa Trp Tyr Pro Ala
1               5                   10

<210> SEQ ID NO 272
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 272

Arg Phe Val Thr Gly His Phe Gly Xaa Xaa Tyr Pro Ala
1               5                   10

<210> SEQ ID NO 273
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 273

Arg Phe Val Thr Gly His Phe Gly Xaa Trp Tyr Pro Ala
1               5                   10

<210> SEQ ID NO 274
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sar
```

```
<220> FEATURE:
<221> NAME/KEY: MOD_RES
<222> LOCATION: (10)..(10)
<223> OTHER INFORMATION: NMeLeu

<400> SEQUENCE: 274

Arg Phe Val Thr Gly His Phe Gly Xaa Xaa Tyr Pro Ala
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-amino-2-oxo-1-piperidine-acetic acid

<400> SEQUENCE: 275

Arg Phe Val Thr Gly His Phe Xaa Leu Tyr Pro Ala
1               5                   10

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-amino-2-oxo-1-piperidine-acetic acid

<400> SEQUENCE: 276

Arg Phe Val Thr Gly His Phe Xaa Leu Tyr Pro Ala
1               5                   10

<210> SEQ ID NO 277
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-amino-N-1-carboxymethyl-2,3,4,5-tetrahydro-
      1H-[1]-benzazepine-2-one

<400> SEQUENCE: 277

Arg Phe Val Thr Gly His Phe Xaa Leu Tyr Pro Ala
1               5                   10

<210> SEQ ID NO 278
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-amino-N-1-carboxymethyl-2,3,4,5-tetrahydro-
      1H-[1]-benzazepine-2-one

<400> SEQUENCE: 278
```

```
Arg Phe Val Thr Gly His Phe Xaa Leu Tyr Pro Ala
1               5                   10
```

<210> SEQ ID NO 279
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-aminophenyl acetic acid

<400> SEQUENCE: 279

```
Arg Phe Val Thr Gly His Phe Xaa Leu Tyr Pro Ala
1               5                   10
```

<210> SEQ ID NO 280
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: 3-amino-2-oxo-1-piperidine-acetic acid

<400> SEQUENCE: 280

```
Gln Arg Phe Val Thr Gly His Phe Xaa Trp Tyr Pro Ile Asn Gly Pro
1               5                   10                  15
```

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 5,5-bicyclic dipeptide mimic

<400> SEQUENCE: 281

```
Arg Phe Val Thr Gly His Phe Xaa Leu Tyr Pro Ala
1               5                   10
```

<210> SEQ ID NO 282
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 6,5-bicyclic dipeptide mimic

<400> SEQUENCE: 282

```
Arg Phe Val Thr Gly His Phe Xaa Leu Tyr Pro Ala
1               5                   10
```

<210> SEQ ID NO 283
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3(S)-3-amino-2-oxo-1-azepine acetic acid

<400> SEQUENCE: 283

Arg Phe Val Thr Gly His Phe Xaa Leu Tyr Pro Ala
1               5                   10

<210> SEQ ID NO 284
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Phe Cys Thr Gly His Phe Gly Gly Leu Tyr Pro Cys
1               5                   10

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Pro

<400> SEQUENCE: 285

Gln Arg Phe Xaa Thr Gly His Phe Gly Xaa Leu Tyr Pro Cys Asn Gly
1               5                   10                  15

Pro

<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (9)..(9)
<223> OTHER INFORMATION: NMeLeu

<400> SEQUENCE: 286

Arg Phe Xaa Thr Gly His Phe Xaa Xaa Tyr Pro Cys
1               5                   10

<210> SEQ ID NO 287
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (4)..(4)
<223> OTHER INFORMATION: NMeAla
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (9)..(9)
<223> OTHER INFORMATION: NMeLeu

<400> SEQUENCE: 287

Arg Phe Xaa Xaa Gly His Phe Xaa Xaa Tyr Pro Cys
1               5                   10

<210> SEQ ID NO 288
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 288

Arg Phe Xaa Thr Gly His Phe Gly Xaa Xaa Tyr Pro Cys
1               5                   10

<210> SEQ ID NO 289
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 289

Arg Phe Xaa Thr Gly His Phe Gly Xaa Xaa Tyr Pro Cys
1               5                   10
```

```
<210> SEQ ID NO 290
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 290

Arg Phe Xaa Thr Gly His Phe Gly Xaa Xaa Tyr Pro Cys
1               5                   10

<210> SEQ ID NO 291
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 291

Arg Phe Xaa Thr Gly His Phe Gly Xaa Xaa Tyr Pro Cys
1               5                   10

<210> SEQ ID NO 292
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4GuPhe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 292

Arg Phe Xaa Thr Gly Xaa Phe Gly Xaa Xaa Tyr Pro Cys
```

```
1               5                   10
```

<210> SEQ ID NO 293
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 293

```
Arg Phe Xaa Thr Gly His Phe Gly Xaa Xaa Tyr Pro Cys Gly
1               5                   10
```

<210> SEQ ID NO 294
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 294

```
Arg Phe Xaa Thr Gly His Phe Gly Xaa Xaa Tyr Pro Cys Gly
1               5                   10
```

<210> SEQ ID NO 295
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 295

```
Arg Phe Asp Thr Gly His Phe Gly Xaa Xaa Tyr Pro Lys
1               5                   10
```

<210> SEQ ID NO 296
<211> LENGTH: 17
<212> TYPE: PRT

<210> SEQ ID NO 297
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Gln Arg Phe Asp Thr Gly His Phe Gly Gly Leu Tyr Pro Lys Asn Gly
1               5                   10                  15

Pro

<210> SEQ ID NO 297
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Gln Arg Phe Asp Thr Gly His Phe Gly Gly Leu Tyr Pro Lys Asn Gly
1               5                   10                  15

Pro

<210> SEQ ID NO 298
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Gln Arg Phe Asp Thr Gly His Phe Gly Gly Leu Tyr Pro Lys Asn Gly
1               5                   10                  15

Pro

<210> SEQ ID NO 299
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 299

Gln Arg Phe Asp Thr Gly His Phe Gly Gly Leu Tyr Pro Lys Asn Gly
1               5                   10                  15

Pro

<210> SEQ ID NO 300
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 300

Gln Arg Phe Asp Thr Gly His Phe Gly Gly Leu Tyr Pro Lys Asn Gly
1               5                   10                  15

Pro

<210> SEQ ID NO 301
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen

<400> SEQUENCE: 301

Arg Phe Xaa Thr Gly His Phe Gly Gly Leu Tyr Pro Cys
1               5                   10

<210> SEQ ID NO 302
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 302

Gln Arg Phe Xaa Thr Gly His Phe Gly Gly Leu Tyr Pro Cys Asn Gly
1               5                   10                  15

Pro

<210> SEQ ID NO 303
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 303

Gln Arg Phe Asp Thr Gly His Phe Gly Xaa Leu Tyr Pro Lys Asn Gly
1               5                   10                  15

Pro

<210> SEQ ID NO 304
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (11)..(11)
<223> OTHER INFORMATION: NMeLeu

<400> SEQUENCE: 304

Gln Arg Phe Asp Thr Gly His Phe Xaa Gly Xaa Tyr Pro Lys Asn Gly
1               5                   10                  15

Pro

<210> SEQ ID NO 305
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 305

Gln Arg Phe Xaa Thr Gly His Phe Gly Gly Leu Tyr Pro Cys Asn Gly
1               5                   10                  15

Pro

<210> SEQ ID NO 306
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 306

Arg Phe Xaa Thr Gly His Phe Gly Xaa Xaa Tyr Pro Cys
1               5                   10

<210> SEQ ID NO 307
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 307

Arg Phe Xaa Thr Gly His Phe Gly Xaa Xaa Tyr Pro Cys
1               5                   10

<210> SEQ ID NO 308
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 308

Arg Phe Xaa Thr Gly His Phe Gly Xaa Xaa Tyr Pro Cys
1               5                   10

<210> SEQ ID NO 309
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 309

Arg Phe Xaa Thr Gly His Phe Gly Xaa Xaa Tyr Pro Cys
1               5                   10

<210> SEQ ID NO 310
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 310

Arg Phe Xaa Thr Gly His Phe Gly Xaa Xaa Tyr Pro Cys
1               5                   10

<210> SEQ ID NO 311
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
```

```
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 311

Arg Phe Xaa Thr Gly His Phe Gly Xaa Xaa Tyr Pro Cys
1               5                   10

<210> SEQ ID NO 312
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 312

Arg Phe Xaa Thr Gly His Phe Gly Xaa Xaa Tyr Pro Cys
1               5                   10

<210> SEQ ID NO 313
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 313

Arg Phe Xaa Thr Gly His Phe Gly Xaa Xaa Tyr Pro Cys
1               5                   10

<210> SEQ ID NO 314
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
```

```
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 314

Arg Phe Xaa Thr Gly His Phe Gly Xaa Xaa Tyr Pro Cys Gly
1               5                   10

<210> SEQ ID NO 315
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 315

Arg Phe Xaa Thr Gly His Phe Gly Xaa Xaa Tyr Pro Cys Gly Gly
1               5                   10                  15

<210> SEQ ID NO 316
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: Variable non-naturally occuring amino acid; see
      specification as filed for detailed emodiments
<220> FEATURE:
<221> NAME/KEY: MOD_RES
<222> LOCATION: (9)..(9)
<223> OTHER INFORMATION: NMeLeu

<400> SEQUENCE: 316

Arg Phe Xaa Thr Gly His Phe Xaa Xaa Tyr Pro Cys
1               5                   10

<210> SEQ ID NO 317
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
```

```
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 317

Arg Phe Xaa Thr Gly His Phe Gly Xaa Xaa Tyr Pro Cys
1               5                   10

<210> SEQ ID NO 318
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Arg Phe Cys Thr Gly His Phe Gly Gly Leu Tyr Pro Cys
1               5                   10

<210> SEQ ID NO 319
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 319

Arg Phe Xaa Thr Gly His Phe Gly Xaa Xaa Tyr Pro Cys
1               5                   10

<210> SEQ ID NO 320
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln Arg Phe Asp Thr Gly His Phe Gly Gly Leu Tyr Pro Lys Asn Gly
1               5                   10                  15

Pro

<210> SEQ ID NO 321
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
```

```
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 321

Arg Phe Xaa Thr Gly His Phe Gly Xaa Xaa Tyr Pro Cys
1               5                   10

<210> SEQ ID NO 322
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Arg Phe Cys Thr Gly His Phe Gly Gly Leu Tyr Pro Cys
1               5                   10
```

US 8,101,186 B2

PEPTIDES THAT BLOCK THE BINDING OF IGG TO FCRN

PRIOR APPLICATIONS

This application claims priority to U.S. Provisional Application Nos. 60/774,853, filed Feb. 17, 2006, and 60/805,634, filed Jun. 23, 2006, the contents of which are hereby incorporated by reference in their entirety.

FIELD OF THE INVENTION

The invention generally relates to the field of immunomodulators. More specifically, the invention relates to peptides which bind to the Fc neonatal Receptor (FcRn) and inhibit binding of the FcRn to a Fc portion of an immunoglobulin G (IgG), thereby modulating serum IgG levels. The invention further relates to peptide modulators of FcRn activity that can prevent FcRn from functioning in cellular mechanisms related to the maintenance of IgG levels in the serum, medicaments comprising those peptides, and methods of treating a subject for diseases and disorders that can be alleviated by lowering serum IgG levels by administering those medicaments.

BACKGROUND OF THE INVENTION

The most abundant antibody isotype in the serum is IgG, which has a critical role in mediating protection against pathogens as well as in mediating allergic and inflammatory responses that hasten recruitment of immune system components to the tissues, mucosae, and dermal surfaces. Junghans, *Immunologic Research* 16 (1):29 (1997). Moreover, IgG is also a key component of a variety of autoimmune diseases.

Under normal conditions, the half-life of IgG in the serum is a prolonged period relative to the serum half-life of other plasma proteins. For example, the serum half-life of IgG is 5 to 7 days in mice and 22-23 days in humans. Roopenian et al., *J. Immunology* 170:3528 (2003); Junghans and Anderson, *Proc. Natl. Acad. Sci. USA* 93:5512 (1996). In part, this long half-life of IgG is due to its binding to the Fc receptor, FcRn. FcRn binds to the constant region of IgG, known as Fc. Although FcRn was originally characterized as a neonatal transport receptor for maternal IgG, it also functions in adults to protect IgG from degradation. FcRn binds to pinocytosed IgG to protect it from degradative lysosomes and then recycles it back to the extracellular compartment. Junghans and Anderson, *Proc. Natl. Acad. Sci. USA* 93:5512 (1996), Roopenian et al., *J. Immunology* 170:3528 (2003). If the concentration of IgG reaches a level that exceeds available FcRn, unbound IgG will not be protected from degradative mechanisms and will consequently have a shorter serum half-life. Brambell et al., *Nature* 203:1352 (1964). Furthermore, although FcRn is expressed on the cell surface, it is believed that much of FcRn is intracellular and is associated with endoplasmic vesicle membranes, and that the interaction between IgG and FcRn occurs intracellularly after IgG is pinocytosed into the cell.

Structurally, FcRn exists as a heterodimer composed of one light chain, termed a beta ($\beta$) chain, and one non-covalently bound heavy chain, termed an alpha ($\alpha$) chain. The light chain of FcRn, which is better known as $\beta_2$-microglobulin ($\beta_2$m), is also a component of the Major Histocompatibility complex I (MHC I). The FcRn a chain is a 46 kD protein composed of an extracellular domain that is divided into three subdomains, $\alpha 1$, $\alpha 2$, and $\alpha 3$; a transmembrane region; and a relatively short cytoplasmic tail. Burmeister et al., *Nature* 372:336 (1994).

FcRn was first identified in the neonatal rat gut where it functions to mediate the absorption of IgG antibody from the mother's milk and facilitates its transport to the circulatory system. Leach et al., *J. Immunology* 157:3317 (1996). FcRn has also been isolated from the human placenta where it mediates absorption and transport of maternal IgG to the fetal circulation. In adults, FcRn is expressed in epithelial tissue (U.S. Pat. Nos. 6,030,613 and 6,086,875), such as, but not limited to, the lung (Israel et al., *Immunology* 92:69 (1997)), intestinal and renal proximal tubular epithelium (Kobayashi et al., *Am. J. Physiol.* (2002); *Renal Physiol.* 282:F358 (2002)), as well as nasal, vaginal, and biliary tree surfaces. In addition, the ubiquitous expression of FcRn on endothelial cells is suggestive of its importance in IgG homeostasis. Ward et al., *International Immunology* 15 (2):187 (2002); Ghetie et al., *Eur. J. Immunology* 26:690 (1996).

In general, FcRn functions in IgG homeostasis by antagonizing the catabolism of IgG by binding to the Fc portion of IgG. Once pinocytosed, IgG is captured in intracellular vacuoles that are beginning to fuse with acidic early endosomes. Crystallographic studies suggest the stoichiometry of the FcRn-IgG complex is composed of two molecules of FcRn to one IgG (Burmeister et al., *Nature* 372:336 (1994)) and binding of the two molecules is thought to occur on the Fc portion of IgG near the interface of the CH2 and CH3 domains (Burmeister et al., *Nature* 372:379 (1994)). The endosomal fusion event represents one stage of the lysosomal degradative pathway, which degrades or catabolizes complex biomolecules contained within the endosome into constitutive components. The low pH environment of the early endosome promotes the binding of FcRn to IgG as well as the release of any antigen bound to the IgG. Consequently, the antigen is degraded and the FcRn-IgG complex avoids degradation and is ultimately recycled to the cell surface where the physiological pH of the extracellular environment promotes the release of the IgG from FcRn.

In order to study the contributions of FcRn to IgG homeostasis, mice have been engineered so that at least part of the genes encoding $\beta_2$m and FcRn heavy chain have been "knocked out" so that these proteins are not expressed. WO 02/43658; Junghans and Anderson, *Proc. Natl. Acad. Sci. USA* 93:5512 (1996). In both of these knockout mouse lines, the half-life and the concentration of IgG in the serum are dramatically reduced, suggesting a FcRn-dependent mechanism related to IgG homeostasis.

The inhibition of IgG binding to FcRn reduces IgG serum half-life by preventing IgG recycling. Therefore, agents that block or antagonize the binding of IgG to FcRn may be used in methods of regulating, treating or preventing disorders involving immune reactions, such as, e.g., autoimmune and inflammatory diseases and disorders characterized by the presence of inappropriately expressed IgG antibodies. One example of a method of blocking IgG Fc binding to FcRn involves the generation of blocking antibodies to FcRn. Indeed, antibodies capable of blocking the binding of FcRn with IgG have been generated using a FcRn heavy chain knockout mouse line (WO 02/43658). Recently, peptides have been identified that bind to FcRn complexes. Kolonin et al., *Proc. Natl. Acad. Sci. USA* 99(20):13055-60 (2002); U.S. Pat. No. 6,212,022. However, at this time additional agents are needed to regulate, treat, or prevent conditions, diseases, and disorders characterized by immune reactions.

SUMMARY OF THE INVENTION

Accordingly, the present invention provides peptides which specifically bind to FcRn and inhibit IgG Fc from binding to FcRn, thereby preventing IgG from recycling by preventing FcRn from functioning in its role of protecting IgG from degradation by the lysosomes. In exemplary embodiments, the peptides bind to FcRn and inhibit the IgG1, IgG2, IgG3, or IgG4 subclasses of Fc from binding to FcRn.

In some embodiments, the peptides of the invention comprise the sequence:

-Gly-$X_6$—$X_7$—$X_8$—$X_9$—$X_{10}$—$X_{11}$— wherein:

$X_6$ is chosen from positively charged amino acids, aromatic amino acids, positively charged aromatic amino acids, and analogs thereof;

$X_7$ is chosen from phenylalanine and phenylalanine analogs, $X_8$ and $X_9$ are each independently chosen from glycine, sarcosine, aspartic acid, D-amino acids, α-aminoisobutyric acid, and analogs thereof, or $X_8$, when taken together with $X_9$, forms a dipeptide mimetic;

$X_{10}$ is chosen from amino acids and analogs thereof, or $X_{10}$, when taken together with $X_9$, forms a dipeptide mimetic;

$X_{11}$ is chosen from tyrosine and tyrosine analogs.

Alternatively, the peptides of the invention may comprise the sequence:

$R_1$-Gly-$X_6$—$X_7$—$X_8$—$X_9$—$X_{10}$—$X_{11}$—$R_2$ wherein:

$R_1$ has the formula $X_1$—$X_2$—$X_3$—$X_4$— wherein $X_1$ is chosen from hydrogen, acyl, and amino acid protecting groups;

$X_2$ is absent or is chosen from an amino acid and peptides of 2-15 amino acids in length, and analogs thereof;

$X_3$ is absent or is an amino acid or analog thereof that is capable of forming a bridge with $X_{10}$, $X_{12}$, or $X_{13}$, wherein the bridge is chosen from an amino terminus to carboxy terminus bridge, a side chain to backbone bridge, and a side chain to side chain bridge; and $X_4$ is absent or is chosen from an amino acid, peptides of 2-15 amino acids in length, and analogs thereof;

$X_6$, —$X_7$, —$X_8$, —$X_9$, —$X_{10}$, and —$X_{11}$ are as defined above, and $R_2$ has the formula —$X_{12}$—$X_{13}$—$X_{14}$—$X_{15}$ wherein $X_{12}$ is absent or is an amino acid or analog thereof;

$X_{13}$ is absent or is an amino acid or analog thereof;

$X_{14}$ is absent or is chosen from an amino acid, peptides of 2-15 amino acids in length, and analogs thereof; and $X_{15}$ is an amino group or a carboxy protecting group.

The peptides of the invention are typically at least 7 and as many as 50 amino acids long. Peptides of the invention may exist as a multimer, such as, e.g., a dimer, a trimer, or a tetramer. In some embodiments, the peptides of the invention may be more susceptible to pinocytosis, which enables more rapid binding of the peptide and consequently, less excretion by the kidney. The invention further relates to pharmaceutical compositions comprising one or more peptides of the invention.

Peptides of the invention may comprise:

a) an amino acid sequence chosen from:

| | |
|---|---|
| QRFCTGHFGGLYPCNGP, | (SEQ ID NO:1) |
| GGGCVTGHFGGIYCNYQ, | (SEQ ID NO:2) |
| KIICSPGHFGGMYCQGK, | (SEQ ID NO:3) |
| PSYCIEGHIDGIYCFNA, and | (SEQ ID NO:4) |
| NSFCRGRPGHFGGCYLF; | (SEQ ID NO:5) | b) an amino acid sequence that is substantially identically to one or more of SEQ ID NO:1, SEQ ID NO:2, SEQ ID NO:3, SEQ ID NO:4 and SEQ ID NO:5;

c) an amino acid sequence that is at least 80% identical to one or more of SEQ ID NO:1, SEQ ID NO:2, SEQ ID NO:3, SEQ ID NO:4 and SEQ ID NO:5;

d) SEQ ID NO:1, SEQ ID NO:2, SEQ ID NO:3, SEQ ID NO:4 or SEQ ID NO:5 modified by one, two, three, four, or five deletion, substitution, or addition mutations;

e) SEQ ID NO:1, SEQ ID NO:2, SEQ ID NO:3, SEQ ID NO:4 or SEQ ID NO:5 modified by at least one amino acid substitution, wherein the at least one amino acid is substituted with a naturally occurring amino acid;

f) SEQ ID NO:1, SEQ ID NO:2, SEQ ID NO:3, SEQ ID NO:4 or SEQ ID NO:5 modified by at least one amino acid substitution, wherein the at least one amino acid is substituted with a D-amino acid and analogs thereof;

g) SEQ ID NO:1, SEQ ID NO:2, SEQ ID NO:3, SEQ ID NO:4 or SEQ ID NO:5 modified by at least one amino acid substitution, wherein the at least one amino acid is substituted with an N-methylated amino acid;

h) SEQ ID NO:1, SEQ ID NO:2, SEQ ID NO:3, SEQ ID NO:4 or SEQ ID NO:5 modified by at least one amino acid substitution, wherein the at least one amino acid is substituted with a non-naturally occurring amino acid; and i) SEQ ID NO:1, SEQ ID NO:2, SEQ ID NO:3, SEQ ID NO:4 or SEQ ID NO:5 modified by at least one amino acid substitution, wherein the at least one amino acid is substituted with an amino acid mimetic.

The invention further relates to a method of regulating IgG levels in the serum of a subject comprising administering to the subject a therapeutically effective amount of a composition comprising one or more peptides of the invention capable of binding to and preventing the FcRn from binding to the Fc portion of an IgG molecule. In certain embodiments, the methods of the invention are employed to reduce the half-life of soluble IgG in the serum of a subject. The result of administering a composition of the invention is that the half-life of soluble IgG in the serum of the subject is reduced compared to the half-life of IgG in the serum of the subject prior to administration of the peptide.

The invention further provides methods for inhibiting binding of the Fc portion of a human IgG to FcRn to effect a decrease in the serum concentration of the Fc portion of IgG for a FcRn as compared to the serum concentration of IgG before treatment. The method of decreasing serum concentration of IgG comprises administering to the subject a therapeutically effective amount of a composition comprising one or more peptides of the invention capable of binding to FcRn and preventing the FcRn from binding to the Fc portion of an IgG molecule. In one embodiment, the decrease in the serum concentration of human IgG is at least 5%, such as a decrease of at least 15%, or a decrease in the serum concentration of human IgG of at least 25%.

One embodiment of the invention provides a method of treating a subject who has at least one autoimmune disease comprising administering to the subject a therapeutically effective amount of a composition comprising one or more peptides of the invention capable of binding to FcRn and preventing the FcRn from binding to the Fc portion of an IgG molecule. An alternate embodiment of the invention provides a method of treating a subject with at least one inflammatory disorder by administering to the subject a therapeutically effective amount of a composition comprising one or more peptides of the invention capable of binding to FcRn and preventing the FcRn from binding to the Fc portion of an IgG molecule. In other embodiments, the methods of the invention may be used to prevent, treat, or regulate an immune response to a therapeutic protein or a gene therapy vector.

Additional embodiments, objects, and advantages of the invention are set forth in part in the description which follows and in part, will be obvious from the description, or may be learned by practice of the invention. These embodiments, objects, and advantages of the invention may be realized and attained by means of the elements and combinations particularly pointed out in the appended claims.

It is to be understood that both the foregoing general description and the following detailed description are only exemplary and explanatory and are not restrictive of the invention as claimed.

BRIEF DESCRIPTION OF THE DRAWINGS

FIG. 1 shows the cDNA sequences of the human full length FcRn and human beta-2 microglobulin ($\beta_2$m) open reading frames (ORFs).

DESCRIPTION OF THE EMBODIMENTS

I. Definitions

Figure 2:
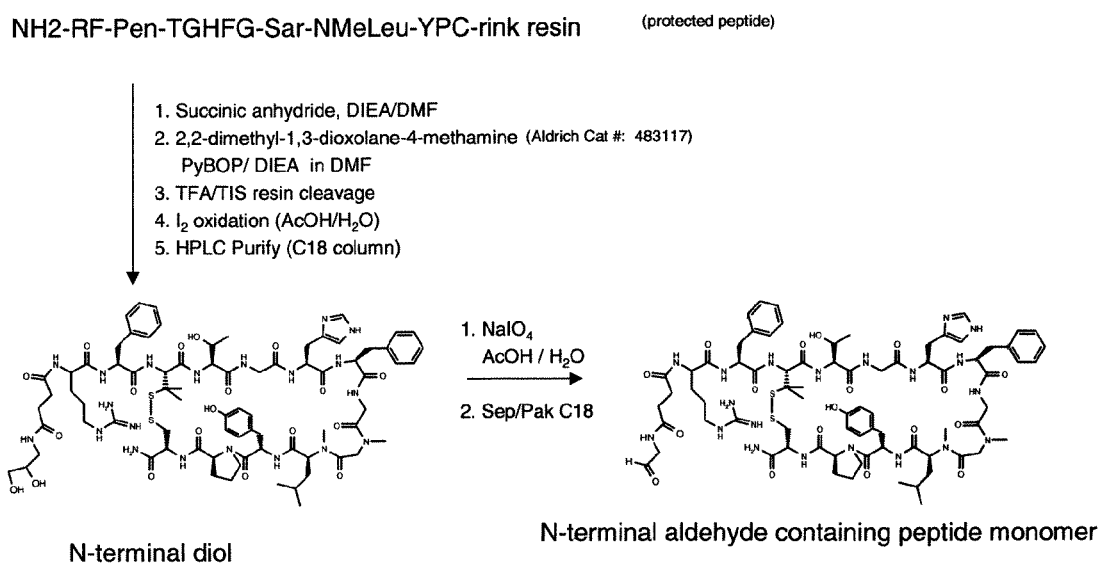
FIG. 2 shows an overview of the synthesis of N-terminal aldehyde peptide monomers (SEQ ID NO: 319).

"Affinity" refers to the characteristics of the binding interaction between two biologically active molecules that indicates the strength of the binding interaction. The measure of affinity is reported as a dissociation constant ($K_D$), which is the concentration, normally reported in nM, pM, or fM, in a solution comprising a biologically active molecule at which the biologically active molecule begins to no longer bind (dissociate) to its binding partner under specified conditions. Affinity strength is inversely related to the value of the $K_D$.

The term "amino acid," as used herein, refers to a compound containing a carboxylic acid group and an amino group. For example, an amino acid may have the structural formula $H_2N-[C(R)(R')]_n-C(O)OH$, where n is an integer greater than or equal to one, and R and R' are independently selected from hydrogen and amino acid side chains, and where R and R' may be taken together to form a carbocyclic or heterocyclic ring. For example, when n is equal to one, the amino acid of the formula $H_2N$—$[C(R)(R')]$—$C(O)OH$ is an alpha amino acid, and when n is equal to two, the amino acid of the formula $H_2N$—$C(R_1)(R_1')$—$C(R_2)(R_2')$—$C(O)OH$ is a beta amino acid, where $R_1$, $R_1'$, $R_2$, and $R_2'$ are each independently chosen from amino acid side chains, and where R and R', or $R_2$, and $R_2'$, may be taken together to form a carbocyclic or heterocyclic ring. The term "amino acid residue," as used herein, refers to an amino acid that is part of a peptide or protein, and having the formula —$N(H)$—$[C(R)(R')]_n$—$C(O)$—. The term "amino acid side chain" as used herein, refers to any side chain from a naturally-occurring or synthetic amino acid. For example, methyl may be referred to as an alanine side chain, and 2-amino-1-ethyl may be referred to as the side chain of 2,4-diaminobutanoic acid.

An amino acid may have R or S chirality at any chiral atom. The Fischer convention is used to designate the chirality of the alpha amino carbon of alpha amino acids, if the alpha amino carbon is chiral, as L- or D-. A "D-amino acid" is an amino acid having a D configuration at the alpha carbon. Where no specific configuration is indicated, one skilled in the art would understand the amino acid to be an L-amino acid. The amino acids described herein may also be in the form of racemic, non-racemic, and diastereomeric mixtures.

Exemplary amino acids may be chosen from the twenty encoded amino acids and analogs thereof, as well as from, e.g., other α-amino acids, β-amino acids, γ-amino acids, δ-amino acids, and ω-amino acids. Non-encoded amino acids are well known in the peptide art, such as those described in M. Bodanszky, *Principles of Peptide Synthesis*, 1st and 2nd revised ed., Springer-Verlag, New York, N.Y., (1984) and (1993), and Stewart and Young, *Solid Phase Peptide Synthesis*, 2nd ed., Pierce Chemical Co., Rockford, Ill., (1984). Encoded and non-encoded amino acids and amino acid analogs can be purchased commercially from, e.g., Novabiochem; Bachem; Sigma Chemical Co.; Advanced Chemtech, or synthesized using methods known in the art.

An amino acid may be chosen from, e.g., alanine, β-alanine, α-aminoadipic acid, 2-aminobutanoic acid, 4-aminobutanoic acid, 1-aminocyclopentanecarboxylic acid, 6-aminohexanoic acid, 2-aminoheptanedioic acid, 7-aminoheptanoic acid, 2-aminoisobutyric acid, aminomethylpyrrole carboxylic acid, 8-amino-3,6-dioxa-octanoic acid, aminopiperidinecarboxylic acid, 3-amino-propionic acid, aminoserine, aminotetrahydropyran-4-carboxylic acid, arginine, asparagine, aspartic acid, azetidine carboxylic acid, benzothiazolylalanine, butylglycine, carnitine, 4-chlorophenylalanine, citrulline, cyclohexylalanine, cyclohexylstatine, cysteine, 2,4-diaminobutanoic acid, 2,3-diaminopropionic acid, dihydroxyphenylalanine, dimethylthiazolidine carboxylic acid, glutamic acid, glutamine, glycine, histidine, homoserine, hydroxyproline, isoleucine, isonipecotic acid, leucine, lysine, methanoproline, methionine, norleucine, norvaline, ornithine, p-aminobenzoic acid, penicillamine, phenylalanine, phenylglycine, piperidinylalanine, piperidinylglycine, proline, pyrrolidinylalanine, sarcosine, selenocysteine, serine, statine, tetrahydropyranglycine, thienylalanine, threonine, tryptophan, tyrosine, valine, allo-isoleucine, allo-threonine, 2,6-diamino-4-hexanoic acid, 2,6-diaminopimelic acid, 2,3-diaminopropionic acid, dicarboxidine, homoarginine, homocitrulline, homocysteine, homocystine, homophenylalanine, homoproline, and 4-hydrazinobenzoic acid.

Amino acids are usually classified by properties of the side chain into four groups: acidic, basic, hydrophilic (polar), and hydrophobic (nonpolar). Amino acids described herein may be identified by their full names or by the corresponding standard one- or three-letter codes. Lower case single-letter codes are used to indicate D-chirality.

An "amino acid analog" is an amino acid, or a small molecule mimetic of an amino acid, that shares a common chemical, charge, steric, or other property of a given amino acid. For example, analogs of alanine include, e.g., β-alanine, ethylglycine, α-aminoisobutryic acid, and D-alanine; analogs of cysteine include, e.g., homocysteine, D-cysteine, and penicillamine; analogs of phenylalanine include, e.g., 3-fluorophenylalanine, 4-methylphenylalanine, phenylglycine, 1-naphthylalanine, and 3,3-diphenylalanine, 4-aminophenylalanine, pentafluorophenylalanine, 2-pyridylalanine, 3-pyridylalanine, 4-nitrophenylalanine, 2-pyrrolidinylalanine, 3-piperidylalanine, 4-piperidylalanine; and analogs of histidine include, e.g., 1-methylhistidine, 2,4-diaminobutyric acid, thiazolylalanine, 2,3-diaminopropionic acid, guanylalanine, 2-pyridylalanine, 3-pyridylalanine, 4-pyridylalanine, thienylalanine, ornithine, 4-guanylphenylalanine, and 4-aminophenylalanine.

"Amino protecting group," as used herein, refers to any substituent that may be used to prevent an amino group on a molecule from undergoing a chemical reaction while chemical change occurs elsewhere in the molecule. An amino protecting group can be removed under the appropriate chemical conditions. Numerous amino protecting groups are known to those skilled in the art, and examples of amino protecting groups, methods for their addition, and methods for their removal can be found in T. W. Green, *Protective Groups in Organic Synthesis*, John Wiley and Sons, New York, 1991; Chapter 7, M. Bodanszky, *Principles of Peptide Synthesis*, 1 st and 2nd revised ed., Springer-Verlag, New York, N.Y. (1984) and (1993), and Stewart and Young, *Solid Phase Peptide Synthesis*, 2nd ed., Pierce Chemical Co., Rockford, Ill. (1984), the disclosures of which are incorporated herein by reference. The term "protected (monosubstituted)amino" means there is an amino-protecting group on the (monosubstituted)amino nitrogen atom. In addition, the term "protected carboxamide" means there is an amino-protecting group on the carboxamide nitrogen. Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluoyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluoylsulfonyl)-ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-phenyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, α-2,4,5-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxy-carbonyl, 4-cyanobenzyloxycarbonyl, 4-(decyloxy)benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. For example, amino protecting groups may be chosen from Boc, Cbz, and Fmoc. More than one variety of amino protecting group may be employed so long as the derivatized amino group is stable to the conditions of the subsequent reaction(s) and can be removed at the appropriate point without disrupting the remainder of the compounds.

The term "aromatic," as used herein, refers to a mono-, bi-, or other multi-carbocyclic, aromatic ring system. The aromatic group may optionally be fused to one or more rings chosen from aromatics, cycloalkyls, and heterocyclyls. Aromatics can have from 5-14 ring members, such as, e.g., from 5-10 ring members. One or more hydrogen atoms may also be replaced by a substituent group selected from acyl, acylamino, acyloxy, alkenyl, alkoxy, alkyl, alkynyl, amino, aromatic, aryloxy, azido, carbamoyl, carboalkoxy, carboxy, carboxyamido, carboxyamino, cyano, cycloalkyl, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. Nonlimiting examples of aromatic groups include phenyl, naphthyl, indolyl, biphenyl, and anthracenyl.

An "aromatic amino acid," as used herein, is an amino acid having a side chain that comprises an aromatic ring structure. Aromatic amino acids include, for example, histidine, tyrosine, tryptophan, phenylalanine, 1-naphthylalanine, and 4-pyridylalanine.

"Carboxy-protecting group" refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, .beta.-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, *Protective Groups in Organic Chemistry*, J. G. W. McOmie, Ed., Plenum Press, New York, N.Y. (1973), Chapter 5, and T. W. Greene, *Protective Groups in Organic Synthesis*, 2nd ed., John Wiley and Sons, New York, N.Y. (1991), Chapter 5. A related term is "protected carboxy," which refers to a carboxy group substituted with one of the above-described carboxy-protecting groups.

"Bind," "binding," and "bound" refer to a noncovalent interaction between a polypeptide and another biologically active molecule that is dependent on the steric and chemical complementarity of the two molecules. The steric and chemical complementarity of polypeptides is determined by a specific amino acid sequence.

"Biologically active molecules" refer to peptides, nucleic acids, and/or small molecules, such as small organic or inorganic molecules as well as fragments thereof, capable of treating a disease or condition by performing a function or an action, or stimulating or responding to a function, an action or a reaction, in a biological context (e.g. in an organism, a cell, or an in vitro model thereof).

A "bridge" refers to a covalent bond between two non-adjacent amino acids, amino acid analogs, or other chemical moieties in a peptide. The bridge may be, e.g., a backbone to backbone, side chain to backbone, or side chain to side chain bridge. The bridge may be prepared by a cyclization reaction that results in the formation of a new amide, ester, ether, thioether, alkene, or disulfide bond. A backbone to backbone bridge, for example, results from the formation of a lactam at the N- and C-termini.

A "cyclic peptide" refers to a peptide having an intramolecular bond bridging two non-adjacent amino acids.

A peptide "dimer," as used herein, is a molecule comprising a first and second peptide chain that may be the same or different. The dimer may further comprise at least one optional linker to which the two peptides are covalently bound.

A "dipeptide mimetic" is substantially similar (e.g., substantially isosteric, or having a substantially similar position or orientation) to a dipeptide such as, for example, glycylglycine. The dipeptide mimetic may comprise any combination of linked molecules as long as the structural limitations listed above, are recognized. Dipeptide mimetics may have one or more peptide linkages optionally replaced by a linkage selected from, for example: —$CH_2NH$—, —$CH_2S$—, —$CH_2$—$CH_2$—, —CH=CH— (cis and trans) —$COCH_2$— $CH(OH)CH_2$—, and —$CH_2$ SO—, by methods well known in the art. The skilled artisan will recognize that dipeptide mimetics also include, for example, β-turn mimetics. See, e.g., R. M. Friedinger, *J. Med. Chem.* 46:5553-5566 (2003), and S. Hanessian, *Tetrahedron* 53:12789-12854 (1997).

Nonlimiting examples of dipeptide mimetics include:

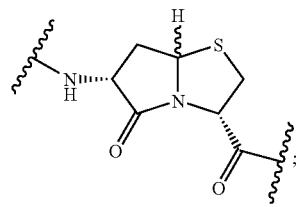

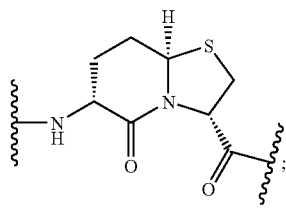

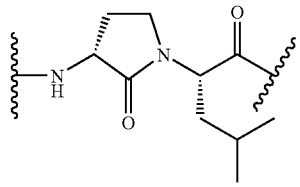

(D,L-Friedinger's lactam);

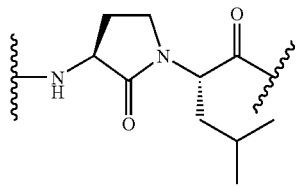

(L,L-Friedinger's lactam);
(3S)-3-amino-2-oxo-1-piperidine-acetic acid and (3R)-3-amino-2-oxo-1-piperidine-acetic acid;
(3S)-3-amino-2-oxo-1-azepine acetic acid and (3R)-3-amino-2-oxo-1-azepine acetic acid;
(3S)-3-amino-2-oxo-1-pyrrolidine acetic acid and (3R)-3-amino-2-oxo-1-pyrrolidine acetic acid;
(3R)-3-amino-1-carboxymethyl-valerolactam; and
3-amino-N-1-carboxymethyl-2,3,4,5-tetrahydro-1H-[1]-benzazepine-2-one.

The term "disulfide bridge" refers to the covalent bond formed between the sulfhydryl (i.e., thiol or mercaptan) groups of 2 amino acids (such as, e.g., cysteine, penicillamine, and homocysteine) upon oxidation. A disulfide bridge may bridge two amino acids contained in the same linear peptide, resulting in the cyclization of the linear peptide. A disulfide bridge may also be formed between two peptides, thereby producing a peptide dimer.

A "domain" is a region of a peptide or peptides having some distinctive physical feature or role including, for example, an independently folded structure composed of one section of a peptide chain. A domain may bind to another domain that is the same or different. A domain may contain the sequence of the distinctive physical feature of the peptide or it may contain a fragment of the physical feature which retains its binding characteristics (i.e., it can bind to a second domain).

"Effective dose," "effective amount," "therapeutically effective amount," and the like, refer to an amount of an agent sufficient to provide a desired physiological, pharmacological, and/or cognitive change that may vary depending on the patient, the disease, and the treatment. The amount may either be a dose for the treatment of a subject believed to have a particular disorder, in which case it should sufficiently alleviate or ameliorate the symptoms of the disorder or condition, or be a prophylacetic dose, in which case it should be sufficient to prevent, partially or completely, the appearance of symptoms in the subject.

The term "fusion," as used herein, refers to a covalent conjugate between a peptide of the invention and another molecule, which may be, e.g., a protein, a peptide, a small molecule, a polymer (e.g., polyethylene glycol or a polysaccharide), or a nucleic acid. A peptide-small molecule or peptide-polymer fusion may be prepared synthetically, whereas a peptide-protein or peptide-peptide fusion may be prepared by chemical conjugation or by expression in an appropriate host cell.

The terms "modulate," "modulating," and "modulation" refer to the increasing or decreasing of a level of an active peptide. Modulation can occur directly or indirectly.

The term "multimer," as used herein, refers to a molecule comprising multiple peptide chains, that may be the same or different. The multimer may further comprise at least one optional linker to which at least two peptides are covalently bound. A multimer may be, e.g., a dimer, trimer, or tetramer.

A linker may be, e.g., a bis-thiol linker, a tris-thiol linker, a tetrathiol linker, a dicarboxylic acid linker, a tricarboxylic acid linker, a tetracarboxylic acid linker, an amine linker, a triamine linker, or a tetraamine linker.

The term "peptide" refers to molecules comprising amino acids, including, e.g., L and D amino acids, linearly coupled through amide bonds. Peptides may additionally contain amino acid derivatives or non-amino acid moieties such as, e.g., dipeptide mimetics. A peptide of the invention may range from, e.g., 2-100, 5-30, 7-50, 10-30, or 10-50 amino acids (inclusive) in length, such as, e.g., from 11-35 amino acids. Peptides may comprise further modifications, such as, e.g., glycosylation, acetylation, phosphorylation, PEGylation, lipidation, or conjugation with an organic or inorganic molecule.

"Positively charged," as used herein, refers to an amino acid, amino acid mimetic, or chemical moiety that is positively charged at a pH greater than 6, such as, e.g., from pH 6-8, 6-9, 7-8, or 7-9. For example, positively charged amino acids include lysine, arginine, and 2,4-diaminobutyric acid.

The term "positively charged aromatic amino acid" refers to an amino acid that is positively charged at a pH greater than 6, such as, e.g., from pH 6-8, 6-9, 7-8, or 7-9. For example, positively charged aromatic amino acids include histidine, 4-aminophenylalanine, and 4-guanylphenylalanine.

An amino acid sequence that is "substantially identical" to a given sequence may be, e.g., at least 60%, 64%, 70%, 75%, 76%, 80%, 82%, 85%, 88%, 90%, 94%, 95%, 97%, 98%, or 99% identical to the given sequence. It may be derived from the given sequence by truncation, deletion, substitution, or addition of at least one amino acid, and/or may differ from a given sequence by, e.g., the addition, deletion, or substitution of at least 1, 2, 3, 4, 5, 6, 7, or 8 amino acids.

"Treat," "treatment," and "treating" refer to the reduction in severity or duration of a disease or condition; the amelioration of one or more symptoms associated with a disease or condition; the provision of beneficial effects to a subject with a disease or condition, without necessarily curing the disease or condition; or the prevention of a disease or condition.

A peptide "trimer" is a molecule comprising a first, second, and third peptide chain, that may be the same or different. A peptide trimer may further comprise at least one optional linker to which at least two of the peptides are covalently bound.

II. Peptides of the Invention

Peptides of the invention have been evaluated on the basis of relative affinity for FcRn and capacity to block the Fc portion of IgG from binding to FcRn. Peptides that demonstrate the ability to bind FcRn and/or block the binding of FcRn to the Fc portion of IgG share certain sequence commonalities or features. Thus, one embodiment of the invention provides a peptide capable of inhibiting the binding of the Fc portion of a human IgG to human Fc neonatal receptor, comprising the sequence:

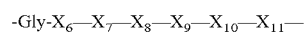

wherein:
$X_6$ is chosen from positively charged amino acids, aromatic amino acids, positively charged aromatic amino acids, and analogs thereof;
$X_7$ is chosen from phenylalanine and phenylalanine analogs;
$X_8$ and $X_9$ are each independently chosen from glycine, sarcosine, aspartic acid, D-amino acids, α-aminoisobutyric acid, and analogs thereof, or $X_8$, when taken together with $X_9$, forms a dipeptide mimetic;

$X_{10}$ is chosen from amino acids and analogs thereof, or $X_{10}$, when taken together with $X_9$, forms a dipeptide mimetic;

$X_{11}$ is chosen from tyrosine and tyrosine analogs; and

In certain embodiments, the peptide ranges from 7 to 50 amino acids in length and binds to human FcRn, preventing FcRn from binding to human IgG.

In one exemplary embodiment, a peptide of the invention comprises:

Gly-$X_6$-Phe-$X_8$—$X_9$—$X_{10}$-Tyr.

In another embodiment, peptides of the invention can be represented by the formula:

$R_1$-Gly-$X_6$—$X_7$—$X_9$—$X_{10}$—$X_{11}$—$R_2$ wherein:

$R_1$ has the formula $X_1$—$X_2$—$X_3$—$X_4$ wherein $X_1$ is chosen from hydrogen, acyl, and amino acid protecting groups;

$X_2$ is absent or is chosen from an amino acid and peptides of 2-15 amino acids in length;

$X_3$ is absent or is an amino acid that is capable of forming a bridge with $X_{10}$, $X_{12}$ or $X_{13}$, wherein the bridge is chosen from an amino terminus to carboxy terminus bridge, a side chain to backbone bridge, and a side chain to side chain bridge;

$X_4$ is absent or is chosen from an amino acid and peptides of 2-15 amino acids in length;

—$X_6$, —$X_7$, —$X_8$, —$X_9$, —$X_{10}$, and —$X_{11}$ are as defined above; and $R_2$ has the formula —$X_{12}$—$X_{13}$—$X_{14}$—$X_{15}$ wherein $X_{12}$ is absent or is an amino acid;

$X_{13}$ is absent or is an amino acid;

$X_{14}$ is absent or is chosen from an amino acid and peptides of 2-15 amino acids in length; and $X_{15}$ is an amino group or a carboxy protecting group.

The term “amino acid” as used to define the peptides of the invention includes amino acid analogs.

In one embodiment, $X_6$ is a positively charged amino acid chosen from lysine, ornithine, 2,4-diaminobutyric acid, 2,3-diaminopropionic acid, arginine, guanylalanine, and analogs thereof. In another embodiment, $X_6$ is an aromatic amino acid chosen from tyrosine, tryptophan, phenylalanine, and analogs thereof. In another embodiment, $X_6$ is a positively charged aromatic amino acid chosen from histidine, 1-methylhistidine, 2-pyridylalanine, 3-pyridylalanine, 4-pyridylalanine, 4-aminophenylalanine, 4-guanylphenylalanine, thiazolylalanine, and analogs thereof. In another embodiment, $X_6$ is 4-guanylphenylalanine. In another embodiment, $X_6$ is chosen from histidine, 3-pyridylalanine, 4-pyridylalanine, 4-guanylphenylalanine, and analogs thereof.

Exemplary histidine analogs are chosen from, but not limited to: diaminobutyric acid; thiazolylalanine; 2,3-diaminopropionic acid; guanylalanine; 2-pyridylalanine; 3-pyridylalanine; thienylalanine; ornithine; 4-guanylphenylalanine; 1-methylhistidine; 4-aminophenylalanine; 2-pyrrolidinylalanine; 3-piperdylalanine; and 4-piperidylalanine.

Exemplary phenylalanine derivatives may be chosen from, but not limited to 4-aminophenylalanine; pentafluorophenylalanine; 2-pyridylalanine; 3-pyridylalanine; 4-nitrophenylalanine; 1-napthylalanine; homophenylalanine; phenylglycine; 2-methylphenylalanine; 3-methylphenylalanine; 4-methylphenylalanine; 2-chlorophenylalanine; 3-chlorophenylalanine; 4-chlorophenylalanine; 3,3-di-phenylalanine; 4,4-bi-phenylalanine; 4-t-butylphenylalanine; cyclohexylalanine; (4-aminoacetyl)-phenylalanine; L-1,2,3,4-tetrahydroisoquinoline-3-carboxylic acid; D-betamethylphenylalanine; and L-betamethylphenylalanine.

In one embodiment, $X_{10}$ is chosen from neutral and hydrophobic amino acids, and analogs thereof.

In one embodiment, $X_2$ is chosen from an amino acid and peptides of 2 or 3 amino acids in length. In one embodiment, $X_2$ includes at least one hydrophobic amino acid. In another embodiment, $X_2$ is an amino acid or a peptide of 2-15 amino acids in length, wherein the carboxy terminal amino acid is a hydrophobic amino acid.

In one embodiment, $X_4$ is an amino acid or a peptide of 2-15 amino acids in length, wherein the carboxy terminal amino acid is N-methylated.

In one embodiment, the peptide is linear. In another embodiment, at least one of $X_{10}$, $X_{12}$, or $X_{13}$ is an amino acid that is capable of forming a bridge with $X_3$, wherein the bridge is chosen from an amino terminus to carboxy terminus bridge, a side chain to backbone bridge, and a side chain to side chain bridge. In one embodiment, the bridge is a side chain to side chain bridge, which can be a disulfide bridge, an ether bridge, a thioether bridge, an alkene bridge, or an amide bridge.

In one embodiment, the side chain to side chain bridge is a disulfide bridge between: cysteine and cysteine; cysteine and homocysteine; cysteine and penicillamine; homocysteine and homocysteine; homocysteine and penicillamine; or penicillamine and penicillamine. In another embodiment, the side chain to side chain bridge is an amide bridge between: aspartic acid and lysine; aspartic acid and ornithine; aspartic acid and 2,4-diaminobutyric acid; aspartic acid and 2,3-diaminopropionic acid; glutamic acid and lysine; glutamic acid and ornithine; glutamic acid and 2,4-diaminobutyric acid; or glutamic acid and 2,3-diaminopropionic acid.

In one embodiment, the peptide comprises at least one cysteine (e.g., at $X_3$) or cysteine analog chosen from: homocysteine, D-cysteine, and penicillamine.

In one embodiment, at least one of $X_8$ and $X_9$ is a D-amino acid or is chosen from: glycine, α-aminoisobutyric acid, and sarcosine.

In one embodiment, $X_8$, taken together with $X_9$, forms a dipeptide mimetic chosen from:

beta-alanine;

4-aminobutanoic acid;

5-aminopentanoic acid;

3-(aminomethyl)benzoic acid;

4-(aminomethyl)benzoic acid;

3-(aminophenyl)acetic acid;

4-(aminophenyl)acetic acid;

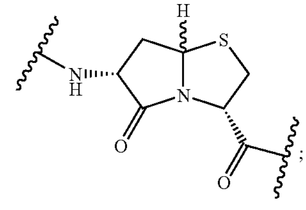

;

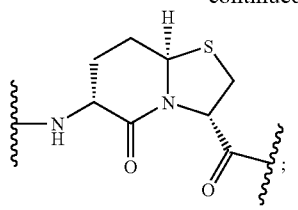

3-amino-2-oxo-1-piperidine-acetic acid;
(3S)-3-amino-2-oxo-1-piperidine-acetic acid and (3R)-3-amino-2-oxo-1-piperidine-acetic acid;
(3S)-3-amino-2-oxo-1-azepine acetic acid and (3R)-3-amino-2-oxo-1-azepine acetic acid;
(3S)-3-amino-2-oxo-1-pyrrolidine acetic acid and (3R)-3-amino-2-oxo-1-pyrrolidine acetic acid;
(3R)-3-amino-1-carboxymethyl-valerolactam; and
3-amino-N-1-carboxymethyl-2,3,4,5-tetrahydro-1H-[1]-benzazepine-2-one.

In some embodiments, the peptide comprises at least one phenylalanine phenylalanine analog chosen from: tryptophan; tyrosine; 2-aminophenylalanine; 3-aminophenylalanine; 4-aminophenylalanine; pentafluorophenylalanine; 2-pyridylalanine; 3-pyridylalanine; 4-nitrophenylalanine; 1-naphthylalanine; homophenylalanine; phenylglycine; 2-methylphenylalanine; 3-methylphenylalanine; 4-methylphenylalanine; 2-chlorophenylalanine; 3-chlorophenylalanine; 4-chlorophenylalanine; 3,3-diphenylalanine; 4,4'-biphenylalanine; 4-t-butylphenylalanine; cyclohexylalanine; (4-aminoacetyl)phenylalanine; L-1,2,3,4-tetrahydroisoquinoline-3-carboxylic acid; D-beta-methylphenylalanine; and L-beta-methylphenylalanine.

In some embodiments, the peptide comprises at least one tyrosine analog chosen from: phenylalanine; 4-aminophenylalanine; 4-methoxyphenylalanine; pentafluorophenylalanine; 2-pyridylalanine; 3-pyridylalanine; 4-pyridylalanine; 4-nitrophenylalanine; 2-nitrotyrosine; and 4-fluorophenylalanine.

In one embodiment, $X_9$ and $X_{10}$, taken together, form a dipeptide mimetic chosen from:
D,L-Friedinger's lactam

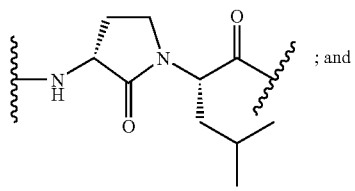
; and

L,L-Friedinger's lactam

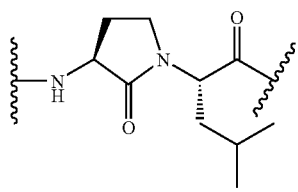

In certain embodiments, the peptide of the invention comprises at least one histidine analog chosen from: 2,4-diaminobutyric acid; thiazolylalanine; 2,3-diaminopropionic acid; guanylalanine; 2-pyridylalanine; 3-pyridylalanine; 4-pyridylalanine; thienylalanine; ornithine; lysine; arginine; 4-guanylphenylalanine; 1-methylhistidine; 3-methylhistidine; 1,3-dimethylhistidine; 4-aminophenylalanine; 2-pyrrolidinylalanine; 3-piperdylalanine; and 4-piperidylalanine.

In certain embodiments, the number of amino acids between those amino acids forming a bridge ranges from 6-12. In other embodiments, eight or nine amino acids exist between amino acids forming a bridge.

In some embodiments the peptides of the invention are at least seven and as many as 50 amino acids long. In other embodiments the peptides are from 11 and 35 amino acids in length.

In certain embodiments, the peptides of the invention exist as a multimer, such as a dimer, a trimer or a tetramer. The peptides of a multimer may be the same or different.

In one embodiment, the peptide is a dimer, such as a dimer that is the product of reductive alkylation. In another embodiment, the dimer is the product of a reaction between individual peptide monomers and a multivalent linker. In one embodiment, the multivalent linker is chosen from thiol, acid, alcohol, and amine linkers. In another embodiment, the dimer is the product of an alkylation reaction, such as, e.g., the alkylation reaction of a thiol and an alkyl halide.

In one embodiment, the peptides are synthesized on the resin, and then multimerized (e.g., dimerized) by reaction with a multivalent linker, such as, e.g., an acid or amine multivalent linker, as described in Example 15.

In some embodiments, the peptide of the invention comprise at least 2 of the modifications described above.

In certain embodiments, the peptides of the invention comprise:
a) an amino acid sequence chosen from:

```
QRFCTGHFGGLYPCNGP,        (SEQ ID NO:1)

GGGCVTGHFGGIYCNYQ,        (SEQ ID NO:2)

KIICSPGHFGGMYCQGK,        (SEQ ID NO:3)

PSYCIEGHIDGIYCFNA,        (SEQ ID NO:4)
and

NSFCRGRPGHFGGCYLF;        (SEQ ID NO:5)
and
``` b) an amino acid sequence that is substantially identically to one or more of SEQ ID NO:1, SEQ ID NO:2, SEQ ID NO:3, SEQ ID NO:4, and SEQ ID NO:5.

In some embodiments, the peptide comprises an amino acid sequence that is at least 64%, at least 70%, at least 76%, at least 82%, at least 88%, at least 94%, or 100% identical to one or more of SEQ ID NO:1, SEQ ID NO:2, SEQ ID NO:3, SEQ ID NO:4, and SEQ ID NO:5. In other embodiments, the peptide of the invention may comprise SEQ ID NO:1, SEQ ID NO:2, SEQ ID NO:3, SEQ ID NO:4, or SEQ ID NO:5 having at least one or as many as five deletion, substitution, or addition mutations. All peptides of the invention inhibit binding of human FcRn to IgG.

In some embodiments, a peptide of the invention may comprise SEQ ID NO:1, SEQ ID NO:2, SEQ ID NO:3, SEQ ID NO:4, or SEQ ID NO:5 modified by at least one conservative amino acid substitution. In certain embodiments, a peptide of the invention may comprise SEQ ID NO:1, SEQ ID NO:2, SEQ ID NO:3, SEQ ID NO:4, or SEQ ID NO:5 modified by at least one amino acid substitution, wherein the amino acid is substituted with a naturally occurring amino acid. In some embodiments, a peptide of the invention may have SEQ ID NO:1, SEQ ID NO:2, SEQ ID NO:3, SEQ ID NO:4, or SEQ ID NO:5 modified by at least one amino acid substitution, wherein the amino acid is substituted with a D-amino acid. In some embodiments, a peptide of the invention may have SEQ ID NO:1, SEQ ID NO:2, SEQ ID NO:3, SEQ ID NO:4, or SEQ ID NO:5 modified by at least one amino acid substitution, wherein the amino acid is substituted with an N-methylated amino acid. In some embodiments, a peptide of the invention may have SEQ ID NO:1, SEQ ID NO:2, SEQ ID NO:3, SEQ ID NO:4, or SEQ ID NO:5 modified by at least one amino acid substitution, wherein the amino acid is substituted with a non-naturally occurring amino acid. In certain embodiments, a peptide of the invention may have SEQ ID NO:1, SEQ ID NO:2, SEQ ID NO:3, SEQ ID NO:4, or SEQ ID NO:5 modified by at least one amino acid substitution, wherein the amino acid is substituted with an amino acid mimetic.

Alternatively, peptides of the invention may comprise an amino acid sequence chosen from Table 1 that is capable of binding to FcRn, thereby inhibiting FcRn binding to the Fc portion of an IgG molecule. The invention further includes peptides comprising a variant of the sequences listed in Table 1, wherein variants include, but are not limited to: truncations; peptides that share at least 68%, 72%, 76%, 80%, 84%, 88%, 92%, or 96%, identity with at least one of the peptides of Table 1. Variants also include peptides comprising a sequence listed in Table 1 that contains at least one amino acid substitution, wherein the amino acid is substituted with a naturally occurring amino acid, a non-naturally occurring amino acid, an amino acid analog, or an amino acid mimetic.

TABLE 1

| SEQ ID NO:6  | AGQRFCTGHFGGLYPCNGPGTGGGK |
| SEQ ID NO:7  | AGGGCVTGHFGGIYCNTQGTGGGK  |
| SEQ ID NO:8  | AGKIICSPGHFGGMYCQGKGTGGGK |
| SEQ ID NO:9  | AGPSYCIEGHIDGIYCFNAGTGGGK |
| SEQ ID NO:10 | AGNSFCRGRPGHFGGCYLFGTGGGK |

In one embodiment, peptides of the invention may comprise an amino acid sequence listed in Table 1 that has 1, 2, 3, 4, 5, 6, or more conservative amino acid substitutions. In another embodiment, peptides of the invention may comprise an amino acid sequence listed in Table 1 that has been substituted with 1, 2, 3, 4, 5, 6, or more naturally-occurring amino acids.

In some embodiments, peptides of the invention may comprise an amino acid sequence listed in Table 1 that has been substituted with 1, 2, 3, 4, 5, 6, or more non-naturally-occurring amino acids. In another embodiment, peptides of the invention may comprise an amino acid sequence listed in Table 1 that has been substituted with 1, 2, 3, 4, 5, 6, or more N-methylated amino acids. In another embodiment, peptides of the invention may comprise an amino acid sequence listed in Table 1 that has been substituted with 1, 2, 3, 4, 5, 6, or more amino acids in the D-configuration. In yet another embodiment, peptides of the invention may comprise an amino acid sequence listed in Table 1 that has been substituted with 1, 2, 3, 4, 5, 6, or more amino acid mimetics.

Exemplary embodiments of the invention are provided below. Many of these embodiments encompass the amino acid sequences listed in Table 1 modified to include one or more amino acid substitutions. While these embodiments provide examples of suitable substitutions, it should be understood that other substitutions that do not destroy the biological activity of the peptides are encompassed by the invention.

In one exemplary embodiment, a peptide of the invention comprises the amino acid sequence of SEQ ID NO:6 modified with a Cysteine to Penicillamine substitution at position 6 and a Glycine to Sarcosine substitution at position 12 (wherein the positions of the amino acids are based on the amino acid numbering in SEQ ID NO:6). In another embodiment, a peptide comprises the amino acid of SEQ ID NO:6 modified with a Cysteine to Penicillamine substitution at position 6 and a Leucine to N-methylleucine substitution at position 13.

In another embodiment, a peptide of the invention may comprise the amino acid sequence of SEQ ID NO:6 modified with a cysteine to Penicillamine substitution at position 6, substitutions of both the glycines at positions 11 and 12, respectively for a single (3R)-amino-1-carboxymethyl-2-valerolactam; and a leucine to N-methylleucine substitution at position 13.

In one embodiment, a peptide of the invention may comprise the amino acid sequence of SEQ ID NO:6 modified with a cysteine to penicillamine substitution at position 6, a glycine to sarcosine substitution at position 12 and a leucine to N-methylleucine substitution at position 13. In another embodiment, a peptide of the invention may comprise the amino acid sequence of SEQ ID NO:6 modified with a cysteine to penicillamine substitution at position 6, substitutions of both the glycines at positions 11 and 12, respectively for a single (3R)-amino-1-carboxymethylcaprolactam and a leucine to N-methylleucine substitution at position 13.

In one embodiment, a peptide of the invention may comprise the amino acid sequence of SEQ ID NO:6 modified with a cysteine to penicillamine substitution at position 6, a histidine to 3-pyridylalanine substitution at position 9, a glycine to sarcosine substitution at position 12 and a leucine to N-methylleucine at position 13. In another embodiment, a peptide of the invention may comprise the amino acid sequence of SEQ ID NO:6 modified with a cysteine to penicillamine substitution at position 6, a histidine to 4-guanylphenylalanine substitution at position 9, a glycine to sarcosine substitution at position 12 and a leucine to N-methylleucine at position 13. In yet another embodiment, a peptide of the invention may comprise the amino acid sequence of SEQ ID NO:6 modified with a cysteine to penacillamine substitution at position 6, a histidine to 4-pyridylalanine substitution at position 9, a glycine to sarcosine substitution at position 12 and a leucine to N-methylleucine at position 13.

In certain embodiments, the peptides of the invention may exist as a multimer, such as a dimer, trimer, or tetramer. The peptides of the multimer may be the same or different. The peptides can be multimerized as described above and in the ensuing Examples.

In one embodiment, the affinity of the peptides of the invention for FcRn will be represented by $K_D$ with a value ranging from 50 fM to 1 mM. In another embodiment, the affinity of the peptides of the invention will be represented by a $K_D$ with a value ranging from 50 fM to 100 µM, or a value ranging from 50 fM to 1 nM, or a value ranging from 1 pM to 1 nM. In another embodiment, a composition comprising at least one of the peptides of the invention will modulate the serum concentration of IgG. In one embodiment, the peptides of the invention can block an ing to FcRn by binding to at least one amino acid of FcRn that also specifically interacts with an IgG constant region.

III. Methods of Making the Peptides of the Invention

1. General Methods of Synthesizing Peptides of the Invention

The peptides of the invention can be synthesized using techniques well known in the art. For example, peptides of the invention that are composed entirely of naturally occurring amino acids can be synthesized recombinantly in cells using polynucleotides encoding the peptide. See, e.g., Sambrook et al., *Molecular Cloning A Laboratory Manual*, Cold Spring Harbor Laboratory, N.Y. (1989) and Ausubel et al., *Current Protocols in Molecular Biology*, Greene Publishing Associates and Wiley Interscience, N.Y. (1989). Alternatively, the peptides of the invention can be synthesized using known synthetic methods such as solid phase synthesis. Synthetic techniques are well known in the art. See e.g., Merrifield, *Chemical Polypeptides*, Katsoyannis and Panayotis eds. pp. 335-61 (1973); Merrifield, *J. Am. Chem. Soc.* 85:2149 (1963); Davis et al., *Biochem. Intl.* 10:394 (1985); Finn et al., *The Proteins* (3d ed.) 2:105 (1976); Erikson et al., *The Proteins* (3d ed.) 2:257 (1976). Standard Fmoc/tBu protocols may be used as described in W. C. Chan and P. D. White eds. *Fmoc Solid Phase Peptide Synthesis: A Practical Approach* Oxford University Press Inc. New York (2000) and U.S. Pat. No. 3,941,763. Alternatively, chimeric proteins of the invention can be synthesized using a combination of recombinant and synthetic methods. In certain applications, it may be beneficial to use either a recombinant method, a synthetic method or a combination of recombinant and synthetic methods.

2. Methods for Synthesizing Peptide Analogs of the Peptides of the Invention As used herein, the twenty conventional amino acids and their abbreviations follow conventional usage. See *Immunology—A Synthesis*, $2^{nd}$ Edition, E. S. Golub and D. R. Gren, Eds., Sinauer Associates, Sunderland, Mass. (1991). Stereoisomers (e.g., D-amino acids) of the twenty conventional amino acids, unnatural amino acids such as α-, α-di-substituted amino acids, N-alkyl amino acids, N-methyl amino acids, lactic acid, and other unconventional amino acids may also be suitable components for polypeptides of the present invention. Examples of unconventional amino acids include: aminoisobutyric acid, 3-amino-1-carboxymethylvalerolactam, 4-guanyl-phenylalanine, 5-aminopentanoic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, penicillamine, sarcosine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.* 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in binding to a specific protein target.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar peptides that are important for activity or structure. In view of such a comparison, one can predict the importance of amino acid residues in a peptide that correspond to amino acid residues which are important for activity or structure in similar peptides. One skilled in the art may opt for chemically similar amino acid substitutions for such predicted important amino acid residues.

One skilled in the art can also analyze the three-dimensional structure and amino acid sequence in relation to that structure in similar peptides. One skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

According to certain embodiments, amino acid substitutions may be those which: (1) reduce susceptibility to proteolysis, (2) reduce susceptibility to oxidation, (3) alter binding affinities associated with the biological function, and/or (4) confer or modify other physicochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, Creighton, Ed., W.H. Freeman and Company, New York (1984); *Introduction to Protein Structure*, C. Branden and J. Tooze, eds., Garland Publishing, New York, N.Y. (1991); and Thornton et al., *Nature* 354:105 (1991).

In certain embodiments, amino acid derivatives comprise covalent modifications, including, but not limited to, chemical bonding with polymers, lipids, or other organic or inorganic moieties. In certain embodiments, a chemically modified specific binding agent may have greater circulating half-life than a specific binding agent that is not chemically modified. In certain embodiments, a chemically modified specific binding agent may have improved targeting capacity for desired cells, tissues, and/or organs. In certain embodiments, a derivative specific binding agent is covalently modified to include one or more water soluble polymer attachments, including, but not limited to, polyethylene glycol, polyoxyethylene glycol, or polypropylene glycol. See, e.g., U.S. Pat. Nos. 4,640,835; 4,496,689; 4,301,144; 4,670,417; 4,791,192; and 4,179,337. In certain embodiments, a derivative specific binding agent comprises one or more polymers, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

3. Methods for Synthesizing Analogs of the Peptides of the Invention

Peptide analogs are commonly used in the pharmaceutical industry as non-peptide drugs with properties analogous to those of the template peptide. These types of non-peptide compounds are termed "peptide mimetics" or "peptidomimetics." Fauchere, *J. Adv. Drug Res.* 15:29 (1986); Veber and Freidinger, *TINS* p. 392 (1985); and Evans et al., *J. Med. Chem.* 30:1229 (1987), which are incorporated herein by reference. Such compounds are often developed with the aid of computerized molecular modeling. Peptide mimetics that are structurally similar to therapeutically useful peptides may be used to produce a similar therapeutic or prophylacetic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference), such as, for example, by adding internal cysteine residues capable of forming intramolecular disulfide bridges which cyclize the peptide.

Peptide dimerization or oligomerization can enhance the avidity of a peptide sequence for a given receptor. See, for example, Johnson, et. al., *Chem. Biol.* 12:939 (1997). It is envisioned that dimers and higher order multimers of the peptides of the invention could be synthesized using a variety of methods well known in the art. The dimers or multimers could be synthesized directly on an automated peptide synthesizer as a continuous peptide sequence. Alternatively, peptide multimers could be synthesized by reacting individual peptide monomers with a multivalent linker moiety. See, e.g., Rose, *J. Am. Chem. Soc.* 116:30 (1994). As another example, peptide multimers may be synthesized by incorporating branched linker groups prior to the synthesis of the peptide sequence as in the synthesis of "multiple antigenic peptides" (MAP). D. Posnett et. al., *J. Biol. Chem.* 263:1719 (1988). The invention provides a novel method for forming these peptide dimers involves reacting the N-termini of the peptides, while on resin, with a linker molecule, such as, for example, succinic acid, so that adjacent peptides on the solid phase resin bead will react with each other and form a dimer joined by the peptides N-termini. Subsequent cleavage from the resin provides an N-terminally linked peptide dimer.

4. Construction of Expression Vectors for the Expression of Peptides of the Invention Nucleic acids encoding peptides of the invention may be synthesized by standard methods known in the art, e.g., by use of an automated DNA synthesizer (such as are commercially available from Biosearch, Applied Biosystems, etc.). Additional methods of nucleic acid synthesis are known in the art. See, e.g., U.S. Pat. Nos. 6,015,881; 6,281,331; 6,469,136. For recombinant production of peptides of the invention, polynucleotide sequences encoding the peptides are inserted into appropriate expression vehicles, i.e. vectors which contains the necessary elements for the transcription and translation of the inserted coding sequence, or in the case of an RNA viral vector, the necessary elements for replication and translation. The nucleic acids encoding the peptides of the invention are inserted into the vectors in the proper reading frame.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the DHFR gene or DHFR cDNA. Simonsen and Levinson, *Proc. Natl. Acad. Sci. USA* 80:2495 (1983). Selectable markers are reviewed by Thilly (*Mammalian Cell Technology*, Butterworth Publishers, Stoneham, Mass. (1986)) and the choice of selectable markers is well within the level of ordinary skill in the art. Selectable markers may also be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a bicistronic message. Constructs of this type are known in the art (for example, U.S. Pat. No. 4,713,339).

Expression elements in an expression systems vary in their strength and specificities. Depending on the host/vector system utilized, any of a number of suitable transcription and translation elements, including constitutive and inducible promoters, may be used in an expression vector. For example, when cloning in bacterial systems, inducible promoters such as pL of bacteriophage λ, plac, ptrp, ptac (ptrp-lac hybrid promoter), and the like may be used; when cloning in insect cell systems, promoters such as the baculovirus polyhedron promoter may be used; when cloning in plant cell systems, promoters derived from the genome of plant cells (e.g. heat shock promoters; the promoter for the small subunit of RUBISCO; the promoter for the chlorophyll a/b binding protein) or from plant viruses (e.g. the 35S RNA promoter of CaMV; the coat protein promoter of TMV) may be used; when cloning in mammalian cell systems, promoters derived from the genome of mammalian cells (e.g. metallothionein promoter) or from mammalian viruses (e.g. the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding linear or non-cyclized forms of the chimeric proteins of the invention may be driven by any of a number of promoters. For example, viral promoters such as the 35S RNA and 19S RNA promoters of CaMV (Brisson et al., *Nature* 310:511-514 (1984)), or the coat protein promoter of TMV (Takamatsu et al., *EMBO J.* 6:307-311 (1987)) may be used; alternatively, plant promoters such as the small subunit of RUBISCO (Coruzzi et al., *EMBO J.* 3:1671-1680 (1984); Broglie et al., *Science* 224:838-843 (1984)) or heat shock promoters, e.g., soybean hsp17,5-E or hsp17,3-B (Gurley et al., *Mol. Cell. Biol.* 6:559-565 (1986)) may be used. These constructs can be introduced into plant cells using Ti plasmids, Ri plasmids, plant virus vectors, direct DNA transformation, microinjection, electroporation, etc. Weissbach & Weissbach, *Methods for Plant Molecular Biology*, Academic Press, NY, Section VIII, pp. 421-463 (1988) and Grierson & Corey, *Plant Molecular Biology*, 2d Ed., Blackie, London, Ch. 7-9 (1988).

In one insect expression system that may be used to produce the chimeric proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an AcNPV promoter (for example, the polyhedron promoter). Successful insertion of a coding sequence will result in inactivation of the polyhedron gene and production of non-occluded recombinant virus (i.e. virus lacking the proteinaceous coat coded for by the polyhedron gene). These recombinant viruses are then used to infect *Spodoptera frugiperda* cells in which the inserted gene is expressed. (see, e.g., Smith et al., *J. Virol.* 46:584 (1983); U.S. Pat. No. 4,215,051). Further examples of this expression system may be found in Ausubel et al., eds., *Current Protocols in Molecular Biology*, Vol. 2, Greene Publish. Assoc. & Wiley Interscience (1989).

Another system which can be used to express the peptides of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing peptide in infected hosts. See e.g., Logan & Shenk, *Proc. Natl. Acad. Sci. USA* 81:3655 (1984). The vaccinia 7.5 K promoter may also be used. See e.g., Mackett et al., *Proc. Natl. Acad. Sci. USA* 79:7415 (1982); Mackett et al., *J. Virol.* 49:857 (1984); Panicali et al., *Proc. Natl. Acad. Sci. USA* 79:4927 (1982).

5. Expression of Peptides of the Invention in the Appropriate Target Cell

Expression vehicles may be transfected or co-transfected into a suitable target cell, to express the polypeptides of the invention. Transfection techniques known in the art include, but are not limited to, calcium phosphate precipitation (Wigler et al., *Cell* 14:725 (1978)), electroporation (Neumann et al., *EMBO, J.* 1:841 (1982)), and liposome based reagents. A variety of host-expression vector systems may be utilized to express the chimeric proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g. baculovirus) containing an appropriate coding sequence; plant cell systems infected with recombinant virus expression vectors (e.g. cauliflower mosaic virus or tobacco mosaic virus) or transformed with recombinant plasmid expression vectors (e.g. Ti plasmid) containing an appropriate coding sequence; or animal cell systems, including mammalian cells (e.g., CHO, Cos, HeLa cells).

6. Methods for Synthesizing Fusion Molecules that Comprise a Peptide of the Invention.

In some embodiments, peptides of the invention exist as a fusion protein comprising the peptide of the invention and a fusion partner. In one embodiment, the fusion partner confers properties, such as one or more of extended half-life, stability, enhanced transport to the peptide of the invention, and/or can enhance efficacy in vivo or in vitro.

Additionally, heterologous polypeptides of the present invention can be combined with parts of the constant domain of immunoglobulins (IgG), resulting in chimeric polypeptides. These particular fusion molecules facilitate purification and show an increased half-life in vivo. This has been shown, for example, in chimeric proteins consisting of the first two domains of the human CD4-polypeptide and various domains of the constant regions of the heavy or light chains of mammalian immunoglobulins. EP 0 394 827; Traunecker et al., *Nature*, 331:84-86 (1988). Fusion molecules that have a disulfide-linked dimeric structure due to the IgG part can in some instances be more efficient in binding and neutralizing other molecules than, for example, a monomeric polypeptide or polypeptide fragment alone. See, for example, Fountoulakis et al., *J. Biochem.* 270:3958-3964 (1995).

The invention also provides a polynucleotide encoding the fusion molecule of any of the peptides described above. This polynucleotide may be part of a vector that also comprises a regulatory sequence for transcribing the polynucleotide. The invention further provides a host cell comprising any of the fusion molecules described above, a polynucleotide encoding the fusion molecule of any of these peptides, or a vector that comprises a polynucleotide encoding the fusion molecule of any of these peptides and a regulatory sequence for transcription of the polynucleotide. The invention yet further provides a composition comprising any of the fusion molecules or nucleotides described above, and/or any of the vectors or host cells described above, and a buffer or a pharmaceutically acceptable carrier.

a. Fusions Comprising Antibody Fc Domains

In one embodiment, a peptide of the invention can be conjugated with the Fc domain of IgG to increase its circulation half-life. In certain embodiments, the peptides are covalently linked to the Fc domain. Methods of making chimeric proteins comprising a Fc immunoglobulin domain both recombinantly and semi-synthetically are well-known to one skilled in the art For example, an aldehyde may be incorporated into the peptide derivative, and reacted with the Fc protein using a reductive alkylation reaction which is selective for the N-terminus of Fc. Kinstler, *Adv. Drug Del. Rev.* 54:477 (2002). Alternatively, a peptide thioester may be reacted with Fc bearing an N-terminal cysteine residue Dawson and Kent, *Ann. Rev. Biochem.* 69:923 (2000).

Such peptide-Fc fusion derivatives may have an increased ability to block the IgG-FcRn interaction due to the addition of two more binding sites for FcRn through the Fc domain. Such peptide-Fc fusions may also protect the peptide from degradation and thus enhance the in vivo efficacy of the peptide. Fusion proteins that have a disulfide-linked dimeric structure due to the IgG portion can also be more efficient in binding and neutralizing other molecules than the peptide of the invention, for example, as described by Fountoulakis et al., *J. Biochem.*, 270:3958-3964 (1995).

In embodiments where the peptide of the invention is part of a fusion protein with a IgG Fc domain, the human Ig Fc may comprise a hinge, CH2, and CH3 domains of human IgG, such as human IgG1, IgG2, and IgG4. The invention also provides a fusion molecule comprising a peptide of the invention and a variant Fc polypeptide or a fragment of a variant Fc polypeptide, wherein the variant Fc comprises a hinge, CH2, and CH3 domains of human IgG2 with a Pro331Ser mutation, as described in U.S. Pat. No. 6,900,292.

Suitable Fc domains for conjugating with peptides of the invention include those having mutated amino acids at selected positions of the Fc region to attenuate its effector functions (including antibody-dependent cell cytotoxicity and complement dependent cytotoxicity). For example, an $Fc_{\gamma 2}$ variant with the Pro331 Ser mutation has less complement activity than natural $Fc_{\gamma 2}$ and does not bind to the $Fc_\gamma R$. IgG4 Fc is deficient in activating the complement cascade, and its binding affinity to $Fc_\gamma R$ is about an order of magnitude lower than that of the most active isotype, IgG1. In one embodiment, a peptide of the invention is conjugated to an $Fc_{\gamma 4}$ variant with Leu235Ala mutation which exhibits minimal effector functions as compared to the natural $Fc_{\gamma 4}$. In another embodiment, the peptide of the invention is conjugated to an $Fc_{\gamma 1}$ variant with Leu234Val, Leu235Ala and Pro331 Ser mutations which also exhibit less effector function than natural $Fc_{\gamma 1}$.

b. Fusions Comprising Albumin

In certain embodiments, the peptides of the invention can be conjugated to albumin-binding moieties. Such albumin-binding moiety-peptide conjugates may have longer in vivo half-lives and may thus require a lower peptide doses to achieve the desired therapeutic effect. Chuang et al., *Pharm. Res.* 19:569 (2002); U.S. Pat. No. 6,685,179. Thus, one embodiment of the invention provides a fusion molecule comprising the peptide of the invention with an albumin fusion partner comprising albumin, one or more fragments of albumin, a peptide that binds albumin, and/or a molecule that conjugates with a lipid or other molecule that binds albumin.

Methods of making fusion proteins comprising albumin are known in the art. For example, peptides modified by hydrophobic aromatic capping reagents have been shown to bind albumin non-covalently and extend the half-lives of peptides in rabbits. Zobel et. al., *Bioorg. Med. Chem. Lett.* 13:1513 (2003). As another example, peptides modified with thiol reactive groups have been shown to bind covalently to a single free cysteine residue on serum albumin. Kim et. al., *Diabetes* 52:751 (2003).

c. Fusions with Pegylated Moieties

In one embodiment, the peptide of the invention may be pegylated to include mono- or poly-(e.g., 2-4) PEG moieties. Pegylation may be carried out by any of the pegylation reactions known in the art. Methods for preparing a pegylated protein product will generally include (a) reacting a polypeptide with polyethylene glycol (such as a reactive ester or aldehyde derivative of PEG) under conditions whereby the peptide of the invention becomes attached to one or more PEG groups; and (b) obtaining the reaction product(s). In general, the optimal reaction conditions for the reactions will be determined case by case based on known parameters and the desired result.

There are a number of PEG attachment methods available to those skilled in the art and described in, for example, EP 0 401 384; Malik et al., *Exp. Hematol.*, 20:1028-1035 (1992); Francis, *Focus on Growth Factors*, 3 (2):4-10 (1992); EP 0 154 316; EP 0 401 384; WO 92/16221; and WO 95/34326. For example, the step of pegylating peptides of the invention may be carried out via an acylation reaction or an alkylation reaction with a reactive polyethylene glycol molecule.

Thus, peptides of the invention include pegylated peptides wherein one or more PEG groups are attached via acyl or alkyl groups. Such peptides may be mono-pegylated or poly-pegylated (for example, those containing 2-6 or 2-5 PEG groups). The PEG groups are generally attached to the peptide at the α- or ε-amino groups of amino acids, but it is also contemplated that the PEG groups could be attached to any amino group of the peptide that is sufficiently reactive to become attached to a PEG group under suitable reaction conditions.

Pegylation by acylation generally involves reacting an active ester derivative of polyethylene glycol (PEG) with a peptide of the invention. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between a peptide of the invention and a polymer such as PEG: amide, carbamate, urethane, and the like. See, e.g., Chamow, *Bioconjugate Chem.*, 5:133-140 (1994). Reaction conditions may be selected from any of those known in the pegylation art or those subsequently developed, but should avoid conditions such as temperature, solvent, and pH that would inactivate the peptide of the invention.

Pegylation by acylation will generally result in a polypegylated peptide of the invention. The connecting linkage may be an amide. The resulting product may be substantially only (e.g., >95%) mono, di- or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography and electrophoresis.

Pegylation by alkylation involves reacting a terminal aldehyde derivative of PEG with a peptide of the invention in the presence of a reducing agent. For the reductive alkylation reaction, the polymers) selected should have a single reactive aldehyde group. An exemplary reactive PEG aldehyde is polyethylene glycol propionaldehyde, which is water stable, or mono C1-C10 alkoxy or aryloxy derivatives thereof. See, for example, U.S. Pat. No. 5,252,714.

7. Purification of Biologically Expressed Peptides of the Invention

Depending on the expression system used, the expressed peptide of the invention is then isolated by procedures well-established in the art (e.g., affinity chromatography, size exclusion chromatography, ion exchange chromatography).

The expression vectors can encode for tags that permit for easy purification of the recombinantly produced chimeric protein. Examples include, but are not limited to vector pUR278 (Ruther et al., *EMBO J.* 2:1791 (1983)) in which DNA encoding a peptide of the invention is ligated into the vector in frame with the lac z coding region so that a hybrid protein is produced; pGEX vectors may be used to express chimeric proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PreScission Protease™ (Pharmacia, Peapack, N.J.) for easy removal of the tag after purification.

To increase efficiency of production, the polynucleotides can be designed to encode multiple units of the peptides of the invention separated by enzymatic cleavage sites. The resulting polypeptide can be cleaved (e.g., by treatment with the appropriate enzyme) in order to recover the peptide units. This can increase the yield of peptides driven by a single promoter. When used in appropriate viral expression systems, the translation of each peptide of the invention encoded by the mRNA is directed internally in the transcript, e.g., by an internal ribosome entry site, IRES. Thus, the polycistronic construct directs the transcription of a single, large polycistronic mRNA which, in turn, directs the translation of multiple individual polypeptides. This approach eliminates the production and enzymatic processing of polyproteins and may significantly increase yield of the peptides of the invention driven by a single promoter.

Host cells containing DNA constructs encoding the peptides of the invention may be grown in an appropriate growth medium, i.e., a medium containing nutrients required for the growth of cells. Nutrients required for cell growth may include a carbon source, a nitrogen source, essential amino acids, vitamins, minerals and growth factors. Optionally the media can contain bovine calf serum or fetal calf serum. In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g. MEM, DMEM). Selection of a medium appropriate for the particular cell line used is within the level of ordinary skill in the art.

The peptides of the invention can be produced in a transgenic animal, such as a rodent, cow, pig, sheep, goat or other non-human animals that have incorporated a foreign gene into their genome. Because this gene is present in germlne tissues, it is passed from parent to offspring. Exogenous genes are introduced into single-celled embryos (Brinster et al., *Proc. Natl. Acad. Sci. USA* 82:4438, 1985). Methods of producing transgenic animals are known in the art, including transgenics that produce immunoglobulin molecules. Wagner et al., *Proc. Natl. Acad. Sci. USA* 78:6376 (1981); McKnight et al., *Cell* 34:335 (1983); Brinster et al., *Nature* 306:332 (1983); Ritchie et al., *Nature* 312:517 (1984); Baldassarre et al., *Theriogenology* 59:831 (2003); Robl et al., *Theriogenology* 59:107 (2003); Malassagne et al., *Xenotransplantation* 10(3):267 (2003).

8. Methods for Screening and Discovering Peptides that Bind FcRn and Block the FcRn-IgG Interaction Peptides binding to FcRn may be identified using phage display libraries. Phage display libraries may be readily generated as described in Smith and Petrenko, *Chem. Rev.* 87:391 (1997). Alternatively, phage display libraries may be acquired from a commercial source, such as, e.g., Dyax Corp. (Cambridge, Mass.). Depending on the screening conditions, phage may be identified with a variety of different properties. To identify peptides that bind to FcRn (and thus compete with IgG for FcRn binding), a phage library may be screened for binding to FcRn and by competition with IgG. Optionally, peptides that bind to alternate receptors may be eliminated from the library by incubating the phage library with one or more alternate receptors. Thus, phage that bound the alternate receptor(s) would be depleted from the desired pool of phage. By sequencing the DNA of phage clones capable of binding to FcRn, peptides capable of binding to FcRn and inhibiting IgG-FcRn binding may be identified.

Examples of other methods to identify FcRn-binding peptides include: mRNA display (Roberts and Szostak, *Proc. Nat. Acad. Sci. USA* 94:12297 (1997), cell-based display (Boder and Wittrup, *Nat. Biotechnol.* 15:553 (1997), and synthetic peptide libraries (Lam, *Nature* 354:82 (1991); Houghten et. al., *Nature* 354:84 (1991)).

9. Methods for Assaying Peptides that Bind to FcRn and Block the IgG:FcRn Interaction A number of methods may be used to assess the ability of a peptide or peptidomimetic to bind FcRn and block the FcRn:IgG interaction. For example, surface plasmon resonance (SPR) is a method well known in the art to evaluate binding events (Biacore AB, Uppsala, Sweden). Using this method, one of the binding partners (FcRn or IgG) is immobilized on the SPR sensor chip and while the other binding partner is passed over the chip, which is monitored for a resulting signal. In the same experiment, the peptide to be evaluated as a competitor of the interaction between IgG and FcRn is passed over the chip. Any decrease in signal may be interpreted as a measure of the peptide's ability to block the interaction between FcRn and IgG.

Other methods for assaying for possible peptide inhibitors of the IgG:FcRn interaction are also well known in the art. One such method is an IgG competition assay in a 96-well plate format. In this example assay, soluble human FcRn on a 96-well plate is exposed to IgG and a test peptide. Residual bound IgG, as detected by an anti-IgG antibody and standard ELISA visualization reagents, provide a measure of the peptide's ability to block the FcRn-IgG interaction.

The ability of a peptide to block IgG-FcRn binding may also be carried out on cells transfected with DNA encoding a human FcRn to develop a cell line capable of expressing human FcRn on its cell surface. A binding competition assay may be applied where peptide inhibitors of IgG-FcRn binding compete with a fluorescently labeled IgG molecule. The level of residual IgG bound to the cells may be measured using, e.g., a standard fluorescent activated cell sorter (FACS).

d. Uses of the Peptides of the Invention

The peptides of the invention bind FcRn and inhibit the Fc portion of the IgG constant region from binding to FcRn resulting in increased catabolism of IgG in comparison to the catabolism of IgG in the absence of peptides of the invention. In exemplary embodiments, the IgG constant region is from the IgG1, IgG2, IgG3, or IgG4 subclasses. In particular embodiments, the IgG constant region is from IgG1, IgG2, or IgG4 subclasses. The peptides of the invention are therefore useful to treat any disease or condition, where increased catabolism of IgG is desirable. For example, peptides of the invention can be used to treat an autoimmune disease, an inflammatory disorder, cardiovascular disease with an inflammation-based etiology (e.g. arterial sclerosis), transplant rejection, and/or graft versus host disease (GVHD). The peptides of the invention can also be used to detect FcRn in a patient or a biological sample (e.g. a bodily fluid, a tissue or cell sample, cell culture supernatant). The peptides of the invention can also be used to purify FcRn from a biological sample (e.g. a bodily fluid, a tissue or cell sample, cell culture supernatant).

Thus, the invention provides a method of regulating a disease state characterized by inappropriately expressed IgG antibodies or undesired amounts or levels of IgG, comprising administering a therapeutically effective amount of a peptide of the invention. In one embodiment, the disease state is chosen from inflammatory diseases, autoimmune diseases, and cancer. In other embodiments, the invention provides methods for regulating a disease state by modulating the serum concentration of IgG. In certain embodiments, the methods of the invention may be employed to treat, prevent, or regulate an immune reaction to a therapeutic protein, such as, e.g., a erythropoietin, a lysosomal storage enzyme, or a clotting factor, such as, e.g., fibrinogen, prothrombin, factor V, factor VII, factor VIII, factor IX, factor X, factor XI, factor XII, factor XIII, or von Willebrand's factor. In other embodiments, the methods of the invention may be employed to treat, prevent, or regulate an immune reaction to a gene therapy vector.

1. Autoimmune Diseases

The peptides of the invention can be used to treat autoimmune diseases including, but not limited to Alopecia Areata, Ankylosing Spondylitis, Antiphospholipid Syndrome, Autoimmune Addison's Disease, Autoimmune Hemolytic Anemia, Autoimmune Hepatitis, Autoimmune Lymphoproliferative Syndrome (ALPS), Autoimmune Thrombocytopenic Purpura (ATP), Behcet's Disease, Bullous Pemphigoid, Cardiomyopathy, Celiac Sprue-Dermatitis Herpetiformis, Chronic Fatigue Immune Dysfunction Syndrome (CFIDS), Chronic Inflammatory Demyelinating Polyneuropathy, Cicatricial Pemphigoid, CREST Syndrome, Cold Agglutinin Disease, Crohn's Disease, Degos' Disease, Dermatomyositis, Dermatomyositis-Juvenile, Discoid Lupus, Essential Mixed Cryoglobulinemia, Fibromyalgia-Fibromyositis, Graves' Disease, Guillain-Barré Hashimoto's Thyroiditis, Idiopathic Pulmonary Fibrosis, Idiopathic Thrombocytopenia Purpura (ITP), IgA Nephropathy, Insulin dependent Diabetes, Juvenile Arthritis, Lichen Planus, Lupus, Ménière's Disease, Mixed Connective Tissue Disease, Multiple Sclerosis, Myasthenia Gravis (MG), Pemphigus, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Transplant Rejection, Ulcerative Colitis Uveitis, Vasculitis, Vitiligo, and Wegener's Granulomatosis.

In one embodiment, the autoimmune disease is chosen from bullous pemphigoid, idiopathic thrombocytopenia purpura (ITP), myasthenia gravis (MG), pemphigus (e.g., pemphigus vulgaris), and transplant rejection.

In another embodiment, the peptides of the invention may be used in combination with steroids for immunosuppression.

2. Inflammatory Disorders

The peptides of the invention can be used to treat inflammatory disorders including, but not limited to, asthma, ulcerative colitis and inflammatory bowel syndrome allergy, including allergic rhinitis/sinusitis, skin allergies (urticaria/hives, angioedema, atopic dermatitis), food allergies, drug allergies, insect allergies, mastocytosis, arthritis, including osteoarthritis, rheumatoid arthritis, and spondyloarthropathies.

3. Diseases or Conditions Requiring Administration of a Therapeutic Protein

Frequently, in diseases or conditions requiring administration of a therapeutic protein, the subject will develop antibodies against the therapeutic protein, which, in turn, prevent the therapeutic protein from be available for its intended therapeutic purpose. Accordingly, the peptides of the invention can be used in combination with the therapeutic protein to enhance the benefit of the therapeutic protein by reducing the levels of IgG; wherein, IgG antibodies are responsible for the decreased bioavailability of a therapeutic protein.

Accordingly, one embodiment provides a method of regulating, treating, or preventing a condition, disease, or disorder resulting from an immune response to a clotting factor comprising contacting a cell with a therapeutically effective amount of any of the peptides disclosed herein, wherein the clotting factor is chosen from fibrinogen, prothrombin, factor V, factor VII, factor VIII, factor IX, factor X, factor XI, factor XII, factor XIII, or von Willebrand's factor. This method may be used to regulate or treat, or prevent an immune response to a clotting factor in a patient suffering, e.g., from hemophilia A or hemophilia B. In one embodiment, peptides of the present invention block factor VIII inhibitors. In another embodiment, the method may be used to regulate or treat, or prevent an immune response to, e.g., therapeutic erythropoietin in a patient suffering from pure red cell aplasia (PRCA).

4. Diseases or Conditions Requiring Gene Therapy

Obstacles to the successful implementation of gene therapy for the treatment of a disease or condition also include the development of antibodies specific to the therapeutic protein encoded by the transgene as well as possibly to the vector used to deliver the transgene. Accordingly, the peptide of the invention can be administered in combination with gene therapy to enhance the benefit of the encoded therapeutic protein by reducing the levels of IgG. These methods are particularly useful in situations where IgG antibodies are responsible for the decreased bioavailability of a gene therapy vector or the encoded therapeutic protein. The gene therapy vector may be, e.g., a viral vector such as adenovirus and adeno associated virus. Diseases that can be treated using gene therapy include, but are not limited to, cystic fibrosis, hemophilia, PRCA, muscular dystrophy, or lysosomal storage diseases, such as, e.g., Gaucher's disease and Fabry's disease.

5. In Vivo Imaging and Detection of FcRn

The peptides of the invention can also be used in assays to detect FcRn. In some embodiments, the assay is a binding assay that detects binding of a peptide of the invention with FcRn. In these assays, either FcRn or the peptides of the invention may be immobilized, while the other (either FcRn or the peptides of the invention) is passed over the immobilized binding partner. Either FcRn or the peptides of the invention may be detectably labeled. Suitable labels include radioisotopes, including, but not limited to $^{64}$Cu, $^{67}$Cu, $^{90}$Y, $^{111}$In, $^{124}$I, $^{125}$I, $^{131}$I, $^{137}$Cs, $^{186}$Re, $^{211}$At, $^{212}$Bi, $^{213}$Bi, $^{223}$Ra, $^{241}$Am, $^{244}$Cm and 99 mTc-MDP; enzymes having detectable products (for example, luciferase, peroxidase, alkaline phosphatase, β-galactosidase, and the like); fluorescers and fluorescent labels; for example, fluorescein isothiocyanate, rhodamine, phycoerythrin, phycocyanin, allophycocyanin, o-phthaldehyde and fluorescamine; fluorescence emitting metals, for example, $^{152}$Eu, or others of the lanthanide series, attached to the peptides of the invention through metal chelating groups such as EDTA; chemiluminescent compounds, for example, luminol, isoluminol, theromatic acridinium ester, acridinium salts, imidazole, and oxalate esteror; and bioluminescent compounds, for example, luciferin, or aequorin (green fluorescent protein), specific binding molecules, for example, magnetic particles, microspheres, nanospheres, luminescent quantum dot nanocrystals, and the like.

Alternatively, specific-binding pairs may be used, involving, for example, a second stage antibody or reagent that is detectably labeled and that can amplify the signal. For example, the peptides of the invention can be conjugated to biotin, and horseradish peroxidase-conjugated streptavidin added as a second stage reagent. Digoxin and antidigoxin provide another suitable binding pair. In other embodiments, a second stage antibody can be conjugated to an enzyme such as peroxidase in combination with a substrate that undergoes a color change in the presence of the peroxidase. The absence or presence of binding between peptides of the invention and FcRn can be determined by various methods, including flow cytometry of dissociated cells, microscopy, radiography, fluorimetry, chromogenic detection, phosphor imaging, detection of chemiluminescence on film and scintillation counting. Such reagents and their methods of use are well known in the art.

For in vivo diagnostic applications, specific tissues or even specific cellular disorders that may be characterized, at least in part, by expression of FcRn, may be imaged by administration of a sufficient amount of a labeled peptide of the invention.

A wide variety of metal ions suitable for in vivo tissue imaging have been tested and utilized clinically. For imaging with radioisotopes, the following characteristics are generally desirable: (a) low radiation dose to the patient; (b) high photon yield which permits a nuclear medicine procedure to be performed in a short time period; (c) ability to be produced in sufficient quantities; (d) acceptable cost; (e) simple preparation for administration; and (f) no requirement that the patient be sequestered subsequently. These characteristics generally translate into the following: (a) the radiation exposure to the most critical organ is less than 5 rad; (b) a single image can be obtained within several hours after infusion; (c) the radioisotope does not decay by emission of a particle; (d) the isotope can be readily detected; and (e) the half-life is less than four days (Lamb and Kramer, "Commercial Production of Radioisotopes for Nuclear Medicine", *In Radiotracers For Medical Applications*, Vol. 1, Rayudu (Ed.), CRC Press, Inc., Boca Raton, pp. 17-62). In one embodiment, the metal is technetium-99m.

Accordingly, the invention provides a method of obtaining an image of an internal region of a subject which comprises administering to a subject an effective amount of a composition comprising at least one of the peptides of the invention containing a metal in which the metal is radioactive, and recording the scintigraphic image obtained from the decay of the radioactive metal. Likewise, the invention provides methods for enhancing an magnetic resonance (MR) image of an internal region of a subject which comprises administering to a subject an effective amount of a composition comprising at least one of the peptides of the invention containing a metal in which the metal is paramagnetic, and recording the MR image of an internal region of the subject.

Other methods provided by this invention include a method of enhancing a sonographic image of an internal region of a subject comprising administering to a subject an effective amount of a composition comprising at least one of the peptides of the invention containing a metal and recording the sonographic image of an internal region of the subject. In this application, the metal may be any non-toxic heavy metal ion. A method of enhancing an X-ray image of an internal region of a subject is also provided which comprises administering to a subject a peptide composition containing a metal, and recording the X-ray image of an internal region of the subject. A radioactive, non-toxic heavy metal ion may be used.

Peptides of the invention may be linked to chelators such as those described in U.S. Pat. No. 5,326,856. The peptide-chelator complex may then be radiolabeled to provide an imaging agent for diagnosis or treatment of diseases or conditions involving the regulation of IgG levels. The peptides of the invention may also be used in the methods that are disclosed in U.S. Pat. No. 5,449,761 for creating a radiolabeled peptide for use in imaging or radiotherapy.

6. Dosing and Treatment Modalities

The peptides of the invention can be administered intravenously, subcutaneously, intra-muscularly, orally, sublingually, buccally, sublingually, nasally, rectally, vaginally or via pulmonary route. The peptides of the invention can be implanted within or linked to a biopolymer solid support that allows for the slow release of the chimeric protein to the desired site.

The dose of the peptide of the invention will vary depending on the disease or condition to be treated, the severity of the disease or conditions, the subject, including their gender, age, weight and desired outcome and upon the particular route of administration used. Dosages can range from 0.1 to 100,000 µg/kg body weight. In one embodiment, the dosing range is 1-10,000 µg/kg. In another embodiment, the dosing range is 10-1,000 µg/kg. In another embodiment, the dosing range is 100-500 µg/kg. The peptide of the invention can be administered continuously or at specific timed intervals. In vitro assays may be employed to determine optimal dose ranges and/or schedules for administration. Other effective dosages can be readily determined by one of ordinary skill in the art through routine trials establishing dose response curves, for example, the amount of the peptides of the invention necessary to increase or decrease the level of IgG can be calculated from in vivo experimentation. Those of skill will readily appreciate that dose levels can vary as a function of the specific compound, the severity of the symptoms, and the susceptibility of the subject to side effects, and preferred dosages for a given compound are readily determinable by those of skill in the art by a variety of means. For example, in order to calculate the dose of peptides of the invention, those skilled in the art can use readily available information with respect to the amount necessary to have the desired effect, depending upon the particular agent used.

7. Pharmaceutical Compositions

The invention also relates to a pharmaceutical composition comprising at least one of the peptides of the invention and a pharmaceutically acceptable carrier or excipient. Examples of suitable pharmaceutical carriers are described in *Remington's Pharmaceutical Sciences* by E. W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid, for example as a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition may take the form of tablets or lozenges according to conventional protocols.

For administration by inhalation, the compounds for use according to the present invention are conveniently delivered in the form of an aerosol spray from a pressurized pack or nebulizer (e.g. in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can be formulated for parenteral administration (i.e. intravenous or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

The pharmaceutical composition can also be formulated for rectal administration as a suppository or retention enema, e.g., containing conventional suppository bases such as cocoa butter or other glycerides.

Peptides of the invention may be linked to chelators such as those described in U.S. Pat. No. 5,326,856. The peptide-chelator complex may then be radiolabeled to provide an imaging agent for diagnosis or treatment of diseases or conditions involving the regulation of IgG levels. The peptides of the invention may also be used in the methods that are disclosed in U.S. Pat. No. 5,449,761 for creating a radiolabeled peptide for use in radiotherapy.

8. Purification of FcRn

The peptides of the invention can also be used to purify FcRn. In some embodiments, the peptide is covalently attached to an appropriate chromatographic matrix to form an efficient FcRn separation media. A solution containing FcRn is then passed over the chromatographic matrix resulting in the non-covalent binding of FcRn to the immobilized binding partner. Solutions containing FcRn may be from biological samples such as a bodily fluid, a tissue or cell sample, cell culture supernatant. The FcRn is purified by washing the immobilized peptide:FcRn complex with a suitable solution to remove impurities and then releasing the FcRn from the chromatographic matrix with a suitable elution solution.

Peptides of the invention can be attached to suitable chromatographic matrices using a number of chemical approaches well known to those skilled in the art. For example, peptides of the invention can be attached to matrices containing suitably reactive groups, such as thiols, amines, carboxylic acids, alcohols, aldehydes, alkyl halides, N-alkyl-maleimides, N-hydroxy-succinimidyl esters, epoxides, hydroxylamines, hydrazides.

In other embodiments, the peptides of the invention can be modified to contain chemical moieties or peptide sequences that bind non-covalently to an appropriate chromatographic matrix. For example, the peptides could be modified with a biotin moiety and could be non-covalently bound to a chromatographic matrix containing an avidin protein. Alternatively, the modified peptide could be incubated with the FcRn solution and the resulting mixture passed over the appropriate chromatographic matrix to isolate the FcRn:peptide complex.

Examples of similar uses of peptides for affinity purification can be found in Kelley et al., "Development and Validation of an Affinity Chromatography Step Using a Peptide Ligand for cGMP Production of Factor VIII", In Biotechnology and Bioengineering, Vol. 87, No. 3, Wiley InterScienc, 2004, pp. 400-412 and in U.S. Pat. No. 6,197,526.

EXAMPLES

The Examples, which are intended to be purely exemplary of the invention and should therefore not be considered to limit the invention in any way, also describe and detail aspects and embodiments of the invention discussed above. The Examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric pressure.

Example 1

Expression of Soluble Human FcRn (shFcRn)

Soluble human FcRn cDNA was cloned, expressed and purified as described in the literature using the glutamine synthetase expression system in Chinese hamster ovary (CHO) cells See U.S. Pat. No. 5,623,053. A stop codon was placed after amino acid position 274 in the protein sequence of human FcRn in order to remove the transmembrane region.

Example 2

Transfection of HEK 293 Cells with Human FcRn

Human embryonic kidney (HEK) 293 cells (ATCC, Manassas, Va.) were transfected using the SuperFect Transfection Reagent (Qiagen, Valencia, Calif.) according to the manufacturer's recommended protocol. The full length FcRn cDNA construct depicted in FIG. 1 (C. M. Story et al., *J. Exp. Med.* 180:2377-2381 (1994), N. E. Simister et al., *Eur. J. Immunol.* 26:1527-1531 (1996)) was originally cloned into pcDNA6 (Invitrogen, Carlsbad, Calif.) as the plasmid vector in order to generate the FcRn expression vector, FcRn: pcDNA6. The Human $\beta_2$m cDNA construct, also depicted in FIG. 1 was originally cloned into pcDNA3 (Invitrogen) as the plasmid vector to generate the human $\beta_2$m expression vector, $\beta_2$m:pcDNA3 (D. Gussow et. al., *J. Immunol.* 139:3132-3138 (1987)).

The day before transfection, HEK293 cells were seeded at $0.5$-$2.5 \times 10^6$ cells per 100 mm dish and incubated at 37° C. and 5% $CO_2$ for 16 hours in cDMEM. The composition of cDMEM contains: 1 L DMEM (Invitrogen #11995-065); 10 ml of 1 M HEPES, pH 7.55; 10 ml MEM amino acid solution (Invitrogen #11130-051); 10 ml MEM non-essential amino acid solution (Invitrogen #11140-050); 10 ml of 100 mM sodium pyruvate (Invitrogen #11360-070); 10 ml of Penicillin Streptomycin liquid (Invitrogen #15140-148); 10 ml L-glutamine solution (Invitrogen #25030-081); 1 ml 2-mercaptoethanol solution in 55 mM Dulbecco phosphate buffered saline (DPBS) (Invitrogen #21985-023); 100 ml heat-inactivated fetal bovine serum (FBS) (Invitrogen). On the day of the transfection, 5 µg of the FcRn:pcDNA6 construct and 5 µg of $\beta_2$m:pcDNA3 DNA were added to 290 µL of DMEM (Invitrogen). The solution was mixed for a few seconds and centrifuged. Then, 60 µL of SuperFect Transfection Reagent (Qiagen) was added to the DNA solution and vortexed for 10 seconds. The DNA/SuperFect solution was incubated for 5 to 10 minutes at room temperature, during which time the media from the cell-containing dish was aspirated and the cells washed once with 4 ml of PBS. After the 5 to 10 minute incubation of the DNA/SuperFect, 3 ml of complete growth medium (cDMEM) was added to the DNA/SuperFect solution, the solution was mixed, and immediately added to the cells in the 100 mm dish.

The cells were incubated with the DNA/SuperFect solution for 2 to 3 hours at 37° C. and 5% $CO_2$. The media containing the DNA/SuperFect solution was removed from the cells the cells were washed 3 times with PBS and fresh cDMEM was added to the cells. After a 48 hour incubation, the medium was assessed by immunoblot analysis to determine if transient expression of the FcRn/$\beta_2$m complex had occurred. In addition, the cells were passaged at a ratio of 1:4 into cDMEM containing 250 µg/L Geneticin (Invitrogen) as an antibiotic and 5 µg/L Blasticidin to select for Blasticidin resistant stable transfectants. After 4 weeks of antibiotic selection, surviving cells were seeded into 96-well tissue culture plates at a density of 1 cell per well. Ultimately 12 clones were selected and each expanded and checked for expression by immunoblot analysis for FcRn and $\beta_2$m. This analysis identified the FcRn and $\beta_2$m-expressing 293 clone 11 as possessing the highest level of expression and was thus used in subsequent assays.

Example 3

Screening of Phage Libraries for FcRn-IgG Inhibitors

Peptides capable of inhibiting the binding of the IgG Fc portion to FcRn were identified by screening filamentous phage display libraries licensed from Dyax Corp. (Cambridge, Mass.). More specifically, the following three libraries were used in combination; TN-9-IV, TN10-X, TN-11-I and TN-12-I were used in the screen. The total number of individual viable phage contained in each library was reflected by the number of transformants established for each library when the libraries were expressed in *E. coli* and plated at a clonal dilution as described by the Dyax protocol. The number of transformants for TN-9-IV, TN10-X, TN-11-I and TN-12-I was $3.2 \times 10^9$, $2 \times 10^9$, $2.7 \times 10^9$ and $1.4 \times 10^9$, respectively. Another way to refer to the absolute number of viable phages in a given volume is by stating the plaque forming units (pfu) per unit volume.

A. Buffers Used in Phage Screening

The following buffers were used for the screening of FcRn-binding peptides.

1. NZCYM Broth: 10 g NZ Amine-A; 5 g sodium chloride; 5 g Bacto Yeast Extract (Difco); 1 g Casamino acids; 1 g magnesium sulfate anhydrous powder: ingredients were dissolved in 800 ml of water, adjusted to pH 7.5 with 1 N sodium hydroxide and then brought up to a total volume of 1 L with water and autoclaved for 20 min.
2. Binding buffer (BB): PBS, pH 6 plus 10 mM EDTA.C. NZCYM-T: NZCYM broth plus 12.5 µg/ml Tetracycline.
3. HBSS-E: Hank's Balanced Saline Solution (Invitrogen) plus 10 mM EDTA (Invitrogen).
4. Min A Salts: 10.5 g $K_2HPO_4$ (potassium phosphate dibasic); 4.5 g $KH_2PO_4$ (potassium phosphate monobasic); 1.0 g $(NH_4)_2SO_4$ (ammonium sulfate) and 0.5 g sodium citrate dissolved in 1 L water.
5. LB Broth: 10 g Bacto Tryptone; 5 g Bacto yeast extract; 10 g sodium chloride dissolved in 1 L water and autoclaved for 20 min.
6. CBS pH 2: 50 mM sodium citrate; 150 mM sodium chloride: buffer was brought to pH 2 with HCl and filter sterilized.
7. LB Agar: 30 g Bacto Tryptone; 15 g Bacto yeast extract; 30 g sodium chloride dissolved in 3 L water and autoclaved for 20 minutes.
8. LB Soft Agar: 20 g Bacto Tryptone; 10 g Bacto yeast extract; 20 g sodium chloride; 14 g Bacto agar dissolved in 2 L water using mild heat without boiling.
9. TE buffer: 10 mM Tris, 1 mM EDTA, pH 7

B. Screening Protocol: Round 1

Approximately 100 random library equivalents of each library were pooled according to their titer, which meant; 24 µL of TN9-IV ($1.3 \times 10^{10-}$ pfu/µL), 12.5 µL of TN10-X ($1.6 \times 10^{10}$ pfu/µL), 225 µL of TN11-I ($1.2 \times 10^9$ pfu/µL), and 48.7 µL of TN12-I ($2.9 \times 10^9$ pfu/µL) were mixed with 189 µL PBS, 75 µL of ice-cold 17% polyethylene glycol (PEG) (average molecular weight: 8000 Da, Sigma-Aldrich, St. Louis, Mo.) and 75 µL of 3 M sodium chloride and incubated on ice for 30 minutes. One T75 flask of 293 clone 11 cells (Example 2) was split at a ratio of 1:3 with HBSS-E. The cells were transferred to a 1 ml microcentrifuge tube, washed once with cold binding buffer and the supernatant removed. The cells were incubated with the phage for 1.5 hours at 4° C. on a rotator. After the incubation, the cells were washed five times with 1 ml of ice-cold BB followed each time by centrifugation at 1400 rpm for 2 minutes. The strongly bound phage were eluted by adding 66 µM human IgG (Calbiochem, San Diego, Calif.) that had been dialyzed into BB. The phage-IgG mix was incubated with the cells for 1 hour at 4° C. Following a centrifugation step (1400 rpm spin for 2 min.), the cell pellet washed first with 200 µL of 66 µM IgG, centrifuged (1400 rpm spin for 2 min.) and washed a final time with 100 µl IgG. The IgG washes were combined with the IgG elution for final volume of 500 µl. The phage in the eluent were titered and amplified as described below.

C. Phage Titer

Phage solutions were diluted in 100-fold steps. Typically 2 µl of phage solution was added to 198 µL of NZCYM broth in a serial manner to achieve dilutions of up to $10^{-10}$. Diluted phage were added to a culture of XL1 Blue MRF' *E. coli* cells when the XL1 Blue MRF' *E. coli* cells were being grown in log phase and reached an optical density of 0.5 at A600 (UV absorbance at 600 nm). The culture was incubated at room temperature for 10 minutes. Afterwards, 0.5 ml of the infected cells were added to 3.5 ml of molten top agar (a 50/50 mix of LB broth and LB agar) at approximately 55° C. and spread onto a standard agar plate and incubated overnight at 37 degrees. The titer was calculated from a plate containing 30 to 300 plaques. For a plate containing 50 plaques, plated from a $10^{-8}$ phage dilution, the calculations would be performed as follows: 50 plaques/500 µL infected cells×10-fold dilution during infection×$10^8$ phage dilution=$10^8$ plaque-forming units per µL.

When necessary for subsequent phage ELISA and sequencing analysis, individual agar plugs containing phage plaques were picked with autoclaved Pasteur pipets. Plugs were deposited in 96-well sterile round-bottom tissue culture plates (Greiner), to which 100 µL per well TE were added. Phage were eluted from the plaques for 2 hours at 37° C. or overnight at 4° C.

D. Phage Amplification

A culture of XL1 blue MRF' *E. coli* cells were grown in NZCYM broth-T, from a 1/100 dilution of a saturated overnight culture until the culture reached an optical density of 0.5 at A600. The cells were concentrated by centrifuging them for 15 minutes at 3500 rpm, followed by resuspension in Min A salts to 1/20 of the original volume. The phage eluted from cells after a round of selection were diluted to a 1 ml final volume in Min A salts and added to 1 ml of the concentrated bacterial culture. After a 15 minute incubation in a 37° C. water bath, the phage-cell mix was added to 2 ml 2×NZCYM broth and spread on a large NUNC plate with NZCYM plus 50 µg/ml Ampicillin until dry. Plates were incubated for 14 to 18 hours at 37° C. Colonies that formed overnight were scraped gently with a spreading bar in the presence of 20 ml of PBS. PBS-containing bacteria and phage were collected in a centrifuge tube. Bacteria remaining on the plate were scraped again in the presence of 10 ml PBS and collected. A final 10 ml PBS rinse was applied to the plate, and pooled together with all scraped material. The bacterial cells were pelleted by centrifugation (15 minutes at 3500 rpm), and the clear supernatant was decanted into another centrifuge tube, clarified again, and finally decanted again. Then, a 0.15 mL volume of 17% PEG+3M NaCl was added to the supernatant, which was mixed and stored overnight at 4° C. The precipitated phage collected by centrifugation (8500×g for 30 minutes), after which the supernatant was discarded. The phage pellet was resuspended in a small volume of PBS, clarified with a brief spin, and precipitated again with a 0.15 volume of 17% PEG+3M NaCl. The final phage pellet was resuspended in PBS and titered in preparation for the next round of selection.

E. Round 2

The amplified phage library was diluted such that only 10 random library equivalents were diluted into 1 ml of binding buffer. One third of a T75 flask of untransfected 293 cells washed once with cold binding buffer. A subtraction step included to remove phage from the library that expressed peptides capable of binding to cells that did not express FcRn was performed twice by incubating the phage with the untransfected cells for 15 minutes. The supernatant was recovered. Then, one third of a T75 flask of 293 clone 11 cells washed once with cold binding buffer and incubated with the phage for 1.5 hours at 4° C. in a rotator. The cells were washed and centrifuged (1400 rpm spin for 2 min.) five times with 1 ml cold binding buffer and the strongly bound phage were eluted with 200 µL of 66 µM human IgG (dialyzed in binding buffer) by incubating the phage-cell-IgG mixture for 1 hour at 4° C. After centrifugation (1400 rpm spin for 2 min.), the supernatant was collected and the pellet washed with 200 µL of 66 uM IgG, followed by a 100 µL wash of 66 uM IgG. The phage in the eluent were titered and amplified as described below in the sections labeled phage titer and phage amplification.

F. Round 3

This round was performed as described above for Round 2. At the completion of Round 3, the phage in the eluent were titered and assayed for IgG-FcRn inhibitors using the phage ELISA.

G. Phage ELISA

The following steps were carried out to identify, by enzyme linked immunosorbent assay (ELISA), phages encoding peptides that were able to bind FcRn. First, the following solutions were prepared:
Buffer A: PBS+0.1% Tween+0.5% BSA.
Buffer B: 100 mM MES, pH 5.5+150 mM NaCl+0.1% Tween.
Buffer C: 50 mM MES, pH 6.0+150 mM NaCl+0.1% Tween
An XL1 blue MRF' *E. coli* culture for the propagation of a phage that demonstrated the ability to bind FcRn was grown to an optical density of 0.5 at A600 from a 1:100 dilution of an overnight culture. Then, 10 µl of each phage plaque eluate that was prepared as described above were added to 30 µl of the XL1 blue MRF' *E. coli* cells into wells of a 96-well plate and incubated for 15 minutes at room temperature. Then, 130 µl of NZCYM broth containing 50 µg/ml of Ampicillin were added to each well and the plates were incubated overnight at 37° C.

A Streptavidin-coated, BSA-blocked microtiter plate (Pierce) was prepared by rinsing it with 200 µl per well of buffer A, and coating it overnight at 4° C. with 1 mg/ml of biotinylated soluble human FcRn (Example 4, section A), in buffer A. The FcRn-containing buffer was discarded and the plate was rinsed twice with buffer C. Then, 70 µl of buffer B was added to each well of the plate, followed by the addition of 30 µl of a bacterial culture containing phage. After 1 hour at room temperature, the plate washed five times with 200 µl of buffer C. Then, 100 µl of buffer C containing a 1:10000 dilution of an HRP-conjugated anti-M13 antibody (Amersham Pharmacia) was added to each well. The plate was incubated at room temperature for one hour. Then, the plates were washed 9 times with buffer C, developed with 1 step TMB (KPL), stopped after 5-15 minutes with 2M sulfuric acid and read at 450 nm with a Spectra Max Plus plate reader (Molecular Devices).

H. PCR Amplification of Phage DNA

Phage eluted from plaques in TE were amplified for sequencing by using the PCR Core System II kit per the manufacturer's instructions (Promega). Then, 5 ml of eluted phage was added to a reaction mix containing 200 μM each dNTP, 500 nM of primer 3PCRUP (5'-CGGCGCAAC-TATCGGTATCAAGCTG-3') (SEQ ID NO:11), 500 nM of primer 3PCRDN (5'-CATGTACCGTAACACT-GAGTTTCGTC-3') (SEQ ID NO:12), 1× Taq DNA Polymerase Buffer (10×: 500 mM KCl, 100 mM Tris-HCl pH 9.0 at 25° C., 1% Triton X-100, 15 mM $MgCl_2$), and 1.25 units Taq DNA Polymerase enzyme. The reactions were subjected to the following program on a MJ Research PCT-200 thermal cycler: 5 minutes at 94° C.; 30 cycles consisting of 15 seconds at 94° C., 30 seconds at 55° C., and 60 seconds at 72° C., followed by 7 minutes at 72° C. The resulting product was purified using the QiaQuick PCR Prep kit (Qiagen) according to manufacturer's instructions, quantified by absorbance at A260, and sequenced using primer 3SEQ-80 (5'-GATAAAC-CGATACAATTAAAGGCTCC-3') (SEQ ID NO:13).

Sequencing of phage that was amplified following the 3 rounds of screening revealed the DNA sequences that encoded the amino acid sequences provided in FIG. 1. These "phage hits" were used collectively to identify a consensus peptide sequence, defined by the amino acid sequence: G-H-F-G-G-X-Y (SEQ ID NO: 14).

Example 4

Peptide-IgG Competition ELISA

In order to determine whether the peptides of the invention that were derived from the screening of the filamentous phage display libraries were also able to block the binding of IgG to FcRn, the following ELISA assay was devised and performed.

A. Biotinylation of shFcRn

A solution of soluble human FcRn (shFcRn) in Tris buffer was dialyzed twice, each time for 3 hours in 2 liters of PBS, pH 8.0. The quantity of recovered shFcRn was determined by measuring the absorbance at 280 nm. The concentration of shFcRn was obtained by multiplying the absorbance reading by the extinction coefficient for shFcRn, which is: $\epsilon=85880$ $M^{-1}$ $cm^{-1}$. Biotinylation of shFcRn was accomplished by treating the dialyzed shFcRn with a 2-fold-molar excess of Sulfo-NHS-LC-Biotin (Invitrogen, Carlsbad, Calif.) for 2 hours at 4° C. Afterwards, the shFcRn-Sulfo-NHS-LC-Biotin reaction mixture was dialyzed twice in 2 L of cold PBS, followed by another absorbance reading to determine the concentration of the remaining protein. The biotinylated shFcRn was stored at 4° C. with 0.1% sodium azide until needed.

B. Peptide-IgG Competition ELISA Assay 96-well ReactiBind Neutravidin-coated plates blocked with BSA (Pierce, Rockford, Ill.) were washed twice with 200 μl/well of Buffer A (Buffer A: PBS pH 7.4 (Gibco, 14040), 0.5% BSA IgG-free, 0.05% Tween-20). The wells were coated with 100 μl/well of 1 μg/ml biotinylated-shFcRn in Buffer A. The plate was sealed and incubated at 37° C. for 2 hours. Afterwards, the plate washed with 200 μl/well of Buffer B (Buffer B: 100 mM MES pH 6, 150 mM NaCl, 0.5% BSA IgG-free (Jackson ImmunoResearch, West Grove, Pa.), 0.05% Tween-20). Then, 50 μl/well of 6 nM human IgG (Calbiochem, San Diego, Calif.) in Buffer B as well as 50 μl/well of the various peptide competitors (at various concentration) were added, so that the final concentration of IgG in the well was 3 nM. To allow for mixing, the plate was rocked for 2 minutes, sealed and incubated at 37° C. for 2 hours. Following the incubation, the liquid was aspirated from the plate and 100 μl/well of a 1:10 000 dilution of Peroxidase-conjugated goat anti-human IgG F(ab') fragment-specific $F(ab')_2$ fragment (Jackson ImmunoResearch, West Grove, Pa.) in Buffer B was added. The plate was covered, incubated for 30 minutes at room temperature and washed 4 times with 200 μl/well of ice-cold buffer B. SureBlue TMB substrate solution (100 μl/well, KPL, Gaithersburg, Md.) was added and the plate was allowed to incubate at room temperature until color developed, which took 5 to 10 minutes. Once color developed, 100 μl/well of TMB stop solution (KPL, Gaithersburg, Md.) was added and the absorbance was measured at 450 nm. The data was plotted as absorbance vs. peptide concentration to derive the inhibitory concentration 50% ($IC_{50}$) values.

Example 5

Peptide-IgG Competition FACS Assay

In addition to using the ELISA approach described in Example 4 to determine whether the peptides of the invention that were derived from the screening of the filamentous phage display libraries were also able to block the binding of IgG to FcRn on cells, the following fluorescence activated cell sorting (FACS) assay was devised and performed.

A. Labeling of Synagis® with Alexa-Fluor-488

Humanized IgG1 (Synagis®, MedImmune, Gaithersburg, Md.) was labeled with the Alexa Fluor 488 Protein Labeling Kit (Molecular Probes/Invitrogen, Carlsbad, Calif.) according to the manufacturer's suggested protocol. Briefly, 50 μl of 1 M sodium bicarbonate, pH 9.0 was added to 500 μl of a 2 mg/ml solution of IgG in PBS. This protein solution was added to the Alexa Fluor 488 succinimidyl ester (dry powder) and incubated at room temperature for 1 hour. The protein was purified by size-exclusion chromatography using the kit component column (Bio-Rad BioGel P-30 Fine size exclusion purification resin). The sample was loaded onto the column and eluted with PBS. The first colored band contained the labeled protein. The degree of labeling was determined by measuring the absorbance of the eluted IgG at 280 nm and 494 nm. The protein molar concentration was determined using the formula: protein concentration $(M)=[A_{280}-(A_{494}\times 0.11)\times \text{dilution factor}]/203{,}000$. In addition, the formula used to derive the moles of dye per mole of protein was: $=A_{494}\times \text{dilution factor}/71{,}000\times \text{protein concentration (M)}$. Typically, 4-7 moles of Alexa-Fluor 488 were incorporated per mole of IgG.

B. IgG-Peptide Competition FACS Assay Using 293 Clone 11 Cells

In preparation for the assay, HEK 293 clone 11 cells (Example 2) in complete DMEM media (Gibco, Carlsbad, Calif.) containing 5 μg/ml Blasticidin and 250 μg/ml G418 (Gibco, Carlsbad, Calif.) were spun down and resuspended in Buffer C (Buffer C: Dulbecco's PBS (Gibco, Carlsbad, Calif.) containing 10 mM EDTA (Gibco)) at a concentration of $3\times 10^6$ cells/ml. Cells (0.1 ml) were pipetted into each well of a 96-well assay plate and the plates were centrifuged at 2600 RPM for 5 min using a Sorvall RT7 benchtop centrifuge. The supernatants were gently decanted and the plate was blotted on a paper towel. Peptide competitors (90 μl) solubilized in Buffer C at various concentrations were added to the plate and mixed with a multi-channel pipette. 10 μl of Alexa 488-labeled Synagis® was added to each well on the plate, such that the final concentration of Alexa 488-labeled Synagis® was 100 nM. The plate was wrapped in foil, placed on ice for one hour and subsequently centrifuged at 2600 rpm for 5 minutes in a Sorvall RT7 benchtop centrifuge followed by a single wash with 100 µl of Buffer C and a second centrifugation step. The cells were resuspended in 200 µl of Buffer C and analyzed on a Beckman Coulter EPICS XL flow cytometer.

Example 6

Methods for the Determination of Equilibrium Binding Constants ($K_D$) for Peptides Using Surface Plasmon Resonance (SPR)

The following steps were performed to cross-link soluble human or cynomolgus FcRn to the dextran surface of a CM5 sensor chip (Biacore AB, Uppsala, Sweden) by an amine coupling reaction involving 1-ethyl-(3-dimethylaminopropyl)-carbodiimide hydrochloride (EDC) (Biacore AB, Uppsala, Sweden) and N-hydroxysuccinimide (NHS) (Biacore AB, Uppsala, Sweden) as recommended by Biacore (BIApplications Handbook, version AB, section 4.2, Biacore AB, Uppsala, Sweden). The FcRn protein was diluted in 50 mM sodium acetate, pH 4.5 (Biacore AB, Uppsala, Sweden) to a concentration of 10 to 30 µg/ml and used to coat one flow cell on the sensor chip. Residual sites on the FcRn flow cell were blocked with 1 M ethanolamine hydrochloride pH 8.5 (Biacore AB, Uppsala, Sweden). A control flow cell was blocked with ethanolamine for reference subtraction. For analysis of the monomeric peptides, FcRn was coated to a final density of 4000-5000 response units (RU). For analysis of the peptide dimers, FcRn was coated to a density of 2000-2500 RU. All SPR measurements were performed using a BIACORE 3000 Instrument (Biacore AB Uppsala, Sweden). For measurements done at either pH 6 or pH 7.4, experiments were performed in 50 mM phosphate, 100 mM sodium chloride, 0.01% surfactant P20 (Biacore AB, Uppsala, Sweden).

A. Representative Procedure for the Determination of Binding Constant of Monomeric Peptides Ten, 2-fold dilutions of the peptide were injected over the FcRn-CM5 chip at a rate of 20 µl/min for 2 min. The peptide was dissociated from the chip for 2.5 minutes with buffer. Any remaining peptide was removed from the chip with a 30 second injection of HBS-P buffer (Biacore AB, Uppsala, Sweden) at a rate of 30 µl/min. Sensorgrams were generated and analyzed using BiaEval software version 3.1 (Biacore AB, Uppsala, Sweden). The equilibrium RU observed for each injection was plotted against concentration. The equilibrium $K_D$ values were derived by analysis of the plots using the steady state affinity model included in the BiaEval software.

B. Representative Procedure for Determination of Binding Constant of Dimeric Peptides Ten, 2-fold dilutions of the peptide were injected over the FcRn-CM5 chip at a rate of 30 µl/min for 10 min. Peptides were dissociated from the chip for 10 minutes with buffer. Any remaining peptide was removed from the chip with two, 60 second injections of a solution containing 50 mM Tris-hydrochloride, 100 mM NaCl, 0.01% surfactant P20 pH 9.0 at 100 µl/min.

Sensorgrams were generated and analyzed using BiaEval software version 3.1 (Biacore AB, Uppsala, Sweden). The equilibrium RU observed for each injection was plotted against concentration. The equilibrium $K_D$ values were derived by analysis of the plots using the steady state affinity model included in the BiaEval software.

Example 7

Synthesis of Monomeric Peptides Containing Disulfide Bonds

Synthesis of monomeric peptides was performed using solid-phase peptide synthesis either manually with a fritted round bottom flask or by using an Advanced Chemtech 396-omega synthesizer (Advanced Chemtech, Louisville, Ky.). Standard Fmoc/tBu protocols were used (W. C. Chan and P. D. White eds., *Fmoc Solid Phase Peptide Synthesis: A Practical Approach* Oxford University Press Inc. New York (2000)), in combination with a Rink amide resin (Novabiochem, San Diego, Calif.) or PAL-PEG-PS (Applied Biosystems, Foster City, Calif.) to yield C-terminal amides upon cleavage. The coupling reagents were 2-(1H-Benzotriazole-1-yl)-1,1,3,3-tetramethyluronium hexafluorophosphate (HBTU) and N-hydroxybenzotriazole (HOBt) (Novabiochem, San Diego, Calif.). The base was diisopropylethylamine (DIEA) (Sigma-Aldrich, St. Louis, Mo.), and N,N-dimethylformamide (DMF) was the solvent (EM Science, Kansas City, Mo.). The typical synthesis cycle involved 2×10 minute deprotection steps with 20% piperidine in DMF, 2×30 minute amino acid couplings with HOBt/HBTU and a 10 minute capping step with acetic anhydride/HOBt. Peptides were cleaved from the resin by treatment for 2 hours with 95% trifluoroacetic acid; 2.5% thanedithiol 1.5% triisopropylsilane and 1% water and precipitated with ice-cold ether, centrifuged and triturated three times with ether.

Crude cysteine-containing peptides were oxidized to their corresponding disulfides by dissolving the peptides to a concentration of 1 mg/ml in a 4:1 mixture of acetic acid and water (EM Science, Kansas City, Mo.). Ten molar equivalents of iodine (1M solution in water, Sigma-Aldrich, St. Louis, Mo.) were added to the solution and the reaction mixture was mixed for one hour at room temperature. The reaction was stopped by the progressive addition of 1 M sodium thiosulfate (Sigma-Aldrich, St. Louis, Mo.) until a clear solution was obtained. The reaction mixture was concentrated in vacuo and subsequently purified using a Waters Prep600 reversed phase HPLC system (Millford, Mass.) equipped with a 250 mm×21.2 mm Phenomenex (Torrence Calif.) C18 column. The eluent chosen for the HPLC purification step was a gradient of acetonitrile in water containing 0.1% (w/v) TFA. Appropriate fractions were collected, pooled and lyophilized. Peptide identity and purity was confirmed by reversed phase analytical HPLC in combination with a 250 mm×2 mm column (Phenomenex, Torrence, Calif.) coupled with electrospray mass spectrometry (Mariner ES-MS) (Applied Biosystems, Foster City, Calif.).

Table 2 provides a listing of the original phage peptide sequences derived from the screen of the peptide expression library used to identify peptides with a high affinity for human FcRn and the ability to block the IgG-FcRn interaction. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6.

TABLE 2

Original Phage Peptide Sequences

| | Sequence | IC$_{50}$ μM | K$_D$ (pH 6) μM | K$_D$ pH 7.4 μM |
|---|---|---|---|---|
| SEQ ID NO:6 | AGQRFCTGHFGGLYPCNGPGTGGGK | 36 | 5.7 | 45 |
| SEQ ID NO:7 | AGGGCVTGHFGGIYCNTQGTGGGK | 33 | 5.2 | 34.7 |
| SEQ ID NO:8 | AGKIICSPGHFGGMYCQGKGTGGGK | 64 | 22 | 78 |
| SEQ ID NO:9 | AGPSYCIEGHIDGIYCFNAGTGGGK | 49 | 8.8 | 76 |
| SEQ ID NO:10 | AGNSFCRGRPGHFGGCYLFGTGGGK | 33 | 9.4 | 93 |

Table 3 provides a listing of truncations of the SEQ ID NO:6 peptide. The effect of the truncations on the binding parameters of these peptides with human FcRn are shown. Column 1 contains the peptide identifier. Column 2 contains the amino acid sequence of the peptides. Column 3 contains the IC$_{50}$ of each peptide as determined by the IgG competition ELISA outlined in Example 4. Columns 4 and 5 contain the K$_D$ of each peptide as determined at pH 6 and pH 7.4, respectively, by the Biacore analysis outlined in Example 6.

TABLE 3

Truncations of SEQ ID NO:6

| | Sequence | IC$_{50}$ μM | K$_D$ (pH 6) μM | K$_D$ pH 7.4 μM |
|---|---|---|---|---|
| SEQ ID NO:6 | AGQRFCTGHFGGLYPCNGPGTGGGK | 36 | 5.7 | 45 |
| SEQ ID NO:1 | QRFCTGHFGGLYPCNGP | 26 | 5.1 | 30 |
| SEQ ID NO:17 | CTGHFGGLYPCNGP | 239 | 34 | nd |
| SEQ ID NO:18 | QRFCTGHFGGLYPC | 27 | 4.2 | 26 |
| SEQ ID NO:19 | CTGHFGGLYPC | 110 | 20 | 320 |
| SEQ ID NO:20 | TGHFGGLYP | >250 | >250 | nd |
| SEQ ID NO:21 | RFCTGHFGGLYPCNGP | 24 | 2.9 | 78 |
| SEQ ID NO:22 | FCTGHFGGLYPCNGP | 67 | 11 | 120 |
| SEQ ID NO:23 | QRFCTGHFGGLYPCNG | 34 | 4.6 | 69 |
| SEQ ID NO:24 | QRFCTGHFGGLYPCN | 31 | 6.1 | 73 |

Table 4 provides a listing of SEQ ID NO:1-derived peptides and peptide analogs, in which single amino acids have been substituted with alanine (an alanine scan). The effect of the substitutions on the binding parameters of these peptides with human FcRn are shown. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6.

TABLE 4

Alanine Scan of SEQ ID NO:1

| | Sequence | $IC_{50}$ µM | $K_D$ (pH 6) µM | $K_D$ pH 7.4 µM |
|---|---|---|---|---|
| SEQ ID NO:1 | QRFCTGHFGGLYPCNGP | 26 | 5.1 | 30 |
| SEQ ID NO:25 | Q<u>A</u>FCTGHFGGLYPCNGP | 23 | 7.7 | nd |
| SEQ ID NO:26 | QR<u>A</u>CTGHFGGLYPCNGP | 95 | 28 | nd |
| SEQ ID NO:27 | QRFC<u>A</u>GHFGGLYPCNGP | 30 | 4.9 | nd |
| SEQ ID NO:28 | QRFCT<u>A</u>HFGGLYPCNGP | >125 | >250 | nd |
| SEQ ID NO:29 | QRFCTG<u>A</u>FGGLYPCNGP | >125 | >250 | nd |
| SEQ ID NO:30 | QRFCTGH<u>A</u>GGLYPCNGP | >125 | >250 | nd |
| SEQ ID NO:31 | QRFCTGHF<u>A</u>GLYPCNGP | >125 | 230 | 200 |
| SEQ ID NO:32 | QRFCTGHFG<u>A</u>LYPCNGP | >125 | 120 | 110 |
| SEQ ID NO:33 | QRFCTGHFGG<u>A</u>YPCNGP | 107 | 26 | 81 |
| SEQ ID NO:34 | QRFCTGHFGGL<u>A</u>PCNGP | >125 | >250 | nd |
| SEQ ID NO:35 | QRFCTGHFGGLY<u>A</u>CNGP | 96 | 14 | 100 |
| SEQ ID NO:36 | QRFCTGHFGGLYPC<u>A</u>GP | 30 | 8 | nd |

Table 5 provides a listing of SEQ ID NO:1-derived peptides and peptide analogs in which substitutions of cysteines with cysteine derivatives have been performed. The effect of the substitutions on the binding parameters of these peptides with human FcRn are shown. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6.

TABLE 5

Cysteine Derivatives of SEQ ID NO:1

| | Sequence (SEQ ID NOS 1 & 37-47) | $IC_{50}$ µM | $K_D$ (pH 6) µM | $K_D$ pH 7.4 µM |
|---|---|---|---|---|
| SEQ ID NO:1 | QRF-C-TGHFGGLYP-C-NGP | 26 | 5.1 | 30 |
| Peptide No. 27 | QRFCTGHFGGLYP-h<u>C</u>-NGP | 21 | 3.9 | |
| Peptide No. 28 | QRF-h<u>C</u>-TGHFGGLYP-h<u>C</u>-NGP | 20 | 3.8 | |
| Peptide No. 29 | QRF-<u>c</u>-TGHFGGLYP-C-NGP | >125 | 150 | |
| Peptide No. 30 | QRF-C-TGHFGGLYP-<u>c</u>-NGP | 125 | 31 | |
| Peptide No. 31 | QRF-<u>c</u>-THGFGGLYP-<u>c</u>-NGP | >500 | 200 | |
| Peptide No. 32 | QRF-<u>Pen</u>-TGHFGGLYP-C-NGP | 2 | 0.25 | |
| Peptide No. 33 | QRF-C-TGHFGGLYP-<u>Pen</u>-NGP | 18 | 2.7 | |
| Peptide No. 34 | QRF-<u>Pen</u>-TGHFGGLYP-<u>Pen</u>-NGP | 2 | 0.37 | |
| Peptide No. 69 | QRF-<u>Pen</u>-TGHFGGLYP-h<u>C</u>-NGP | 2 | 0.31 | |
| Peptide No. 70 | QRF-h<u>C</u>-TGHFGGLYP-<u>Pen</u>-NGP | 16 | 2.1 | |
| Peptide No. 295 | QRF-<u>Pen</u>-TGHFG-<u>p</u>-LYP-<u>Pen</u>-NGP | 1.6 | 0.28 | |

* "Pen" = L-penicillamine; "hC" = L-homocysteine;

Table 6 provides a listing of SEQ ID NO:1 and Peptide No. 32 derived peptides in which single amino acids have been substituted for N-methyl amino acids. The effect of the substitutions on the binding parameters of these peptides with human FcRn are shown. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6.

TABLE 6

N-Methyl Scan of SEQ ID NO:1 and Peptide No. 32

| | Sequence (SEQ ID NOS 1 & 48-60) | $IC_{50}$ µM | $K_D$ (pH 6) µM | $K_D$ pH 7.4 µM |
|---|---|---|---|---|
| SEQ ID NO:1 | QRFCTGHFGGLYPCNGP | 26 | 5.1 | 30 |
| Peptide No. 196 | QRFC-NMeAla-GHFGGLYPCNGP | 169 | 18 | |
| Peptide No. 32 | QRF-Pen-TGHFGGLYP-C-NGP | 2 | 0.25 | |
| Peptide No. 108 | QRF-Pen-T-Sar-HFGGLYP-C-NGP | >125 | 88 | |
| Peptide No. 192 | RF-Pen-TG-NMeHis-FGGLYPC | >250 | nd | |
| Peptide No. 110 | QRF-Pen-TGH-NMePhe-GGLYPCNGP | >125 | >250 | |
| Peptide No. 111 | QRF-Pen-TGHF-Sar-GLYPCNGP | 27 | 2 | |
| Peptide No. 112 | QRF-Pen-TGHFG-Sar-LYPCNGP | 0.9 | 0.11 | |
| Peptide No. 113 | QRF-Pen-TGHFGG-NMeLeu-YPCNGP | 1.6 | 0.086 | |
| Peptide No. 114 | QRF-Pen-TGHFGGL-NMeTyr-PCNGP | >125 | 92 | |
| Peptide No. 146 | RF-Pen-TGHFGG-NMeLeu-YPCNGP | 2.1 | 0.059 | 0.28 |
| Peptide No. 147 | RF-Pen-TGHFG-Sar-YPCNGP | 1.0 | 0.058 | 0.35 |
| Peptide No. 187 | QRF-Pen-TGHFG-Sar-NMeLeu-YPCNGP | 0.42 | 0.046 | 0.23 |
| Peptide No. 235 | RF-Pen-TGHFG-Sar-NMeLeu-YPC | 0.49 | 0.031 | 0.17 |

* Sar = sarcosine; NMeAla = N-methyl alanine; "NMe" prefix denotes N-methyl amino acid Table 7 provides a listing of truncations of Peptide No. 32-derived peptide derivatives. The effect of the truncations on the binding parameters of these peptides with human FcRn are shown. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6.

TABLE 7

Truncations of Peptide No. 32

| | Sequence (SEQ ID NOS 61-69) | $IC_{50}$ µM | $K_D$ (pH 6) µM | $K_D$ pH 7.4 µM |
|---|---|---|---|---|
| Peptide No. 32 | QRF-Pen-TGHFGGLYPCNGP | 2 | 0.25 | 1.2 |
| Peptide No. 82 | F-Pen-TGHFGGLYPC | 1.7 | 0.31 | 5 |
| Peptide No. 83 | $NH_2$-F-Pen-TGHFGGLYPC | 3.1 | 0.29 | 12 |
| Peptide No. 99 | RF-Pen-TGHFGGLYPC | 2.0 | 0.17 | 3.4 |
| Peptide No. 141 | QRF-Pen-TGHFGpLYPC | 1.5 | 0.19 | |
| Peptide No. 142 | RF-Pen-TGHFGpLYPC | 1.5 | 0.14 | |
| Peptide No. 143 | F-Pen-TGHFGpLYPC | 1.7 | | |

TABLE 7-continued

Truncations of Peptide No. 32

| | Sequence (SEQ ID NOS 61-69) | IC$_{50}$ µM | K$_D$ (pH 6) µM | K$_D$ pH 7.4 µM |
|---|---|---|---|---|
| Peptide No. 144 | RF-Pen-TGHFGpLYPCNGP | 1.5 | | |
| Peptide No. 145 | F-Pen-TGHFGpLYPCNGP | 3.1 | | |

* "Pen" = L-penicillamine

Table 8 provides a listing of Peptide No. 32-derived peptides and peptide analogs, in which substitutions with various amino acid and amino acid derivatives have been generated where there is normally the sequence: Gly-Gly-Leu. Column 1 contains the peptide identifier. Column 2 contains the amino acid sequence of the peptides. Column 3 contains the IC$_{50}$ of each peptide as determined by the IgG competition ELISA outlined in Example 4. Columns 4 and 5 contain the K$_D$ of each peptide as determined at pH 6 and pH 7.4, respectively, by the Biacore analysis outlined in Example 6.

TABLE 8

Analogs of Peptide No. 32 at Gly-Gly-Leu

| | Sequence (SEQ ID NOS 70-98) | IC$_{50}$ µM | K$_D$ (pH 6) µM | K$_D$ pH 7.4 µM |
|---|---|---|---|---|
| Peptide No. 32 | QRF-Pen-TGHF-GG-LYP-C-NGP | 2 | 0.25 | 1.2 |
| Peptide No. 40 | QRF-Pen-TGHF-G-p-LYPCNGP | 1.4 | 0.23 | 1.1 |
| Peptide No. 41 | QRF-Pen-TGHF-G-r-LYPCNGP | 8.1 | 0.83 | 8.8 |
| Peptide No. 42 | QRF-Pen-TGHF-G-h-LYPCNGP | 12 | 2 | 20 |
| Peptide No. 43 | QRF-Pen-TGHF-G-i-LYPCNGP | 18 | 2.2 | 41 |
| Peptide No. 44 | QRF-Pen-TGHF-G-f-LYPCNGP | 13 | 1.7 | 100 |
| Peptide No. 45 | QRF-Pen-TGHF-G-y-LYPCNGP | 13 | 1.5 | 31 |
| Peptide No. 46 | QRF-Pen-TGHF-G-Aib-LYPCNGP | 2.4 | 0.48 | 5.3 |
| Peptide No. 47 | QRF-Pen-TGHF-d-G-LYPCNGP | 3.1 | 0.58 | 4.9 |
| Peptide No. 48 | QRF-Pen-TGHF-p-G-LYPCNGP | 5 | 0.79 | 21 |
| Peptide No. 49 | QRF-Pen-TGHF-r-G-LYPCNGP | 4.1 | 0.31 | |
| Peptide No. 50 | QRF-Pen-TGHF-h-G-LYPCNGP | 3.6 | 0.41 | |
| Peptide No. 51 | QRF-Pen-TGHF-i-G-LYPCNGP | 9.4 | 2.6 | |
| Peptide No. 52 | QRF-Pen-TGHF-f-G-LYPCNGP | 2.8 | 0.51 | |
| Peptide No. 53 | QRF-Pen-TGHF-y-G-LYPCNGP | 3.2 | 0.32 | |
| Peptide No. 54 | QRF-Pen-TGHF-Aib-G-LYPCNGP | 17 | 5.2 | |
| Peptide No. 74 | QRF-Pen-TGHF-G-a-LYPCNGP | 2 | 0.48 | 12 |
| Peptide No. 75 | QRF-Pen-TGHF-a-G-LYPCNGP | 4.5 | 0.49 | 4.5 |
| Peptide No. 148 | QRF-Pen-TGHF-a-a-LYPCNGP | 4.5 | 0.45 | |
| Peptide No. 149 | QRF-Pen-TGHF-a-p-LYPCNGP | 3.7 | 0.43 | |
| Peptide No. 150 | QRF-Pen-TGHF-f-p-LYPCNGP | 5.9 | 0.72 | |
| Peptide No. 151 | QRF-Pen-TGHF-f-a-LYPCNGP | 4.3 | 0.41 | |
| Peptide No. 152 | QRF-Pen-TGHF-p-p-LYPCNGP | 21 | 3.3 | |
| Peptide No. 153 | QRF-Pen-TGHF-f-G-NMeLeu-YPCNGP | 1.3 | 0.24 | |
| Peptide No. 154 | QRF-Pen-TGHF-a-G-NMeLeu-YPCNGP | 3.2 | 0.23 | |
| Peptide No. 155 | QRF-Pen-TGHF-f-G-P-YPCNGP | 39 | 18.3 | |

TABLE 8-continued

Analogs of Peptide No. 32 at Gly-Gly-Leu

| | Sequence (SEQ ID NOS 70-98) | IC$_{50}$ μM | K$_D$ (pH 6) μM | K$_D$ pH 7.4 μM |
|---|---|---|---|---|
| Peptide No. 202 | QRF-Pen-TGHF-p-P-LYPCNGP | >250 | >100 | |
| Peptide No. 203 | QRF-Pen-TGHF-f-P-LYPCNGP | 22 | 3.8 | |
| Peptide No. 189 | QRF-Pen-TGHF-a-Sar-LYPCNGP | 1.7 | 0.19 | |

* "Sar" = sarcosine; "Aib" = aminoisobutyric acid

Table 9 provides a listing of Peptide No. 32-derived peptides and peptide analogs, in which substitutions with various amino acid and amino acid derivatives have been generated where there is normally the sequence: Arg-Phe-Penicillamine. Column 1 contains the peptide identifier. Column 2 contains the amino acid sequence of the peptides. Column 3 contains the IC$_{50}$ of each peptide as determined by the IgG competition ELISA outlined in Example 4. Columns 4 and 5 contain the K$_D$ of each peptide as determined at pH 6 and pH 7.4, respectively, by the Biacore analysis outlined in Example 6.

TABLE 9

Analogs of Peptide No. 32 at Arg-Phe-Pen

| | Sequence (SEQ ID NOS 99-102) | IC$_{50}$ μM | K$_D$ (pH 6) μM | K$_D$ pH 7.4 μM |
|---|---|---|---|---|
| Peptide No. 32 | QR-F-Pen-TGHFGGLYPCNGP | 2 | 0.25 | 1.2 |
| Peptide No. 96 | QR-f-Pen-TGHFGGLYPCNGP | 11.4 | 1.8 | |
| Peptide No. 97 | QR-Y-Pen-TGHFGGLYPCNGP | 2.4 | 0.31 | |
| Peptide No. 98 | QR-W-Pen-TGHFGGLYPCNGP | 1.5 | 0.29 | |

Table 10 provides a listing of Peptide No. 32-derived peptides and peptide analogs, in which substitutions with various amino acid and amino acid derivatives have been generated where there is normally the sequence: Penicillamine-Thr-Gly. Column 1 contains the peptide identifier. Column 2 contains the amino acid sequence of the peptides. Column 3 contains the IC$_{50}$ of each peptide as determined by the IgG competition ELISA outlined in Example 4. Columns 4 and 5 contain the K$_D$ of each peptide as determined at pH 6 and pH 7.4, respectively, by the Biacore analysis outlined in Example 6.

TABLE 10

Analogs of Peptide No. 32 at Pen-Thr-Gly

| | Sequence (SEQ ID NOS 99-102) | IC$_{50}$ μM | K$_D$ (pH 6) μM | K$_D$ pH 7.4 μM |
|---|---|---|---|---|
| Peptide No. 32 | QRF-Pen-T-GHFGGLYPCNGP | 2 | 0.25 | 1.2 |
| Peptide No. 296 | QRF-Pen-H-GHFGGLYPCNGP | 3 | 0.15 | 0.96 |
| Peptide No. 195 | QRF-Pen-G-GHFGGLYPCNGP | 7.7 | 0.76 | |
| Peptide No. 213 | QRF-Pen-(NMeAla)-GHFGGLYPCNGP | 5.5 | 1.0 | |

* "NMeAla" = N-methyl alanine

Table 11 provides a listing of Peptide No. 187-derived peptides and peptide analogs, in which substitutions with various amino acid and amino acid derivatives have been generated where there is normally the sequence: Phe-Gly-Sarcosine. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6.

TABLE 11

Analogs of Peptide No. 187 at Phe-Gly-Sar

| | Sequence (SEQ ID NOS 107-119) | $IC_{50}$ μM | $K_D$ (pH 6) μM | $K_D$ pH 7.4 μM |
|---|---|---|---|---|
| Peptide No. 187 | QRF-Pen-TGHF-G-Sar-NMeLeu-YPCNGP | 0.42 | 0.046 | 0.23 |
| Peptide No. 188 | QRF-Pen-TGHF-a-Sar-NMeLeu-YPCNGP | 6.5 | 0.73 | |
| Peptide No. 235 | RF-Pen-TGHF-G-Sar-NMeLeu-YPC | 0.49 | 0.031 | 0.17 |
| Peptide No. 217 | RF-Pen-TGHF-f-Sar-NMeLeu-YPC | 11 | 1.4 | |
| Peptide No. 218 | RF-Pen-TGHF-v-Sar-NMeLeu-YPC | >50 | 13 | |
| Peptide No. 219 | RF-Pen-TGHF-l-Sar-NMeLeu-YPC | 4 | 0.47 | |
| Peptide No. 220 | RF-Pen-TGHF-w-Sar-NMeLeu-YPC | 11 | 2.7 | |
| Peptide No. 240 | RF-Pen-TGHF-t-Sar-NMeLeu-YPC | 71 | 4.8 | |
| Peptide No. 241 | RF-Pen-TGHF-s-Sar-NMeLeu-YPC | 23 | 1.1 | |
| Peptide No. 242 | RF-Pen-TGHF-d-Sar-NMeLeu-YPC | 33 | 2.6 | |
| Peptide No. 243 | RF-Pen-TGHF-n-Sar-NMeLeu-YPC | 29 | 2.1 | |
| Peptide No. 244 | RF-Pen-TGHF-e-Sar-NMeLeu-YPC | 6.4 | 0.58 | |
| Peptide No. 245 | RF-Pen-TGHF-q-Sar-NMeLeu-YPC | 4.5 | 0.36 | |

* "Sar" = sarcosine; "Aib" = aminoisobutyric acid

Table 12 provides a listing of Peptide No. 32-derived peptides and peptide analogs, in which substitutions with various amino acid and amino acid derivatives have been generated where there is normally the sequence: His-Phe-Gly. Column 1 contains the peptide identifier. Column 2 contains the amino acid sequence of the peptides. Column 3 shows the chemical structure of Phe analog side-chain. Column 4 contains the $IC_{50}$ of each peptide as determined by the IgG competition ELISA outlined in Example 4. Column 5 contains the $K_D$ of each peptide as determined at pH 6 by the Biacore analysis outlined in Example 6.

TABLE 12

Analogs of Peptide No. 32 at His-Phe-Gly

| | Sequence (SEQ ID NOS 120-145) | Phe Analog Side-Chain | $IC_{50}$ μM | $K_D$ (pH 6) μM |
|---|---|---|---|---|
| Peptide No. 32 | QRF-Pen-TGH-F-GGLYPCNGP | phenyl | 2 | 0.25 |
| Peptide No. 55 | QRF-Pen-TGH-(4-amino-Phe)-GGLYPCNGP | 4-amino-phenyl (—NH₂) | 13 | 1 |

TABLE 12-continued

Analogs of Peptide No. 32 at His-Phe-Gly

| | Sequence (SEQ ID NOS 120-145) | Phe Analog Side-Chain | IC$_{50}$ μM | K$_D$ (pH 6) μM |
|---|---|---|---|---|
| Peptide No. 56 | QRF-Pen-TGH-(4-methoxy-Phe)-GGLYPCNGP | | 100 | 18 |
| Peptide No. 57 | QRF-Pen-TGH-(pentafluoro-Phe)-GGLYPCNGP | | 120 | 70 |
| Peptide No. 58 | QRF-Pen-TGH-(2-pyridylalanine)-GGLYPCNGP | | 90 | 1.2 |
| Peptide No. 59 | QRF-Pen-TGH-(3-PyridylAla)-GGLYPCNGP | | 60 | 19 |
| Peptide No. 60 | QRF-Pen-TGH-(4-nitro-Phe)-GGLYPCNGP | | >125 | 84 |
| Peptide No. 61 | QRF-Pen-TGH-(1-napthylalanine)-GGLYPCNGP | | 13 | 2.2 |
| Peptide No. 62 | QRF-Pen-TGH-(2-napthylalanine)-GGLYPCNGP | | 90 | 11 |
| Peptide No. 88 | QRF-Pen-TGH-(2-MePhe)-GGLYPCNGP | | 1 | 0.20 |
| Peptide No. 89 | QRF-Pen-TGH-(3-MePhe)-GGLYPCNGP | | 4.1 | 0.67 |
| Peptide No. 90 | QRF-Pen-TGH-(4-MePhe)-GGLYPCNGP | | 1.7 | 0.20 |
| Peptide No. 92 | QRF-Pen-TGH-(homoPhe)-GGLYPCNGP | | 80 | 7.8 |
| Peptide No. 93 | QRF-Pen-TGH-(Cha)-GGLYPCNGP | | 31 | 4.5 |

TABLE 12-continued

Analogs of Peptide No. 32 at His-Phe-Gly

| Sequence (SEQ ID NOS 120-145) | Phe Analog Side-Chain | IC$_{50}$ μM | K$_D$ (pH 6) μM |
|---|---|---|---|
| Peptide No. 94  QRF-Pen-TGH-(PheNHAc)-GGLYPCNGP | (p-acetamidophenyl) | >125 | 270 |
| Peptide No. 95  QRF-Pen-TGH-W-GGLYPCNGP | (indol-3-yl) | 26 | 2.7 |
| Peptide No. 102 QRF-Pen-TGH-(phenylGly)-GGLYPCNGP | (phenyl) | >125 | >250 |
| Peptide No. 103 QRF-Pen-TGH-(Tic)-GGLYPCNGP | X = backbone nitrogen of amino acid | >125 | >250 |
| Peptide No. 104 QRF-Asp-TGH-(2MePhe)-GGLYP-Lys-NGP[1] | (2-methylphenyl) | 11 | |
| Peptide No. 221 RF-Pen-TGH-(2-Cl-Phe)-GGLYPC | (2-chlorophenyl) | 4 | |
| Peptide No. 222 RF-Pen-TGH-(3-Cl-Phe)-GGLYPC | (3-chlorophenyl) | 3.7 | |
| Peptide No. 223 RF-Pen-TGH-(4-Cl-Phe)-GGLYPC | (4-chlorophenyl) | 43 | |
| Peptide No. 224 RF-Pen-TGH-(3,3-Di-Phe)-GGLYPC | (diphenylmethyl) | 32 | |
| Peptide No. 225 RF-Pen-TGH-(4,4-Bi-Phe)-GGLYPC | (4-biphenyl) | >125 | |
| Peptide No. 226 RF-Pen-TGH-(4-t-Butyl-Phe)-GGLYPC | (4-tert-butylphenyl) | >125 | |

TABLE 12-continued

Analogs of Peptide No. 32 at His-Phe-Gly

| Sequence (SEQ ID NOS 120-145) | Phe Analog Side-Chain | IC$_{50}$ μM | K$_D$ (pH 6) μM |
|---|---|---|---|
| Peptide No. 267 RF-Pen-TGH-((D/L)-betamethylPhe)-G-Sar-NMeLeu-YPC | (benzyl side chain) | 16 | |

*"Sar" = sarcosine; "NMeLeu" = N-methyl leucine
[1] SYN927 is cyclized via an amide bond between the Asp and Lys side chains Table 13 provides a listing of various peptides and peptide analogs, in which single amino acids have been substituted with tyrosine. The effect of the substitutions on the binding parameters of these peptides with human FcRn is also provided. Column 1 contains the peptide identifier. Column 2 contains the amino acid sequence of the peptides. Column 3 shows the chemical structure of Tyr analog side-chain. Column 4 contains the IC$_{50}$ of each peptide as determined by the IgG competition ELISA outlined in Example 4. Columns 5 and 6 contain the K$_D$ of each peptide as determined at pH 6 and pH 7.4, respectively, by the Biacore analysis outlined in Example 6.

TABLE 13

Tyrosine Substitutions

| | Sequence (SEQ ID NOS 1 & 146-155) | Tyr Analog Side Chain | IC$_{50}$ μM | K$_D$ (pH 6) μM | K$_D$ pH 7.4 μM |
|---|---|---|---|---|---|
| SEQ ID NO: 1 | QRFCTGHFGGL-Y-PCNGP | 4-hydroxyphenyl (—C$_6$H$_4$—OH) | 26 | 5.1 | 30 |
| Peptide No. 26 | QRFCTGHFGGL-F-PCNGP | phenyl | >125 | 230 | |
| Peptide No. 32 | QRF-Pen-TGHFGGL-Y-PCNGP | 4-hydroxyphenyl (—C$_6$H$_4$—OH) | 2 | 0.25 | 1.2 |
| Peptide No. 63 | QRF-Pen-TGHFGGL-(4-amino-Phe)-PCNGP | 4-aminophenyl (—C$_6$H$_4$—NH$_2$) | 110 | 34 | |
| Peptide No. 64 | QRF-Pen-TGHFGGL-(4-methoxyPhe)-PCNGP | 4-methoxyphenyl (—C$_6$H$_4$—OCH$_3$) | 120 | 31 | |
| Peptide No. 65 | QRF-Pen-TGHFGGL-(pentafluoroPhe)-PCNGP | pentafluorophenyl (—C$_6$F$_5$) | >125 | 72 | |
| Peptide No. 66 | QRF-Pen-TGHFGGL-(2-pyridylAla)-PCNGP | 2-pyridyl | >125 | 120 | |
| Peptide No. 67 | QRF-Pen-TGHFGGL-(3-pyridylAla)-PCNGP | 3-pyridyl | 92 | 34 | |

TABLE 13-continued

Tyrosine Substitutions

| | Sequence (SEQ ID NOS 1 & 146-155) | Tyr Analog Side Chain | $IC_{50}$ μM | $K_D$ (pH 6) μM | $K_D$ pH 7.4 μM |
|---|---|---|---|---|---|
| Peptide No. 68 | QRF-Pen-TGHFGGL-(4-nitro-Phe)-PCNGP | —C₆H₄—NO₂ | 122 | 180 | |
| Peptide No. 87 | QRF-Pen-TGHFGGL-(2-nitro-Tyr)-PCNGP | —C₆H₃(OH)(NO₂) | >125 | 290 | |
| Peptide No. 140 | QRF-Pen-TGHFGGL-(4-fluoro-Phe)-PCNGP | —C₆H₄—F | 26 | 2.2 | 24 |

Table 14 provides a listing of Peptide No. 32-derived peptides and peptide analogs, in which substitutions with various amino acid and amino acid derivatives have been generated where there is normally the sequence: Gly-Leu. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6.

TABLE 14

Analogs of Peptide No. 32 at Gly-Leu

| | Sequence (SEQ ID NOS 156-164) | $IC_{50}$ μM | $K_D$ (pH 6) μM | $K_D$ pH 7.4 μM |
|---|---|---|---|---|
| Peptide No. 32 | QRF-Pen-TGHFGG-L-YPCNGP | 2 | 0.25 | 1.2 |
| Peptide No. 84 | QRF-Pen-TGHFGG-H-YPCNGP | 6.5 | 0.38 | 2.5 |
| Peptide No. 101 | QRF-Pen-TGHFGG-I-YPCNGP | 3.4 | 0.34 | |
| Peptide No. 115 | QRF-Pen-TGHFGG-F-YPCNGP | 4.1 | 0.40 | |
| Peptide No. 116 | QRF-Pen-TGHFGG-W-YPCNGP | 1.7 | 0.17 | |
| Peptide No. 117 | QRF-Pen-TGHFGG-M-YPCNGP | 7.7 | 0.44 | |
| Peptide No. 118 | QRF-Pen-TGHFGG-L-YPCNGP | 8.6 | 0.80 | |
| Peptide No. 237 | RF-Pen-TGHFGG-W-YPC | 2.8 | 0.14 | |
| Peptide No. 238 | QRF-Pen-TGHFG-Sar-W-YPCNGP | 1.0 | 0.068 | |

Table 15 provides a listing of Peptide No. 32-derived peptides and peptide analogs with a substitution of a glycine and a leucine taken together for a dipeptide mimetic where there is normally the sequence: Gly-Leu. Column 1 contains the peptide identifier. Column 2 contains the amino acid sequence of the peptides. Column 3 provides the description for the identity of X in the sequence. Column 4 shows the chemical structure of the analog designated X. Column 5 contains the $IC_{50}$ of each peptide as determined by the IgG competition ELISA outlined in Example 4. Column 6 contains the $K_D$ of each peptide as determined at pH 6 by the Biacore analysis outlined in Example 6.

No. 248 in dichloromethane under nitrogen. Ten molar equivalents of 2,4,6-tri-tert-butylpyridine (Sigma-Aldrich, St. Louis, Mo.) were added to the suspension followed by five molar equivalents of methyl-trifluoromethane-sulfonate (Sigma-Aldrich, St. Louis, Mo.). The reaction was allowed to proceed for 4 hours while rocking and rinsed first with dichloromethane, followed by a rinse with dimethylformamide and finally with dichloromethane again. The peptide was cleaved from the resin, oxidized and purified by HPLC as described above to yield the N-methyl-thiazolium peptide, Peptide No. 269.

TABLE 15

Peptidomimetic Analogs of Peptide No. 32 at Gly-Leu

| | Sequence (SEQ ID NOS 165-167) | X Description | X Structure | $IC_{50}$ μM | $K_D^1$ (pH 6) μM |
|---|---|---|---|---|---|
| Peptide No. 32 | QRF-Pen-TGHFG-X-YPCNGP | Gly-Gly-Leu | | 2.0 | 0.25 |
| Peptide No. 216 | QRF-Pen-TGHFG-X-YPCNGP | L,L-Friedinger's lactam | | 19 | |
| Peptide No. 194 | QRF-Pen-TGHFG-X-YPCNGP | D,L-Friedinger's lactam | | 4.9 | |

Example 8

Synthesis of Peptides Containing Histidine Analogs

Modified histidine analogs (Table 16) were synthesized as described in Example 7 for the synthesis of monomeric peptide disulfides except for the following modified histidine analogs. Peptide No. 259 was synthesized by suspending the resin containing the fully protected peptide analogous to Peptide No. 99 in neat methyl iodide for 15 hours. The resin washed with dichloromethane and the peptide was cleaved from the resin, oxidized and purified by HPLC as described above to yield the mono-methylated histidine peptide Peptide No. 259.

Peptide No. 260 was synthesized by suspending the resin containing the fully protected peptide analogous to Peptide No. 99 in neat methyl iodide for 72 hours. The resin washed with dichloromethane and the peptide was cleaved from the resin, oxidized and purified by HPLC as described above to yield the di-methylated histidine peptide Peptide No. 260.

Peptide No. 269 was synthesized by suspending the resin containing the fully protected peptide analogous to Peptide Peptide No. 271 was synthesized by treating the peptide Peptide No. 261 with 30 equivalents of copper sulfate, 30 equivalents of ascorbic acid and 10 equivalents of sodium azide in a solution of 100 mM sodium phosphate buffer at pH 7.5 with 33% ethanol, 10% acetonitrile, 10% N,N-dimethylformamide. The reaction proceeded for 2 hours and the mixture was purified by HPLC as described above to yield the 1,2,3-triazole side-chain containing peptide Peptide No. 271.

Table 16 provides a listing of various peptides and peptide analogs, in which single amino acids have been substituted for histidine. The effect of the substitutions on the binding parameters of these peptides with human FcRn is also provided. Column 1 contains the peptide identifier. Column 2 contains the amino acid sequence of the peptides. Column 3 shows the chemical structure of H is analog side-chain. Column 4 contains the $IC_{50}$ of each peptide as determined by the IgG competition ELISA outlined in Example 4. Columns 5 and 6 contain the $K_D$ of each peptide as determined at pH 6 and pH 7.4, respectively, by the Biacore analysis outlines in Example 6.

TABLE 16

| | | | | $K_D$ | $K_D$ |
| | | | | (pH 6) | pH 7.4 |
| | Sequence | His Analog | $IC_{50}$ | | |
| | (SEQ ID NOS 1 & 168-196) | Side Chain | μM | μM | μM |
|---|---|---|---|---|---|
| Histidine Substitutions | | | | | |
| SEQ ID NO: 1 | QRFCTG-H-FGGLYPCNGP | 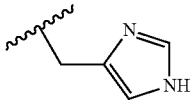 | 26 | 5.1 | 30 |
| Peptide No. 36 | QRFCTG-Dab-FGGLYPCNGP | 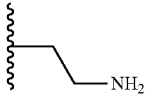 | >125 | 211 | |
| Peptide No. 32 | QRF-Pen-TG-H-FGGLYP-C-NGP | 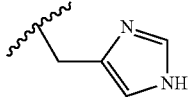 | 2 | 0.25 | 1.2 |
| Peptide No. 91 | QRF-Pen-TG-Thz-FGGLYPCNGP | 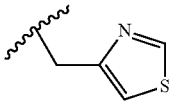 | 44 | 7.9 | 21 |
| Peptide No. 109 | QRF-Pen-TG-Dap-FGGLYPCNGP | 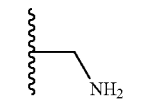 | >125 | >100 | |
| Peptide No. 297 | QRF-Pen-TG-Dap(Guanyl)-FGGLYPCNGP | 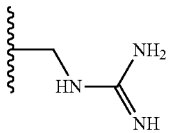 | 54 | 13 | 16 |
| Peptide No. 138 | QRF-Pen-TG-(1Me)His-FGGLYPCNGP | 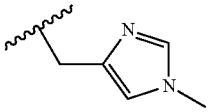 | 3.4 | 0.74 | 14 |
| Peptide No. 139 | QRF-Pen-TG-Dab-FGGLYPCNGP | 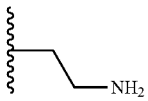 | 64 | 7.3 | 8.4 |
| Peptide No. 192 | RF-Pen-TG-NMeHis-FGGLYPC | 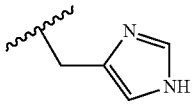 | >250 | nd | nd |
| Peptide No. 248 | RF-Pen-TG-Thz-FG-Sar-NMeL-YPC | 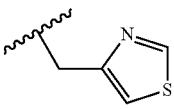 | 1.6 | .84 | 1.1 |
| Peptide No. 249 | RF-Pen-TG-2PyridylAla-FG-Sar-NMeL-YPC | 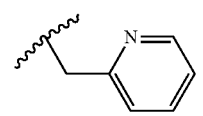 | 6.2 | .33 | 0.41 |
| Peptide No. 250 | RF-Pen-TG-3PyridylAla-FG-Sar-NMeL-YPC | 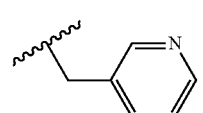 | 1.2 | .064 | 0.26 |

TABLE 16-continued

| | Sequence (SEQ ID NOS 1 & 168-196) | His Analog Side Chain | IC$_{50}$ μM | K$_D$ (pH 6) μM | K$_D$ pH 7.4 μM |
|---|---|---|---|---|---|
| Peptide No. 251 | RF-Pen-TG-ThienylAla-FG-Sar-NMeL-YPC | 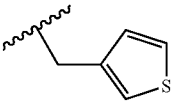 | 45 | 2 | 3 |
| Peptide No. 253 | RF-Pen-TG-Dab-FG-Sar-NMeL-YPC | 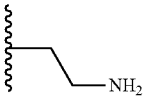 | 16 | 1.2 | 1.2 |
| Peptide No. 254 | RF-Pen-TG-Orn-FG-Sar-NMeL-YPC |  | 12 | 1.3 | 1.2 |
| Peptide No. 255 | RF-Pen-TG-Lys-FG-Sar-NMeL-YPC | 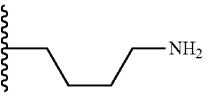 | 40 | 1.3 | 1.1 |
| Peptide No. 256 | RF-Pen-TG-Arg-FG-Sar-NMeL-YPC | 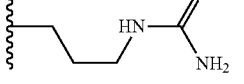 | 5.5 | 0.5 | 0.5 |
| Peptide No. 257 | RF-Pen-TG-4GuanylPhe-FG-Sar-NMeL-YPC | 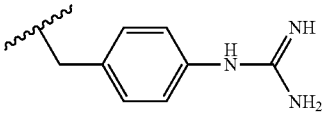 | 1.7 | 0.074 | 0.073 |
| Peptide No. 258 | RF-Pen-TG-4aminoPhe-FG-Sar-NMeL-YPC | 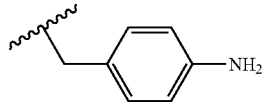 | 4.6 | 0.22 | 1.1 |
| Peptide No. 259 | RF-Pen-TG-His(Me)-FGGLYPC | 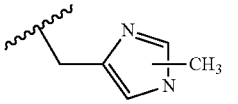 | 2.9 | 0.14 | 0.38 |
| Peptide No. 260 | RF-Pen-TG-His(Me)2-FGGLYPC | 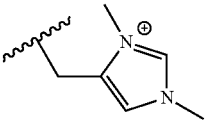 | 4.4 | 0.19 | 0.46 |
| Peptide No. 261 | RF-Pen-TG-PropargylGly-FG-Sar-NMeLeu-YPC | 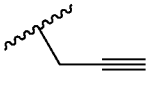 | 160 | 13 | 11 |
| Peptide No. 262 | RF-Pen-TG-(2-PyrrolidinylAla)-FG-Sar-NMeLeu-YPC | 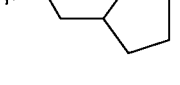 | 150 | 8.4 | 13 |
| Peptide No. 263 | RF-Pen-TG-(3-PiperidyalAla)-FG-Sar-NMeLeu-YPC | 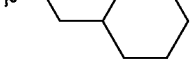 | 6.3 | 0.66 | 0.86 |

TABLE 16-continued

Histidine Substitutions

| | Sequence (SEQ ID NOS 1 & 168-196) | His Analog Side Chain | IC$_{50}$ µM | K$_D$ (pH 6) µM | K$_D$ pH 7.4 µM |
|---|---|---|---|---|---|
| Peptide No. 264 | RF-Pen-TG-(4-PiperidylAla)-FG-Sar-NMeLeu-YPC | 4-piperidylmethyl | 85 | 5.2 | 6.4 |
| Peptide No. 265 | RF-Pen-TGFFG-Sar-NMeLeu-YPC | benzyl | 27 | 3.3 | 4.2 |
| Peptide No. 266 | RF-Pen-TGAFG-Sar-NMeLeu-YPC | —CH$_3$ | >100 | 9.9 | 13 |
| Peptide No. 268 | RF-Pen-TG-(4-PyridylAla)-FG-Sar-NMeLeu-YPC | 4-pyridylmethyl | 1.3 | 0.067 | 0.28 |
| Peptide No. 269 | RF-Pen-TG-Thz(Me)-FG-Sar-NMeL-YPC-CONH2 | N-methylthiazolium-methyl | 2.4 | 0.11 | 0.11 |
| Peptide No. 271 | RF-Pen-TG-triazolylAla-FG-Sar-NMeL-YPC | triazolylmethyl | 5.7 | 0.32 | 0.36 |

Example 9

Synthesis of Peptides Containing Peptidomimetic Analogs of Gly-Gly

All of the Gly-Gly amino acid mimetics (Table 17) were incorporated as their Fmoc-amino protected amino acids and were commercially available unless otherwise noted (Chem-Impex, Wood Dale, Ill.). Peptides containing 3(R)-3-amino-2-oxo-1-piperidine-acetic were synthesized by incorporating the N-Fmoc derivative of 3(R)-3-amino-2-oxo-1-piperidine-acetic acid into Peptide No. 227 according to the protocol described by R. M. Freidinger et. al., *J. Org. Chem.* 47: 104-109 (1982). Peptides containing 3(R)-3-amino-2-oxo-1-pyrrolidine acetic acid were synthesized by incorporating the N-Fmoc derivative of 3(R)-3-amino-2-oxo-1-pyrrolidine acetic acid into Peptide No. 214 according to the protocol described by R. M. Freidinger et. al., *J. Org. Chem.* 47:104-109 (1982). Peptides containing the 5,5-bicyclic dipeptide mimic were synthesized by incorporating the 5,5-bicyclic dipeptide mimic into Peptide No. 197 or Peptide No. 198 according to the protocol described by N. L. Subasinghe et. al., *J. Med. Chem.* 36: 2356-2361 (1993) with the exception that all D-amino acids were used. Peptides containing the 6,5-bicyclic dipeptide mimic were synthesized by incorporating the 6,5-bicyclic dipeptide mimic into Peptide No. 204 according to the protocol described by F. A. Etzkorn et. al., *J. Am. Chem. Soc.* 116: 10412 (1994) with the exception that all D-amino acids were used. Peptides containing the (D,L)-Freidinger's lactam were synthesized by incorporating the (D,L)-Freidinger's lactam into Peptide No. 216 according to the protocol described by R. M. Freidinger et al., *J. Org. Chem.* 47: 104-109 (1982) with the exception that L-methionine was used instead of D-methionine.

Table 17 provides a listing of SEQ ID NO:1-derived peptides and peptide analogs in which substitutions with various amino acid and amino acid derivatives have been generated where there are normally two adjacent glycines (Gly-Gly). Column 1 contains the peptide identifier. Column 2 contains the amino acid sequence of the peptides. Column 3 contains the IC$_{50}$ of each peptide as determined by the IgG competition ELISA outlined in Example 4. Columns 4 and 5 contain the K$_D$ of each peptide as determined at pH 6 and pH 7.4, respectively, by the Biacore analysis outlined in Example 6.

TABLE 17

Analogs of SEQ ID NO:1 at Gly-Gly

| | Sequence (SEQ ID NOS 197-201) | IC$_{50}$ µM | K$_D$ (pH 6) µM | K$_D$ pH 7.4 µM |
|---|---|---|---|---|
| SEQ ID NO:1 | QRFCTGHF<u>GG</u>LYPCNGP | 26 | 5.1 | 30 |
| Peptide No. 22 | QRFCTGHF-<u>a</u>-GLYPCNGP | 48 | 10 | 137 |
| Peptide No. 23 | QRFCTGHFG-<u>a</u>-LYPCNGP | 57 | 12 | 184 |
| Peptide No. 24 | QRFCTGHF-<u>a</u>-<u>a</u>-LYPCNGP | 69 | 22 | >250 |
| Peptide No. 25 | QRFCGHF-<u>betaAla</u>-LYPCNGP | >125 | >250 | nd |
| Peptide No. 35 | QRFCTGHF-<u>Apa</u>-LYPCNGP | >125 | 220 | nd |

\* "beta-Ala" = beta-alanine; "Apa" = 5-aminopentanoic acid

Table 18 provides a listing of Peptide No. 99-derived peptides and peptide analogs with a substitution of two glycines taken together for a peptidomimetic analog where there is normally the sequence: Gly-Gly. Column 1 contains the peptide identifier. Column 2 contains the amino acid sequence of the peptides. Column 3 provides the description for the identity of the peptidomimetic analog designated as X in the sequence. Column 4 shows the chemical structure of the analog designated X. Column 5 contains the IC$_{50}$ of each peptide as determined by the IgG competition ELISA outlined in Example 4. Column 6 contains the K$_D$ of each peptide as determined at pH 6 by the Biacore analysis outlined in Example 6.

TABLE 18

Peptidomimetic Analogs of Peptide No. 99 at Gly-Gly

| | Sequence (SEQ ID NOS 202-219) | X Description | X Structure | IC$_{50}$ µM | K$_D$ (pH 6) µM |
|---|---|---|---|---|---|
| Peptide No. 99 | RF-Pen-TGHF-X-LYPC | Gly-Gly | 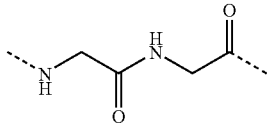 | 2.0 | 0.17 |
| Peptide No. 134 | RF-Pen-TGHF-X-LYPC | 4-aminomethyl-benzoic acid | 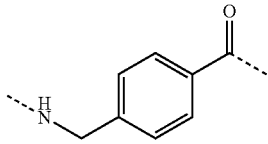 | >125 | |
| Peptide No. 135 | RF-Pen-TGHF-X-LYPC | (3-aminomethyl)-benzoic acid | 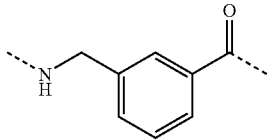 | 57 | |
| Peptide No. 136 | RF-Pen-TGHF-X-LYPC | 4-aminophenyl acetic acid | 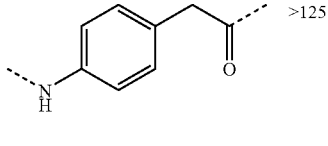 | >125 | |
| Peptide No. 137 | RF-Pen-TGHF-X-LYPC | 3-aminophenyl acetic acid | 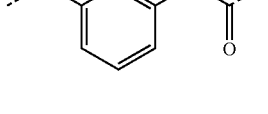 | 14 | |

TABLE 18-continued

Peptidomimetic Analogs of Peptide No. 99 at Gly-Gly

| | Sequence (SEQ ID NOS 202-219) | X Description | X Structure | IC$_{50}$ μM | K$_D$ (pH 6) μM |
|---|---|---|---|---|---|
| Peptide No. 178 | RF-Pen-TGHF-X-LYPC | 3-amino-2-oxo-1-piperidine-acetic acid | | 0.66 | 0.16 |
| Peptide No. 179 | RF-Pen-TGHF-X-LYPC | 3-amino-2-oxo-1-piperidine-acetic acid | | 7.2 | 0.67 |
| Peptide No. 193 | RF-Pen-TGHF-X-LYPC | 3(S)-3-amino-2-oxo-1-piperidine-acetic acid | | 7.3 | |
| Peptide No. 80 | RF-Pen-TGHF-X-LYPC | 3-amino-N-1-carboxymethyl-2,3,4,5-tetrahydro-1H-[1]-benzazepine-2-one | | 159 | |
| Peptide No. 181 | RF-Pen-TGHF-X-LYPC | 3-amino-N-1-carboxymethyl-2,3,4,5-tetrahydro-1H-[1]-benzazepine-2-one | | 1.2 | |
| Peptide No. 197 | RF-Pen-TGHF-X-LYPC | 5,5-bicyclic dipeptide mimic | | 13 | 0.99 |
| Peptide No. 198 | RF-Pen-TGHF-X-LYPC | 5,5-bicyclic dipeptide mimic | | 23 | |
| Peptide No. 204 | RF-Pen-TGHF-X-LYPC | 6,5-bicyclic dipeptide mimic | | 2.2 | 0.32 |

TABLE 18-continued

Peptidomimetic Analogs of Peptide No. 99 at Gly-Gly

| | Sequence (SEQ ID NOS 202-219) | X Description | X Structure | IC$_{50}$ µM | K$_D$ (pH 6) µM |
|---|---|---|---|---|---|
| Peptide No. 205 | RF-Pen-TGHF-X-LYPC | 3(R)-3-amino-2-oxo-1-azepine acetic acid | | 0.64 | 0.103 |
| Peptide No. 214 | RF-Pen-TGHF-X-LYPC | 3(R)-3-amino-2-oxo-1-pyrrolidine acetic acid | | 2.3 | 0.28 |
| Peptide No. 227 | RF-Pen-TGHF-X-NMeLeu-YPC | 3(R)-3-amino-2-oxo-1-piperidine-acetic acid | | 0.53 | 0.043 |
| Peptide No. 228 | RF-Pen-NMeAla-GHF-X-NMeLeu-YPC | 3(R)-3-amino-2-oxo-1-piperidine-acetic acid | | 1.1 | 0.145 |
| Peptide No. 239 | RF-Pen-TGHF-X-NMeLeu-YPC | 3(R)-3-amino-2-oxo-1-azepine acetic acid | | 0.62 | 0.044 |

Example 10

Synthesis of Peptides Cyclized Via A Lactam Bridge

Lactam cyclized peptides (Table 19) were synthesized by solid-phase peptide synthesis as outlined above in Example 7 with the exception that the following amino acids were used as substitutes for various cysteines: Fmoc-Lys(Aloc)-OH, Fmoc-Orn(Aloc)-OH, Fmoc-Dab(Aloc)-OH and Fmoc-Dap(Aloc)-OH, Fmoc-Glu(OAllyl)-OH and Fmoc-Asp(OAllyl)-OH (Bachem, Torrance, Calif.). Following the completion of the process to generate fully protected peptides on resin, the resin was swollen in dichloromethane, purged with nitrogen and treated with 0.1 molar equivalents of tetrakis-(triphenylphosphine)palladium(0) (Sigma-Aldrich, St. Louis, Mo.) and 30 molar equivalents of phenylsilane (Sigma-Aldrich, St. Louis, Mo.) and the reaction was allowed to proceed for three hours. The resin washed first with dichloromethane, with DMF and finally five additional times with a solution of 1% (v/v) triethylamine and 1% (w/v) diethyldithiocarbamic acid in DMF. An additional washing step with DMF was followed by treatment of the resin with benzotriazole-1-yl-oxy-tris-pyrrolidino-phosphonium hexafluorophosphate (PyBOP) (Novabiochem, San Diego Calif.) and DIEA for 16 hours. The peptides were cleaved from the resin and purified as described above in Example 7.

Table 19 provides a listing of various peptides of the invention with amino acid substitutions of cysteine residues for amino acids and amino acid analogs that would allow for the cyclization of the respective peptides via a lactam bridge. The impact of the substitutions on the binding parameters of these peptides with human FcRn is also provided. Column 1 contains the peptide identifier. Column 2 contains the amino acid sequence of the peptides. Column 3 contains the IC$_{50}$ of each peptide as determined by the IgG competition ELISA outlined in Example 4. Columns 4 and 5 contain the K$_D$ of each peptide as determined at pH 6 and pH 7.4, respectively, by the Biacore analysis outlined in Example 6.

TABLE 19

Lactam Cyclized Peptides

| | Sequence[1] (SEQ ID NOS 220-246) | IC$_{50}$ μM | K$_D$ (pH 6) μM | K$_D$ pH 7.4 μM |
|---|---|---|---|---|
| Peptide No. 38 | QRF-<u>Asp</u>-TGHFGGLYP-<u>Dab</u>-NGP | 68 | 17 | 150 |
| Peptide No. 39 | QRF-<u>Asp</u>-TGHFGGLYP-<u>Lys</u>-NGP | 10 | 1.2 | 12 |
| Peptide No. 72 | QRF-<u>Dab</u>-TGHFGGLYP-<u>Glu</u>-NGP | 81 | 4.8 | nd |
| Peptide No. 73 | QRF-<u>Lys</u>-TGHFGGLYP-<u>Glu</u>-NGP | 33 | 1.2 | nd |
| Peptide No. 76 | QRF-<u>Glu</u>-TGHFGGLYP-<u>Lys</u>-NGP | 100 | 27 | 320 |
| Peptide No. 77 | QRF-<u>Glu</u>-TGHFGGLYP-<u>Dab</u>-NGP | 86 | 22 | 210 |
| Peptide No. 78 | QRF-<u>Glu</u>-TGHFGGLYP-<u>Dap</u>-NGP | 71 | 9.6 | 81 |
| Peptide No. 79 | QRF-<u>Asp</u>-TGHFGGLYP-<u>Dap</u>-NGP | 32 | 4.5 | 30 |
| Peptide No. 80 | QRF-<u>Lys</u>-TGHFGGLYP-<u>Asp</u>-NGP | 60 | 10 | 52 |
| Peptide No. 81 | QRF-<u>Dab</u>-TGHFGGLYP-<u>Asp</u>-NGP | 31 | 8.4 | 45 |
| Peptide No. 85 | QRF-<u>Asp</u>-TGHFGGLYP-<u>Orn</u>-NGP | 16 | 2.7 | nd |
| Peptide No. 86 | QRF-<u>Glu</u>-TGHFGGLYP-<u>Orn</u>-NGP | 80 | 15 | nd |
| Peptide No. 107 | QRF-<u>Asp</u>-TGHFGGLY-<u>Lys</u>-NGP | >125 | >250 | nd |
| Peptide No. 105 | QRF-<u>Asp</u>-TGHFG-a-LYP-<u>Lys</u>-NGP | 12 | 2.1 | nd |
| Peptide No. 106 | QRF-<u>Asp</u>-TGHF-a-GLYP-<u>Lys</u>-NGP | 17 | 3.7 | nd |
| Peptide Np. 123 | <u>Asp</u>-TGHFGGLYP-<u>Lys</u>-NGP | 47 | | |
| Peptide No. 124 | F-<u>Asp</u>-TGHFGGLYP-<u>Lys</u>-NGP | 22 | | |
| Peptide No. 125 | RF-<u>Asp</u>-TGHFGGLYP-<u>Lys</u>-NGP | 9.4 | | |
| Peptide No. 126 | QRF-<u>Asp</u>-TGHFGGLYP-<u>Lys</u>-NGP | 13 | | |
| Peptide No. 127 | QRF-<u>Asp</u>-TGHFGGLYP-<u>Lys</u>-N | 7.6 | | |
| Peptide No. 128 | QRF-<u>Dap</u>-TGHFGGLYP-<u>Asp</u>-NGP | 120 | | |
| Peptide No. 129 | QRF-<u>Dap</u>-TGHFGGLYP-<u>Glu</u>-NGP | >125 | | |
| Peptide No. 130 | QRF-<u>Orn</u>-TGHFGGLYP-<u>Asp</u>-NGP | 120 | | |
| Peptide No. 131 | QRF-<u>Orn</u>-TGHFGGLYP-<u>Glu</u>-NGP | 30 | | |
| Peptide No. 132 | RF-<u>Asp</u>-TGHFGGLYP-<u>Lys</u> | 11 | 0.90 | |
| Peptide No. 133 | QRF-<u>Asp</u>-TGHFGGLYP-<u>Lys</u> | 13 | 0.90 | |
| Peptide No. 159 | QRF-<u>Asp</u>-TGHFG-p-LYP-<u>Lys</u>-NGP | 15 | 1.2 | |

[1] There is an amide bond between the side-chains of the underlined amino acids; Dab = 1,3-diaminobutyric acid; Dap = 1,2-diaminoproprionic acid; Orn = ornithine

Example 11

Synthesis of Linear Peptide Analogs

Linear peptide analogs were synthesized as described above in Example 7, with the exception that disulfide-forming amino acids were substituted as set forth in Tables 20 and 21.

Table 20 provides a listing of SEQ ID NO:1-derived linear peptides and peptide analogs of the invention. The binding parameters of these peptides with human FcRn is also provided. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6.

TABLE 20

Linear Analogs of SEQ ID NO:1

| | Sequence[1] (SEQ ID NOS 1 & 247-273) | $IC_{50}$ μM | $K_D$ (pH 6) μM | $K_D$ pH 7.4 μM |
|---|---|---|---|---|
| SEQ ID NO:1 | QRFCTGHFGGLYPCNGP | 26 | 5.1 | 30 |
| Peptide No. 71 | QRF-S-TGHFGGLYP-S-NGP | >125 | 230 | |
| Peptide No. 156 | QRF-V-TGHF-p-p-LYP-A-NGP | >250 | | |
| Peptide No. 157 | QRF-V-TGHF-G-p-LYP-A-NGP | 195 | 16 | |
| Peptide No. 58 | QRF-V-TGHF-p-G-LYP-A-NGP | >250 | | |
| Peptide No. 162 | QRF-L-TGHF-G-p-LYP-A-NGP | >250 | | |
| Peptide No. 163 | QRF-I-TGHF-G-p-LYP-A-NGP | >250 | | |
| Peptide No. 164 | QRF-F-TGHF-G-p-LYP-A-NGP | >250 | | |
| Peptide No. 165 | QRF-Y-TGHF-G-p-LYP-A-NGP | >250 | | |
| Peptide No. 166 | QRF-W-TGHF-G-p-LYP-A-NGP | >250 | | |
| Peptide No. 167 | QRF-V-TGHF-G-p-LYP-A-NGP | 93 | | |
| Peptide No. 168 | QRF-V-TGHF-G-p-LYP-L-NGP | 100 | | |
| Peptide No. 169 | QRF-V-TGHF-G-p-LYP-I-NGP | 72 | 15 | |
| Peptide No. 170 | QRF-V-TGHF-G-p-LYP-F-NGP | >250 | | |
| Peptide No. 171 | QRF-V-TGHF-G-p-LYP-Y-NGP | 150 | | |
| Peptide No. 172 | QRF-V-TGHF-G-p-LYP-W-NGP | 150 | | |
| Peptide No. 173 | QRF-V-TGHF-G-p-V-YP-A-NGP | >250 | | |
| Peptide No. 174 | QRF-V-TGHF-G-p-I-YP-A-NGP | 94 | | |
| Peptide No. 175 | QRF-V-TGHF-G-p-F-YP-A-NGP | 200 | | |
| Peptide No. 176 | QRF-V-TGHF-G-p-Y-YP-A-NGP | 230 | | |
| Peptide No. 177 | QRF-V-TGHF-G-p-W-YP-A-NGP | 52 | 5.8 | 96 |
| Peptide No. 190 | QRF-V-TGHF-G-p-W-YP-I-NGP | 49 | 4.2 | |
| Peptide No. 209 | RF-V-TGHF-G-p-W-YP | >125 | | |
| Peptide No. 210 | RF-V-TGHF-G-p-W-YP-A-NGP | 100 | 10 | |

TABLE 20-continued

Linear Analogs of SEQ ID NO:1

| | Sequence[1]<br>(SEQ ID NOS 1 & 247-273) | IC$_{50}$<br>μM | K$_D$<br>(pH 6)<br>μM | K$_D$<br>pH 7.4<br>μM |
|---|---|---|---|---|
| Peptide No. 211 | F-V-TGHF-G-p-W-YPA | 100 | 8 | |
| Peptide No. 212 | V-TGHF-G-p-W-YP-A | >250 | | |
| Peptide No. 236 | RF-V-TGHF-G-Sar-NMeLeu-YP-A | 37 | 1.85 | 9 |
| Peptide No. 246 | RF-V-TGHF-G-p-W-YPA | 60 | 3.6 | |

[1]"Sar" = sarcosine; "NMeLeu" = N-methyl leucine

Table 21 provides a listing of Peptide No. 236-derived peptides where various peptidomimetic analogs have been substituted where there is normally a Glycine-Sarcosine sequence (Gly-Sar). Column 1 contains the peptide identifier. Column 2 contains the amino acid sequence of the peptides. Column 3 provides the description for the identity of the peptidomimetic analog designated as X in the sequence. Column 4 shows the chemical structure of the peptidomimetic analog designated X. Column 5 contains the IC$_{50}$ of each peptide as determined by the IgG competition ELISA outlined in Example 4. Column 6 contains the K$_D$ of each peptide as determined at pH 6 by the Biacore analysis outlined in Example 6.

TABLE 21

Linear Analogs of Peptide No. 236 with Gly-Gly peptidomimetics

| | Sequence<br>(SEQ ID NOS 274-283) | X<br>Description | X<br>Structure | IC$_{50}$<br>μM | K$_D$<br>(pH 6)<br>μM |
|---|---|---|---|---|---|
| Peptide No. 236 | RF-V-TGHF-X-NMeLeu-YPA | Gly-Sar | | 37 | 1.85 |
| Peptide No. 182 | RF-V-TGHF-X-LYPA | 3-amino-2-oxo-1-piperidine-acetic acid | | 38 | 3.3 |
| Peptide No. 183 | RF-V-TGHF-X-LYPA | 3-amino-2-oxo-1-piperidine-acetic acid | | >250 | |
| Peptide No. 184 | RF-V-TGH F-X-LYPA | 3-amino-N-1-carboxymethyl-2,3,4,5-tetrahydro-1H-[1]-benzazepine-2-one | | >250 | |
| Peptide No. 185 | RF-V-TGH F-X-LYPA | 3-amino-N-1-carboxymethyl-2,3,4,5-tetrahydro-1H-[1]-benzazepine-2-one | | 57 | 3.1 |

TABLE 21-continued

Linear Analogs of Peptide No. 236 with Gly-Gly peptidomimetics

| | Sequence (SEQ ID NOS 274-283) | X Description | X Structure | IC$_{50}$ µM | K$_D$ (pH 6) µM |
|---|---|---|---|---|---|
| Peptide No. 186 | RF-V-TGHF-X-LYPA | 3-aminophenyl acetic acid | | >250 | |
| Peptide No. 191 | QRF-V-TGHF-X-WYPINGP | 3-amino-2-oxo-1-piperidine-acetic acid | | nd | 333 |
| Peptide No. 206 | RF-V-TGHF-X-LYPA | 5,5-bicyclic dipeptide mimic | | >250 | |
| Peptide No. 207 | RF-V-TGHF-X-LYPA | 6,5-bicyclic dipeptide mimic | | >125 | 20 |
| Peptide No. 208 | RF-V-TGHF-X-LYPA | 3(R)-3-amino-2-oxo-1-azepine acetic acid | | 23 | 2.3 |

*"Sar" = sarcosine; "NMeLeu" = N-methyl leucine

Example 12

Synthesis of Peptide Dimers Via Reductive Alkylation

Peptide dimers (Table 22) were generated by reductive alkylation of a peptide aldehyde and a peptide amino (N) or carboxy (C) terminal amine.

Peptide N-terminal amines were synthesized as described above in Example 7 for the synthesis of monomeric peptide disulfides.

Peptide C-terminal amines were also synthesized as described above in Example 7 for the synthesis of monomeric peptide disulfides, except that 1,2-diaminoethane resin (Novabiochem, San Diego, Calif.) was used in the synthesis step. Consequently, cleavage from the resin resulted in a C-terminal ethyl amine.

Peptide N-terminal aldehydes (FIG. 2) were synthesized by reacting the unprotected amine of the N-terminal amino acid with 5 equivalents of succinnic anhydride (Sigma-Aldrich, St. Louis, Mo.) in the presence of DIEA in DMF for 2 hours. A subsequent reaction with 2,2-dimethyl-1,3-dioxolane methamine (Sigma-Aldrich, St. Louis, Mo.) in the presence of PyBOP and DIEA for 2 hours yielded the protected diol resin. Then, cleavage of the crude peptide from the resin, followed by cysteine oxidation and purification as described above in Example 7 for the synthesis of monomeric peptide disulfides, yielded the peptide diol. The diol was dissolved in 33% acetic acid followed by 2 equivalents of sodium periodate (Sigma-Aldrich, St. Louis, Mo.) was added and the reaction was allowed to proceed for 5 minutes. The reaction mixture was quenched with 20 equivalents (with respect to the diol) of ethylene glycol (Sigma-Aldrich, St. Louis, Mo.) and after ten minutes, the crude reaction mixture was diluted 3-fold with water and purified over a C18 Sep-Pak column (Waters Corp., Milford, Mass.) using an increasing gradient of acetonitrile in water containing 0.1% TFA. The peptide aldehyde was lyophilized and subjected to analysis by mass spectroscopy (Mariner ES-MS) following liquid chromatography (Applied Biosystems, Foster City, Calif.) as described in Example 7.

Peptide C-terminal aldehydes were synthesized as described above in Example 7 for the synthesis of monomeric peptide disulfides, except that Fmoc-1-amino-2,3-propanediol-2'-chlorotrityl resin (Novabiochem, San Diego, Calif.) was used instead of Rink amide resin. Therefore the resulting peptide resin contained a masked C-terminal diol. Upon cleavage from the resin, the diol was oxidized to an aldehyde as described above for N-terminal aldehydes.

Peptide monomers to synthesize lactam-cyclized peptides such as Peptide No. 275, were synthesized according to the method described above in Example 10 to synthesize peptides cyclized by a lactam bridge, whereby the Asp-Lys cyclization was performed on the resin, prior to cleavage from the resin.

Figure 3:
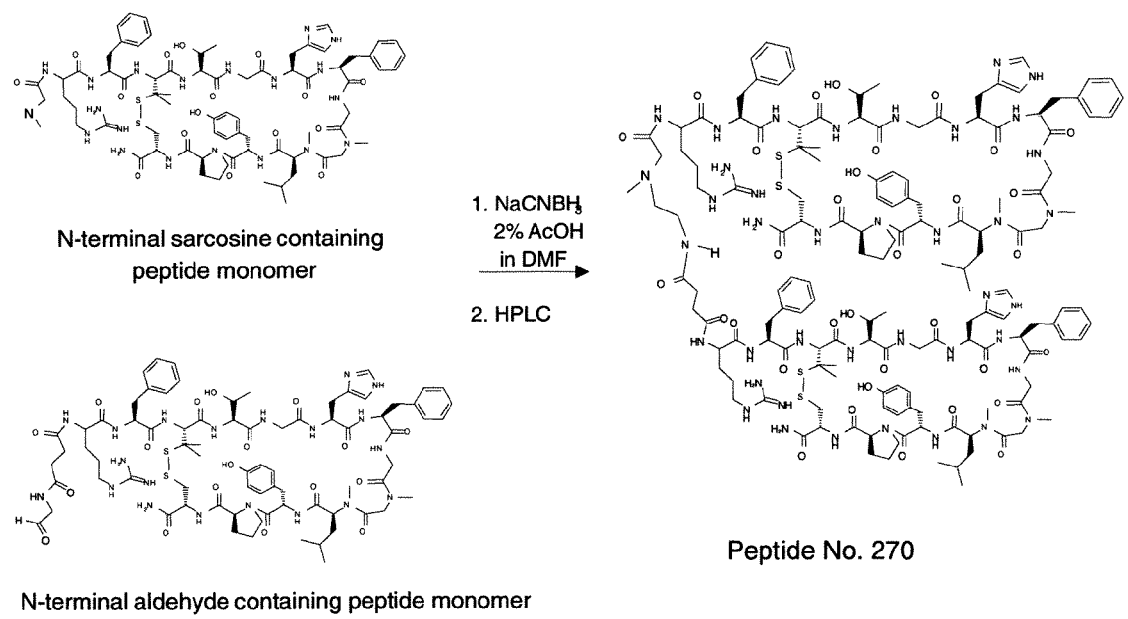
FIG. 3 shows an overview of the synthesis of peptide dimers by reductive alkylation. The synthesis of Peptide No. 270 is shown as an illustrative example.

The peptide dimers were synthesized (FIG. 3) by reacting one equivalent of peptide aldehyde with one equivalent of amine-containing peptide at a concentration of 40 mg/ml in DMF containing 2% acetic acid. After 60 min., 2 equivalents of sodium cyanoborohydride (Sigma-Aldrich, St. Louis, Mo.) were added and the reaction was allowed to shake for 1 hour. The reaction mixture was diluted 10-fold with water and purified by HPLC and analyzed by mass spectroscopy (Mariner ES-MS) following liquid chromatography (Applied Biosystems, Foster City, Calif.) as described in Example 7.

Table 22 provides a listing of dimeric peptides of the invention that were synthesized by reductive alkylation. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6. Column 6 contains the $IC_{50}$ of each peptide as determined by competitive IgG binding FACS analysis as outlined in Example 5.

TABLE 22

Dimers and Trimers Synthesized by Reductive Alkylation

| | Sequence[1] | $IC_{50}$ nM | $K_D$ pH 6 nM | $K_D$ pH 7.4 nM | $IC_{50}$ nM FACS |
|---|---|---|---|---|---|
| Peptide No. 276 | [RFCTGHFGGLYPC] / [RFCTGHFGGLYPC] | 3700 | 56 | | 12,900 |
| Peptide No. 215 | [QRF-Pen-TGHFGpLYPCNGP] / [QRF-Pen-TGHFGpLYPCNGP] | | 30 | 6.6 | |
| Peptide No. 230 | [RF-Pen-TGHF-X-NMeLeu-YPC] / [RF-Pen-TGHF-X-NMeLeu-YPC] | 7.2 | <0.5 | 0.46 | |
| Peptide No. 231 | [RF-Pen-NMeAla-GHF-X-NMeLeu-YPC] / [RF-Pen-NMeAla-GHF-X-NMeLeu-YPC] | | 30 | 2.9 | |

TABLE 22-continued

Dimers and Trimers Synthesized by Reductive Alkylation

| Sequence[1] | IC$_{50}$ nM | K$_D$ pH 6 nM | K$_D$ pH 7.4 nM | IC$_{50}$ nM FACS |
|---|---|---|---|---|
| Peptide No. 247 (structure: trimer with R-F-Pen-T-G-H—F-G-Sar-NMeLeu-Y-P—C branches) | 6 | | | |
| Peptide No. 270 (structure: dimer with [RF-Pen-TGHFG-Sar-NMeLeu-YPC] branches) | 2.6 | <0.5 | <0.8 | 4 |
| Peptide No. 272 (structure: dimer with [RF-Pen-TGHFG-Sar-NMeLeu-YPC] branches) | 2.8 | <0.5 | <0.8 | 5 |
| Peptide No. 273 (structure: dimer with [RF-Pen-TGHFG-Sar-NMeLeu-YPC] branches) | 2.1 | <0.5 | <0.9 | 4 |

TABLE 22-continued

Dimers and Trimers Synthesized by Reductive Alkylation

| Sequence[1] | IC$_{50}$ nM | K$_D$ pH 6 nM | K$_D$ pH 7.4 nM | IC$_{50}$ nM FACS |
|---|---|---|---|---|
| Peptide No. 274: branched structure with [RF-Pen-TG-4GuPhe-FG-Sar-NMeLeu-YPC] units linked via succinyl/ethylenediamine linker | | 17 | | |
| Peptide No. 277: [RF-Pen-TGHFG-Sar-NMeLeu-YPCG] linked to [RF-Pen-TGHFG-Sar-NMeLeu-YPC] via N-methyl ethylenediamine-glycyl linker | | 6.3 | | |
| Peptide No. 278: two [RF-Pen-TGHFG-Sar-NMeLeu-YPCG] units linked via ethylenediamine | | 4.4 | | |
| Peptide No. 275: two [RF-Asp-TGHFG-Sar-NMeLeu-YP-Lys] units linked via succinyl/N-methyl ethylenediamine linker | 44 | 1.6 | 9.1 | |

X = 3(R)-3-amino-2-oxo-1-piperidine-acetic acid

Example 13

Synthesis of Peptide Dimers by Thiol Linkers and Bromoacetylated Peptides

Figure 4:
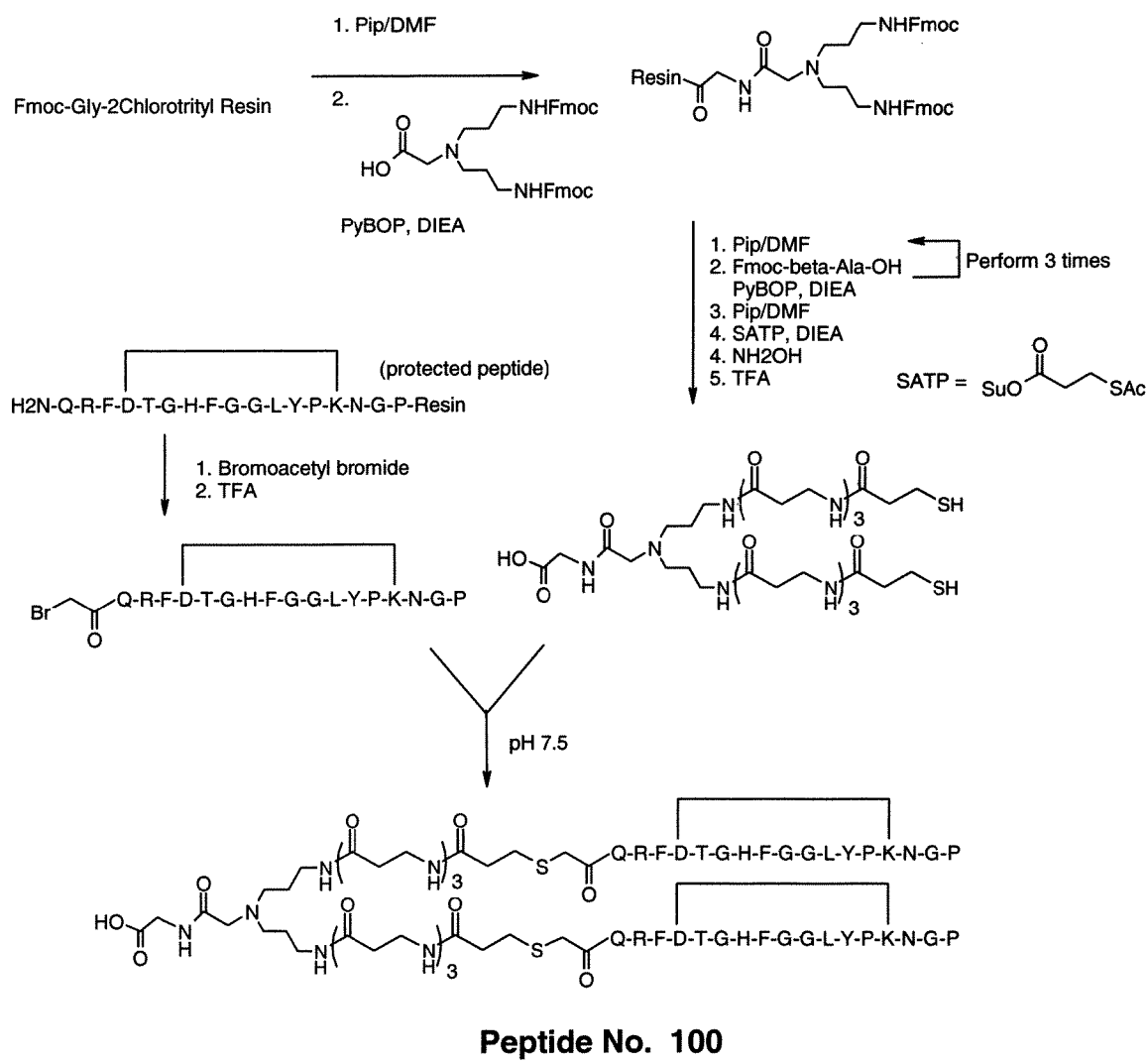
FIG. 4 shows an overview of the synthesis of peptide dimers by using a bis-thiol linker containing peptide and a bromoacetylated peptide. The synthesis of Peptide No. 100 is shown as an illustrative example. Horizontal brackets placed above the peptide sequence indicate the presence of a bridge (SEQ ID NO: 320).

Peptide dimers (Table 23) were also synthesized by reacting bromoacetylated peptides with a thiol linkers. Bromoacetylated peptides were synthesized (FIG. 4) by reacting the free α-amino group of the protected peptide resin with 4 equivalents of bromoacetyl bromide (Sigma-Aldrich, St. Louis, Mo.) and 8 equivalents of DIEA (Sigma-Aldrich, St. Louis, Mo.) in DMF. After 1 hour, the resin was washed with DMF, followed by DCM and cleaved from the resin as described above in Example 7. In the case where lactam-cyclized peptides were dimerized using a bis-thiol linker, the on-resin cyclization step was performed prior to the bromoacetylation step. In the case where disulfide-containing peptides were dimerized using a bis-thiol linker, the iodine oxidation step was performed after cleavage as described above in Example 7.

The bis-thiol linkers were synthesized (FIG. 4) by reacting NH$_2$-Gly-2-Chlorotrityl resin (Novabiochem, San Diego, Calif.) with 2 equivalents of N,N-bis(N'-Fmoc-3-aminopropyl)glycine potassium hemisulphate (Chem-Impex, Wood Dale, Ill.) in the presence of 2 equivalents of PyBOP (Novabiochem, San Diego, Calif.) and DIEA in DMF for 18 hours. The Fmoc protecting group was removed with two 10 minute treatments of 20% piperidine in DMF. For some of the linker compounds, beta-alanines were also incorporated as spacer units. Fmoc-beta-Ala-OH (Novabiochem) was coupled to the resin as above using PyBOP and DIEA. After the Fmoc protecting group was removed with 20% piperidine in DMF, either another beta-alanine spacer unit was incorporated, or the bis-thiol linker was incorporated by reacting the free N-terminal amine resin with 2 equivalents of N-succinimidyl-S-acetylthioproprionate (SATP; Pierce, Rockford, Ill.) and 4 equivalents of DIEA for 18 hours.

Subsequently, removal of the S-acetyl protecting group was accomplished by reacting 0.05 mmol of the peptide resins with a degassed solution containing 1 ml of DMF and 0.4 ml of buffer A (Buffer A: 1 M hydroxylamine hydrochloride (Sigma-Aldrich, St. Louis, Mo.), 40 mM sodium phosphate pH 7.5, 50 mM EDTA (Sigma-Aldrich, St. Louis, Mo.)) for 18 hours. The resins were washed with DMF, followed by DCM, and cleaved from the resin with a 50% solution of TFA in DCM with 2% triisopropylsilane for 15 min. The crude linkers were processed and purified as described above in Example 7.

The peptide dimers were generated using bis-thiol linkers (FIG. 4) by reacting one equivalent of the purified bis-thiol linker with a two equivalents of bromoacetylated N-terminal peptide in DMF with 10% water and 50% 100 mM sodium phosphate, pH 7.5. After 18 hours, the crude reaction mixture was purified by reversed phase HPLC column as described above in Example 7.

Figure 5:
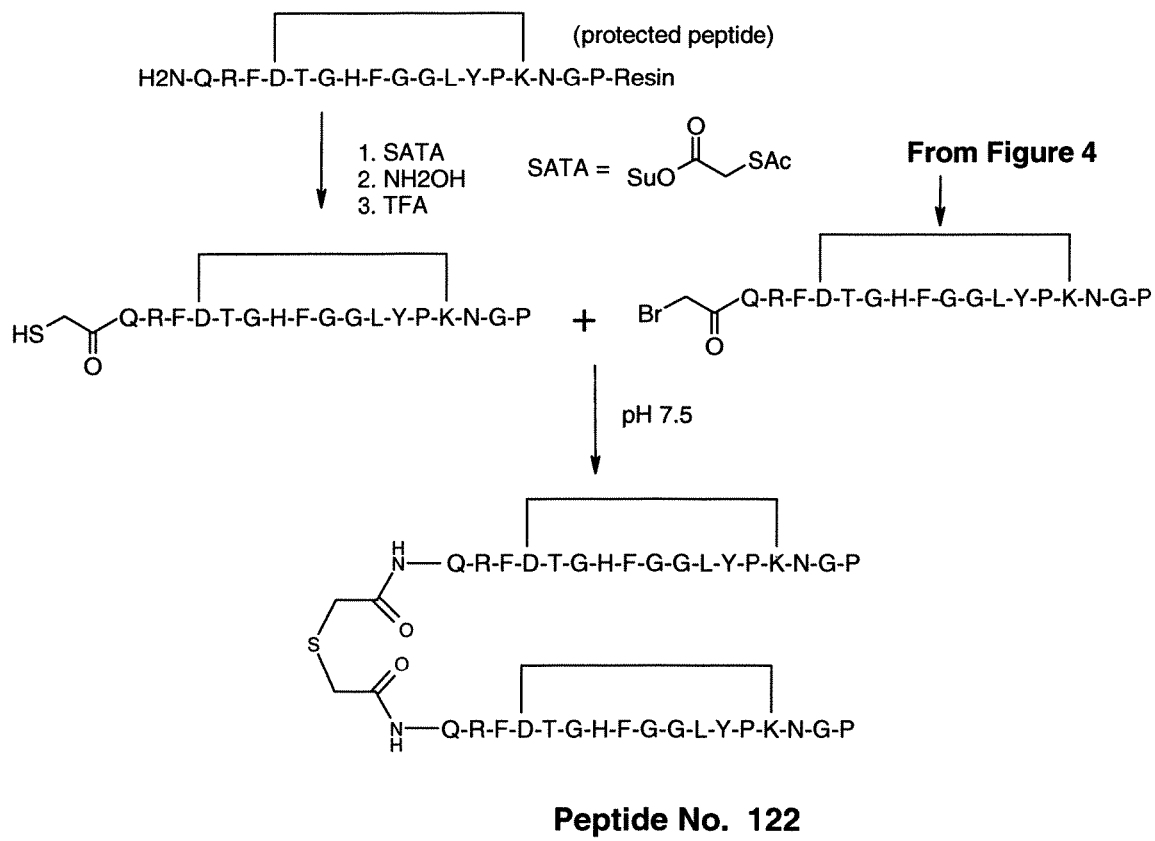
FIG. 5 shows the synthesis of peptide dimers using a thiol linker-containing peptide and a bromoacetylated peptide. The synthesis of Peptide No. 122 is shown as an illustrative example. Horizontal brackets placed above the peptide sequence indicate the presence of a bridge (SEQ ID NO: 320).

Peptide No. 122 was synthesized (FIG. 5) by reacting a bromoacetylated peptide with a peptide derivatized with SATP. Briefly, the crude peptide resin with a free N-terminal amine was reacted with 2 equivalents of SATP in DMF for 2 hours. The S-acetyl protecting group was removed as described above, followed by cleavage from the resin and subsequent purification as described above.

Table 23 provides a listing of dimeric peptides of the invention that were synthesized by thiol linkers. Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6. Column 6 contains the $IC_{50}$ of each peptide as determined by competitive IgG binding FACS analysis as outlined in Example 5.

TABLE 23

Dimers Synthesized Using Thiol Linkers

Sequence[1]

Peptide No. 100

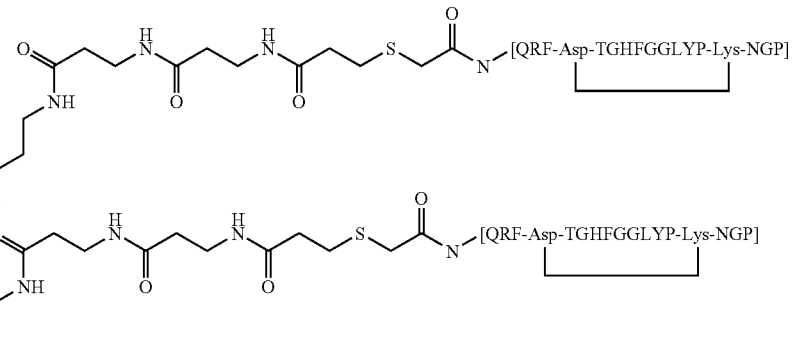

Peptide No. 119

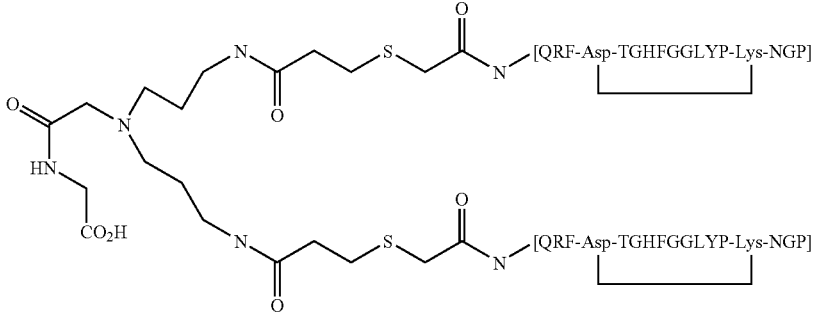

Peptide No. 120

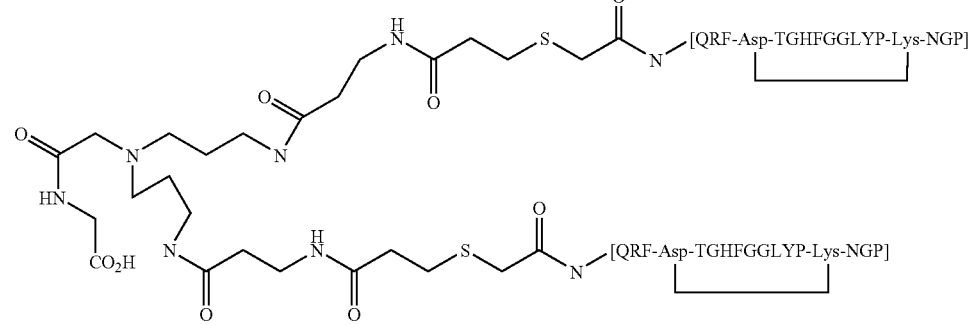

TABLE 23-continued
Dimers Synthesized Using Thiol Linkers
Peptide No. 121
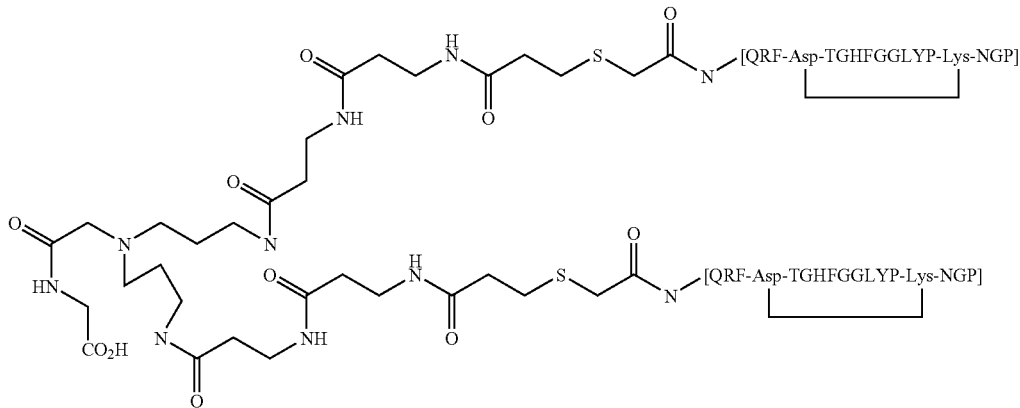
Peptide No. 122
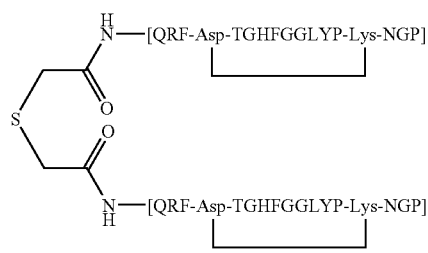
Peptide No. 160
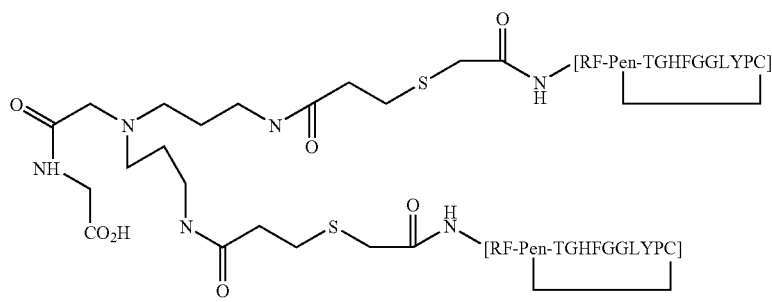
Peptide No. 161
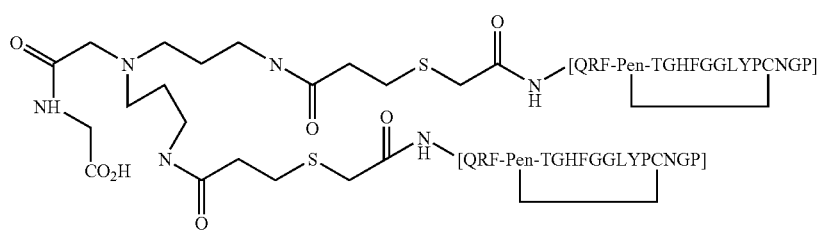
Peptide No. 199
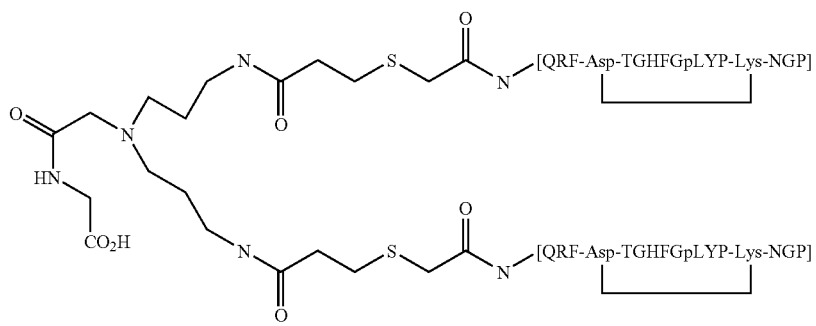

TABLE 23-continued

Dimers Synthesized Using Thiol Linkers

Peptide No. 200

[Structure with two [QRF-Asp-TGHFaG-NMeLeu-YP-Lys-NGP] peptide chains connected via thiol linkers to a branched scaffold containing CO$_2$H group]

|  | $IC_{50}$ nM | $K_D$ pH 6 nM | $K_D$ pH 7.4 nM | $IC_{50}$ nM FACS |
|---|---|---|---|---|
| Peptide No. 100 | 760 | 6 |  | 130 |
| Peptide No. 119 | 900 | 7 |  | 150 |
| Peptide No. 120 | 2400 | 7 |  | 150 |
| Peptide No. 121 | 1300 | 8 |  | 160 |
| Peptide No. 122 | 970 | 6 |  | 120 |
| Peptide No. 160 | 100 |  |  |  |
| Peptide No. 161 | 90 |  |  |  |
| Peptide No. 199 | 1200 |  | 7.9 | 190 |
| Peptide No. 200 | 1900 |  | 7.2 | 170 |

[1]Pen = penicillamine; Sar = sarcosine; p = D-proline; NMeLeu = N-methylleucine

Example 14

Synthesis of Peptide Trimers Via Reductive Alkylation: Peptide No. 247

Peptide trimers (Table 22) were generated by reductive alkylation of a peptide aldehyde and a peptide amino N-terminal amine.

Peptide N-terminal amines were synthesized as described above in Example 7 for the synthesis of monomeric peptide disulfides with the exception that the N-terminus was capped with a bifunctional amine linker such as bis-aminipropyl glycine (BAPG; used as Bis-Fmoc-BAPG purchased from Sigma-Aldrich, St. Louis, Mo.), followed by coupling sarcosine. Peptide N-terminal aldehydes (FIG. 2) were synthesized as described in Example 12. The peptide trimers were synthesized (as in FIG. 3) by reacting two equivalents of peptide aldehyde with one equivalent of amine-containing peptide at a concentration of 40 mg/ml in DMF containing 2% acetic acid. After 60 min., 4 equivalents of sodium cyanoborohydride (Sigma-Aldrich, St. Louis, Mo.) were added and the reaction was allowed to shake for 1 hour. The reaction mixture was diluted 10-fold with water and purified by HPLC and analyzed by mass spectroscopy (Mariner ES-MS) following liquid chromatography (Applied Biosystems, Foster City, Calif.) as described in Example 7.

Example 15

Synthesis Of Peptide Dimers Using Diacid and Amine Linkers

Amide linked peptide dimers (Table 24) were generated either by reacting the N-termini of two on-resin peptide monomers with a bi-functional acid linker or by performing the synthesis of the peptide on resin containing a bi-functional amine linker, thereby tethering the C-termini of two on-resin peptide monomers.

N-terminally linked peptide dimers were synthesized as described above in Example 7 for the synthesis of monomeric peptide disulfides with the following exceptions: Before the peptides are cleaved from the resin, the N-termini of two peptide monomers are joined with a bi-functional acid linker. For example, Peptide No. 283 is synthesized by reacting the peptide resin containing the peptide sequence analogous to Peptide No. 235 with an unprotected N-terminus with 0.5 equivalents of succinic acid (Sigma-Aldrich, St. Louis, Mo.) in the presence of 1 equivalent of PyBOP and 2 equivalents of DIEA. This results in adjacent peptides on the resin being covalently attached by amide bonds via their N-termini.

Figure 6:
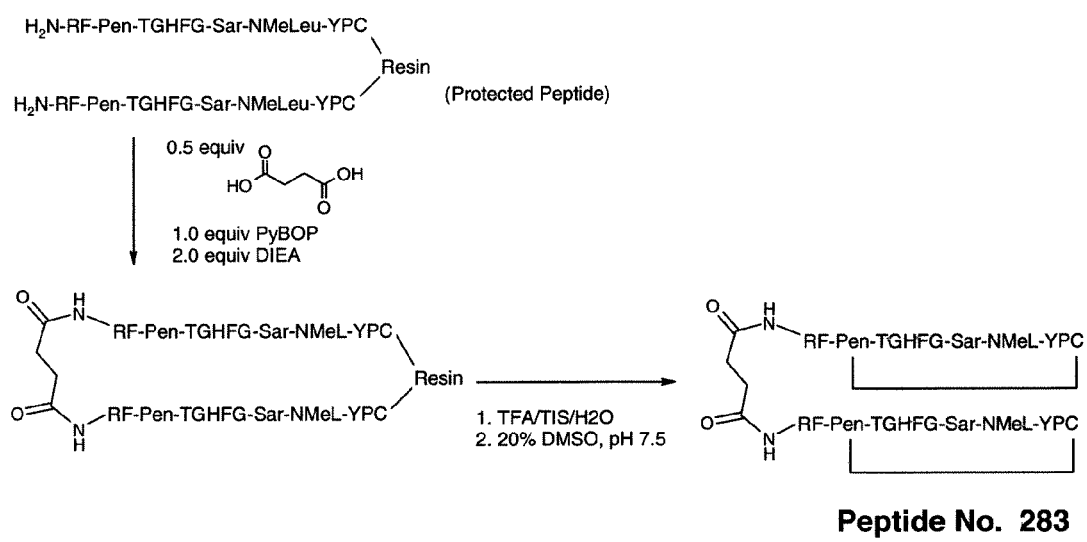
FIG. 6 shows the synthesis of peptide dimers using a diacid containing linker. The synthesis of Peptide No. 283 is shown as an illustrative example. Horizontal brackets placed below the peptide sequence indicate the presence of a bridge (SEQ ID NO: 321).

The resulting peptide dimer is cleaved from the resin and purified as described in Example 7 with the exception that the peptide disulfides are not oxidized prior to HPLC purification. The purified reduced peptide is dissolved to ca. 0.1 mg/mL in 10 mM sodium phosphate, pH 7.5 with 20% DMSO and mixed for 3 days at room temperature. This oxidation step permits the formation of the disulfide bonds within one peptide monomer of the dimer, as opposed to between two monomers of a dimer. The reaction mixture is diluted with water to peptide concentration of 0.05 mg/mL and purified over a C18 Sep-Pak column (Waters Corp., Milford, Mass.) using an increasing gradient of acetonitrile in water containing 0.1% TFA. The peptide dimer was lyophilized and subjected to analysis by mass spectroscopy (Mariner ES-MS) following liquid chromatography (Applied Biosystems, Foster City, Calif.) as described in Example 7. (See FIG. 6.) In the case of Peptide No. 283, the disulfide linkage pattern was confirmed by digesting the peptide with trypsin for 30 minutes, then analyzing the resulting peptides by LCMS. Trypsin is known to cleave after arginine and lysine residues, and cleaves Peptide No. 283 at the arginine-phenylalanine bond. The major product of LCMS of Peptide No. 283 is NH2-[Phe Phe-Pen-Thr-Gly-His-Phe-Gly-Sar-NMeLeu-Tyr-Pro-Cys]-CONH2(disulfide) (LCMS: M+H=1355.6 Da), which indicates that the disulfide bonds of Peptide No. 283 are formed between each 13 amino acid peptide monomer.

Peptide No. 201 was synthesized as Peptide No: 283 with the exceptions that the peptide sequence was analogous to Peptide No. 32, the diacid linker used was ethylene glycol-bis(succinic acid-N-hydroxysuccinimide ester) (Sigma-Aldrich, St. Louis, Mo.) and that no PyBOP was used for the coupling reaction.

Peptide No. 279 was synthesized as in Peptide No. 283 with the exception that the diacid linker used was Bis-dPEG6-N-hydroxysuccinimide ester (Quanta Biodesigns Ltd.) and that no PyBOP was used for the coupling reaction.

Peptide No. 281 was synthesized as Peptide No. 283 with the exception that the peptide-resin was treated with a large excess of succinic anhydride (Sigma-Aldrich, St. Louis, Mo.), which results in all peptides on the resin containing a succinate capped N-terminus. This resin was treated with 0.5 equivalents of N,N'-dimethylethyl-enediamine (Sigma-Aldrich, St. Louis, Mo.) in the presence of 1 equivalent of PyBOP and 2 equivalents of DIEA. The subsequent cleavage, purification and oxidation steps were performed as with Peptide No. 283.

Peptide No. 282 was synthesized as Peptide No. 283 with the exception that the diacid linker used was N-methyl-iminodiacetic acid (Sigma-Aldrich, St. Louis, Mo.).

Peptide No. 284 was synthesized as Peptide No. 283 with the exception that the diacid linker used was 3,3-dimethyl-glutaric acid (Sigma-Aldrich, St. Louis, Mo.).

Peptide No. 285 was synthesized as Peptide No. 283 with the exception that the diacid linker used was Boc-Asp(OH)—OH (Novabiochem, San Diego, Calif.).

Peptide No. 286 was synthesized as Peptide No. 283 with the exception that the diacid linker used was Boc-Glu(OH)—OH (Novabiochem, San Diego, Calif.).

Figure 7:
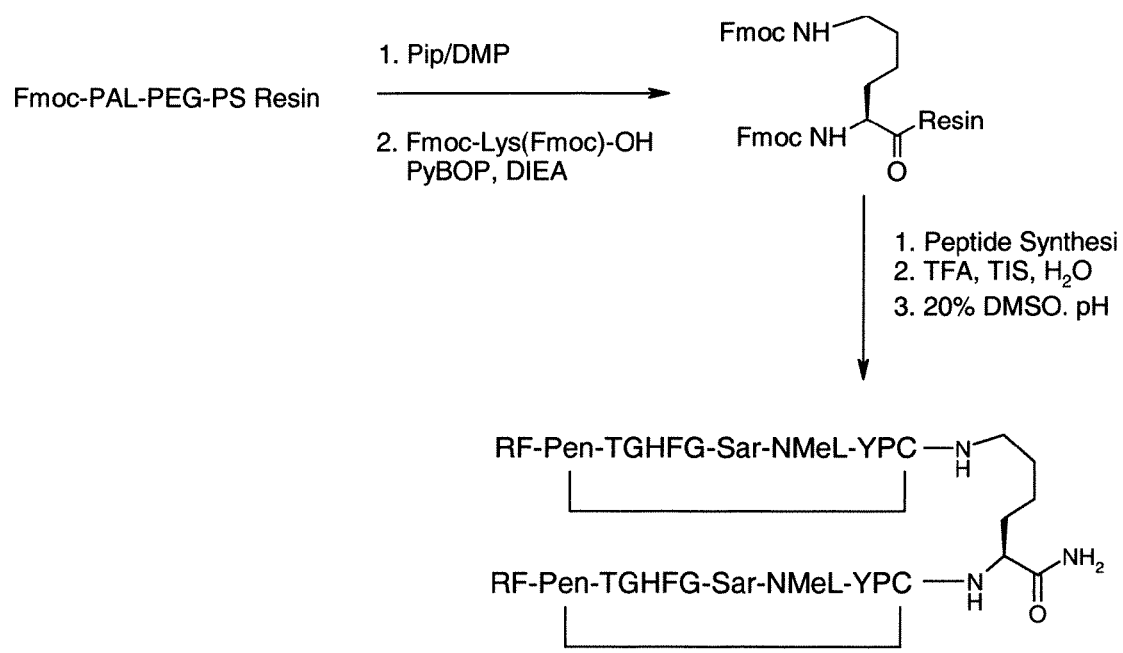
FIG. 7 shows the synthesis of peptide dimers using an amine containing linker. The synthesis of Peptide No. 280 is shown as an illustrative example. Horizontal brackets placed below the peptide sequence indicate the presence of a bridge (SEQ ID NO: 321).

C-terminally linked peptide dimers were synthesized as described above in Example 7 for the synthesis of monomeric peptide disulfides with the exception that a bifunctional amine linker is coupled to the resin prior to the peptide synthesis. This results in peptide dimers with their C-termini covalently attached by amide bonds. For example, Peptide No. 280 was synthesized by first coupling Fmoc-Lys(Fmoc)-OH (Novabiochem, San Diego, Calif.) to the resin, followed by the coupling of amino acids to give a sequence analogous to Peptide No. 235. This results in the covalent attachment of two peptide chains as they are being synthesized on the resin. The resulting peptide dimer is cleaved from the resin, purified and oxidized as described above for the N-terminally linked dimers. (see FIG. 7)

Peptide No. 287 was synthesized as Peptide No. 280 with the exception that a glycine residue (Gly) is inserted between the Peptide No. 235 sequence and the branching Lysine linker.

Peptide No. 288 was synthesized as Peptide No. 280 with the exceptions that two glycine residues (Gly-Gly) are inserted between the Peptide No. 235 sequence and the branching lysine linker.

Table 24 provides a listing of dimeric peptides of the invention that were synthesized using amide bonds. Column 1 contains the peptide identifier. Column 2 contains the amino acid sequence of the peptides. Column 3 contains the $IC_{50}$ of each peptide as determined by the IgG competition ELISA outlined in Example 4.

TABLE 24

Dimers Synthesized Using Amide Linkers

| | Sequence[1] (SEQ ID NOS 305-315) | $IC_{50}$ nM |
|---|---|---|
| Peptide No. 201 | 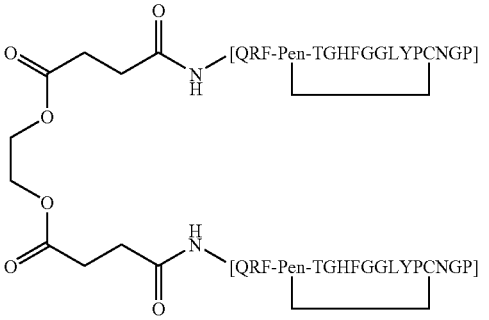 | 26 |
| Peptide No. 279 | 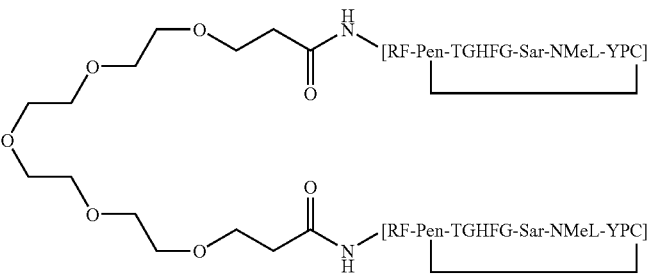 | 7 |

TABLE 24-continued
Dimers Synthesized Using Amide Linkers
| | Sequence[1] (SEQ ID NOS 305-315) | IC$_{50}$ nM |
|---|---|---|
| Peptide No. 280 | 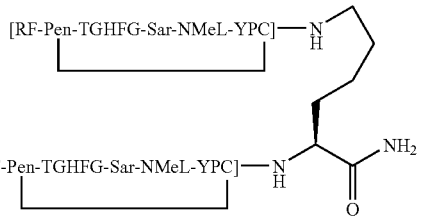 | 25 |
| Peptide No. 281 | 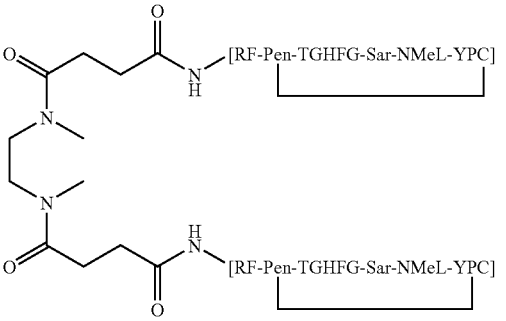 | 5.2 |
| Peptide No. 282 | 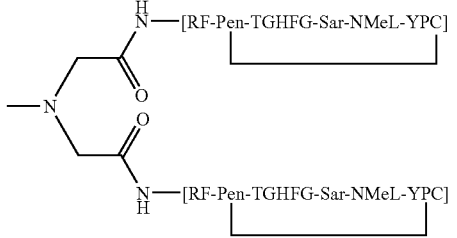 | 4.7 |
| Peptide No. 283 | 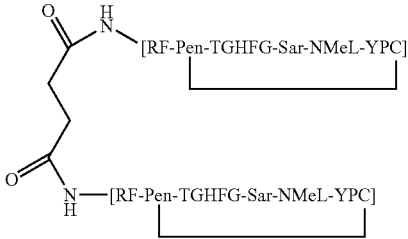 | 3.3 |
| Peptide No. 284 | 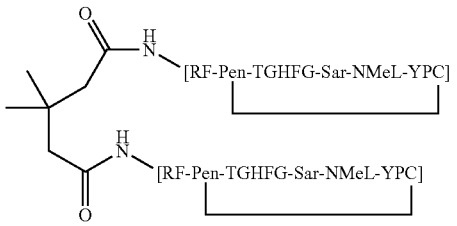 | 8.5 |
| Peptide No. 285 | 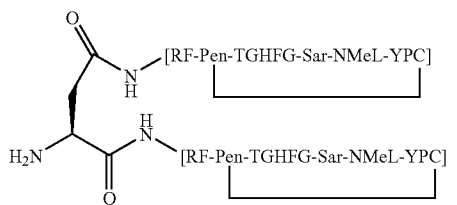 | 4.6 |

TABLE 24-continued

Dimers Synthesized Using Amide Linkers

| Peptide | Sequence[1] (SEQ ID NOS 305-315) | IC$_{50}$ nM |
|---|---|---|
| Peptide No. 286 | H$_2$N–CH(C(O)NH–[RF-Pen-TGHFG-Sar-NMeL-YPC])–(CH$_2$)$_2$–C(O)NH–[RF-Pen-TGHFG-Sar-NMeL-YPC] | 5.6 |
| Peptide No. 287 | [RF-Pen-TGHFG-Sar-NMeL-YPCG]–NH–CH(C(O)NH$_2$)–(CH$_2$)$_4$–NH–[RF-Pen-TGHFG-Sar-NMeL-YPCG] | 20 |
| Peptide No. 288 | [RF-Pen-TGHFG-Sar-NMeL-YPCGG]–NH–CH(C(O)NH$_2$)–(CH$_2$)$_4$–NH–[RF-Pen-TGHFG-Sar-NMeL-YPCGG] | 16 |

[1]Pen = penicillamine; Sar = sarcosine; NMeLeu = N-methylleucine

Example 16
Synthesis of Peptide-Fc Fusions Via Reductive Alkylation

Figure 8:
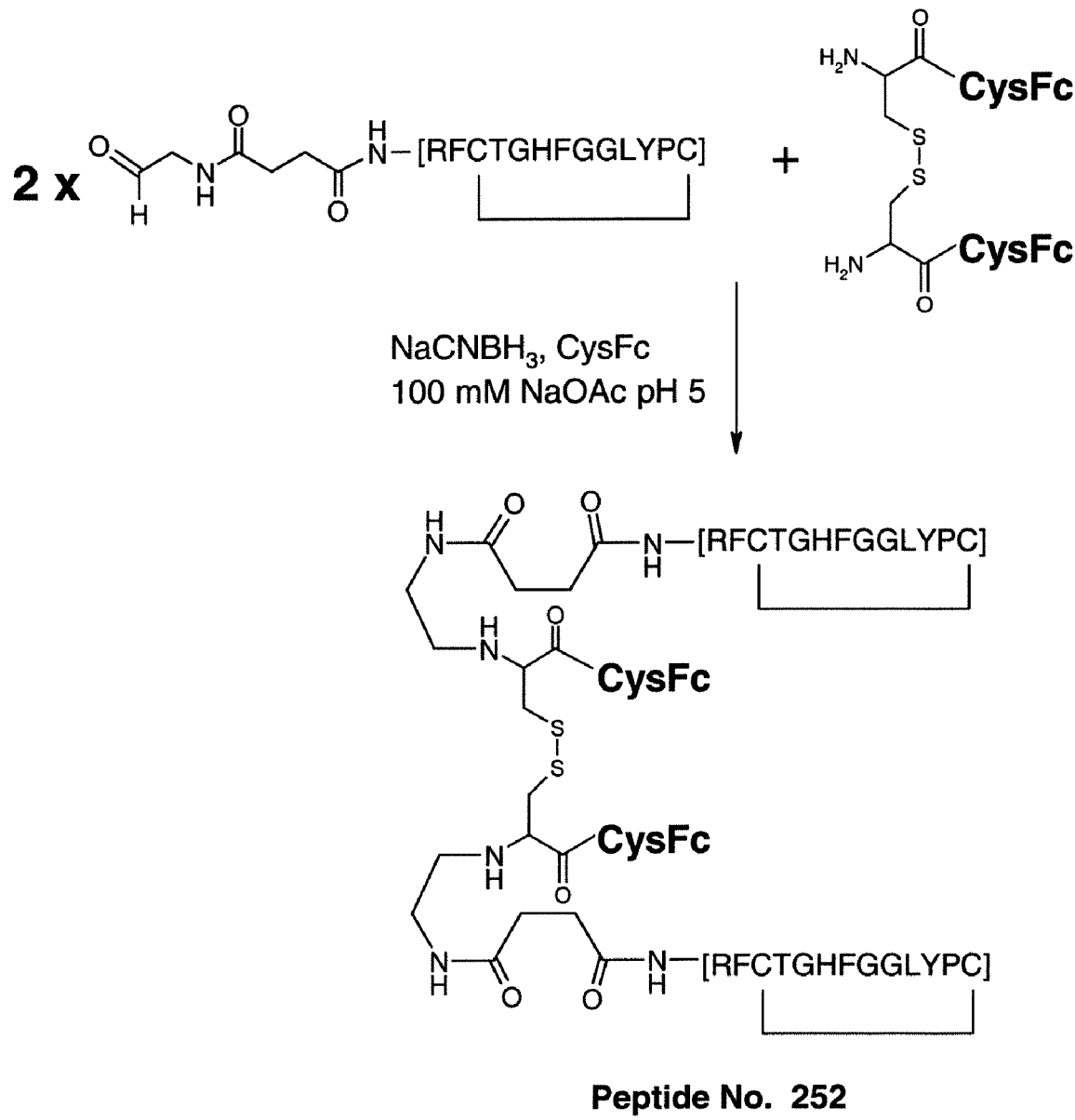
FIG. 8 shows the synthesis of peptide-Fc fusions using a peptide aldehyde and the protein CysFc. The synthesis of Peptide No. 252-Fc is shown as an illustrative example. Horizontal brackets placed below the peptide sequence indicate the presence of a bridge.
Figure 15:
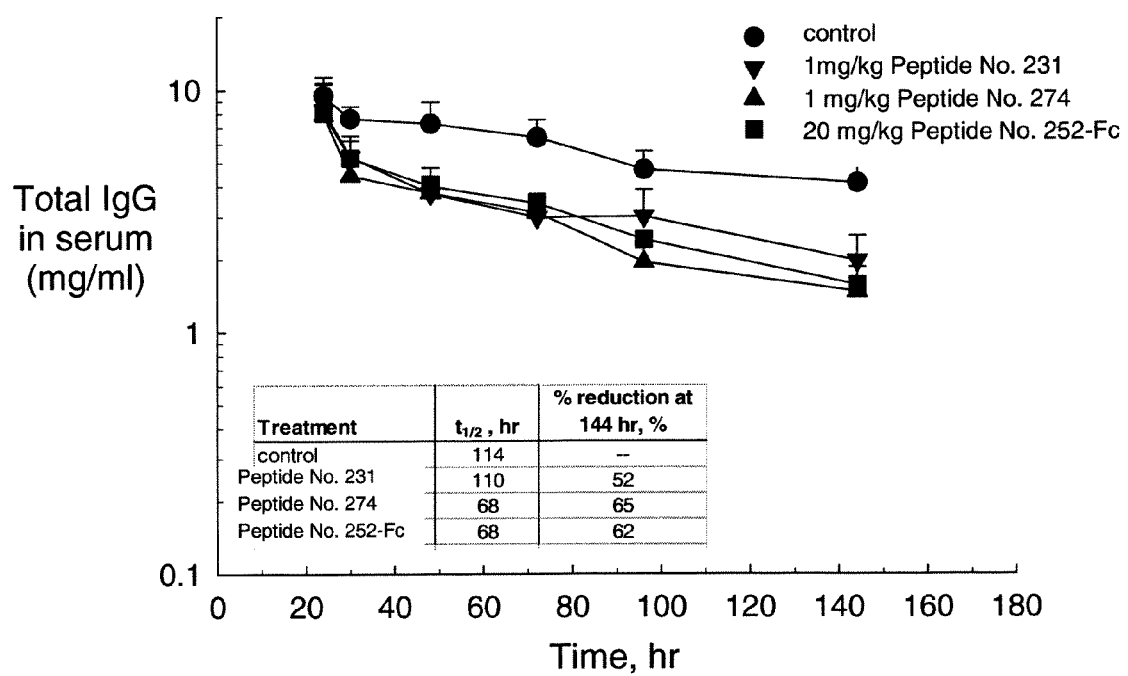
FIG. 15 shows the kinetics of human IgG catabolism in TG32B mice following the intravenous injection of Peptide No. 231, Peptide No. 274, and Peptide No. 252-Fc.

Peptide N-terminal aldehydes Peptide No. 252, Peptide No. 229 and Peptide No. 232 (Table 25) were synthesized as described in Example 12. All three peptide-Fc fusions were generated using the same protocol (FIG. 8): CysFc (Fc domain possessing a N-terminal cysteine) and 4.5 equivalents of peptide aldehyde were incubated on ice in 80 mM sodium acetate pH 5.5 for 1 hour. Sodium cyanoborohydride was added to a final concentration of 20 mM and the reaction was incubated for 16 hours at 4° C. The reaction mixture was analyzed by SDS-PAGE to ensure the addition of predominantly a single peptide to the Fc protein. The protein mixture was dialyzed twice with PBS and assayed for in vitro blocking activity (Table 25). In the case of Peptide No. 252-Fc, the protein was also evaluated in the TG32B mouse IgG catabolism model. (FIG. 15). The production of CysFc can be performed as described in US Patent Application Publication No. US 2005/0027109, where the disclosure of the production of CysFc is incorporated herein by reference.

Table 25 provides a listing of peptide-Fc fusion proteins of the invention that were synthesized using CysFc and aldehyde-peptides. Column 1 contains the peptide-Fc fusion identifier. Column 2 contains the amino acid sequence of the peptides. Column 3 contains the IC$_{50}$ of each peptide as determined by the IgG competition ELISA outlined in Example 4.

TABLE 25

Peptide-Fc Fusions

| | Sequence[1] | ID$_{50}$ nM |
|---|---|---|
| CysFc | | 210 |
| Peptide No. 229-Fc | [structure: Fc-linker-[RF-Pen-TGHF-NMeLeu-YPC] dimer] | 2 |
| Peptide No. 232-Fc | [structure: Fc-linker-[RF-Pen-TGHFG-Sar-NMeLeu-YPC] dimer] | 3 |
| Peptide No. 252-Fc | [structure: Fc-linker-[RFCTGHFGGLYPC] dimer] | 39 |

[1]Pen = penicillamine; Sar = sarcosine; NMeLeu = N-methylleucine

Example 17

Transgenic Mice

Transgenic mice were obtained from Dr. Roopenian of The Jackson Laboratory in Bar Harbor, Me. The endogenous murine FcRn and β$_2$m genes were inactivated by insertion of a foreign polynucleotide sequence by homologous recombination and replaced transgenically with the human FcRn and the human β$_2$m genes (muFcRn (−/−), muβ$_2$m (−/−), +huFcRn, +huβ$_2$m). These mice are referred to by the strain name TG32B.

Example 18

Figure 9:
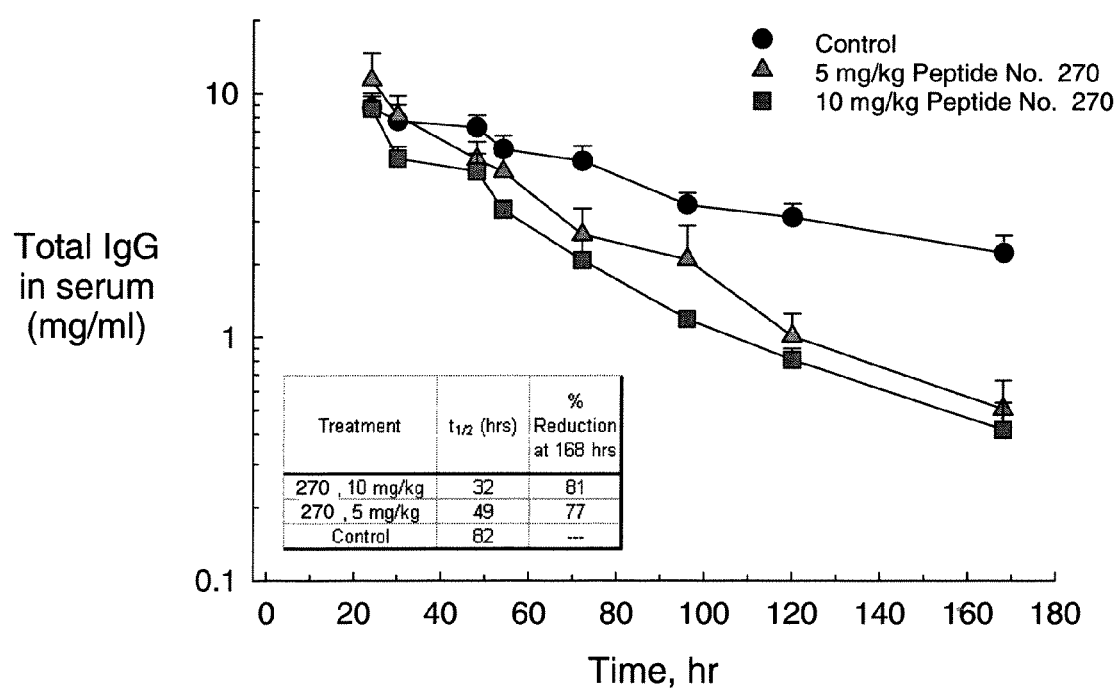
FIG. 9 shows the kinetics of human IgG catabolism in TG32B mice (mice engineered to express the human FcRn and human $\beta_2$m, but not the murine FcRn or $\beta_2$m).

Effect of Peptide No. 270 on Human IgG Catabolism in TG32B Mice Using 5 mg/kg and 10 mg/kg Adult TG32B mice were injected intravenously with 500 mg/kg of human IgG (MP Biomedicals, Irvine, Calif.) at t=0 hours (T$_0$). At 24, 48, 72, 96 and 120 hours, the mice were injected intravenously with either 5 mg/kg or 10 mg/kg Peptide No. 270. Control injections were performed at each time-point using the vehicle PBS with 15 mM sodium acetate, pH 5. Blood samples were taken prior to injections at all time-points, as well as at 168 hours. Serum was prepared and stored at −20° C. until an ELISA was performed (FIG. 9).

An IgG Fc domain-specific ELISA was used to detect the levels of human IgG in the serum at each time point. Briefly, 30 μl of a 10 μg/ml stock solution of goat anti-human IgG (Pierce, Rockford, Ill.) was diluted with 6 ml of 0.05 M sodium bicarbonate, pH 9.6 (Sigma-Aldrich, St. Louis, Mo.). A 96-well plate was coated with 50 μl/well of this solution and incubated for 1 hour at 37° C. The coating solution was removed and washed once with PBST (phosphate buffered saline with 0.05% Tween-20). Then 200 μl/well of a 2% bovine serum albumin (BSA) stock solution in PBS was added and the plate incubated for 1 hour at 37° C. The wells were washed three times with PBST and a standard curve was generated in triplicate by performing 2.5-fold dilutions starting from 50 ng/ml of hIgG1. Then 100 μl of either the standard or sample solutions was added to the wells and the plate was incubated for 1 hour at 37° C. Three more PBST washes were performed followed by the addition of 100 μl of a 1:10,000 dilution of a goat anti-human IgG[Fc]-HRP conjugate (Pierce, Rockford, Ill.) in PBS containing 2% BSA. The plate was allowed to incubate for 1 hour at 37° C. followed by washes with PBST and the addition of a 100 µl of TMB One-Component substrate (BioFX, Owings Mills, Md.) to each well. Color development was halted after 5 minutes by the addition of 100 µl of 0.25 M sulfuric acid to each well. The UV absorbance for each well was measured at 450 nm and a calibration curve was used to derive a plot of serum IgG concentration vs. time for the experiments.

Example 19

Effect of Peptide No. 231, Peptide No. 274 and Peptide No. 252-Fc on Human IgG Catabolism in TG32B mice Adult TG32B mice were injected intravenously with 500 mg/kg of human IgG (MP Biomedicals, Irvine, Calif.) at t=0 hours ($T_0$). At 24, 48 and 72 hours, the mice were injected intravenously with either 1 mg/kg of Peptide No. 231, 1 mg/kg Peptide No. 274 or 20 mg/kg of Peptide No. 252-Fc. Control injections were performed at each timepoint using 15 mM sodium acetate, pH 5 and served as the vehicle for all injections. Blood samples were taken prior to injections at all timepoints, as well as at 30, 96 and 144 hours. Serum was prepared and stored at −20° C. until an ELISA was performed.

The concentration of human IgG in the serum at each time point were determined as described above in Example 18 (FIG. 15).

Example 20

Figure 10:
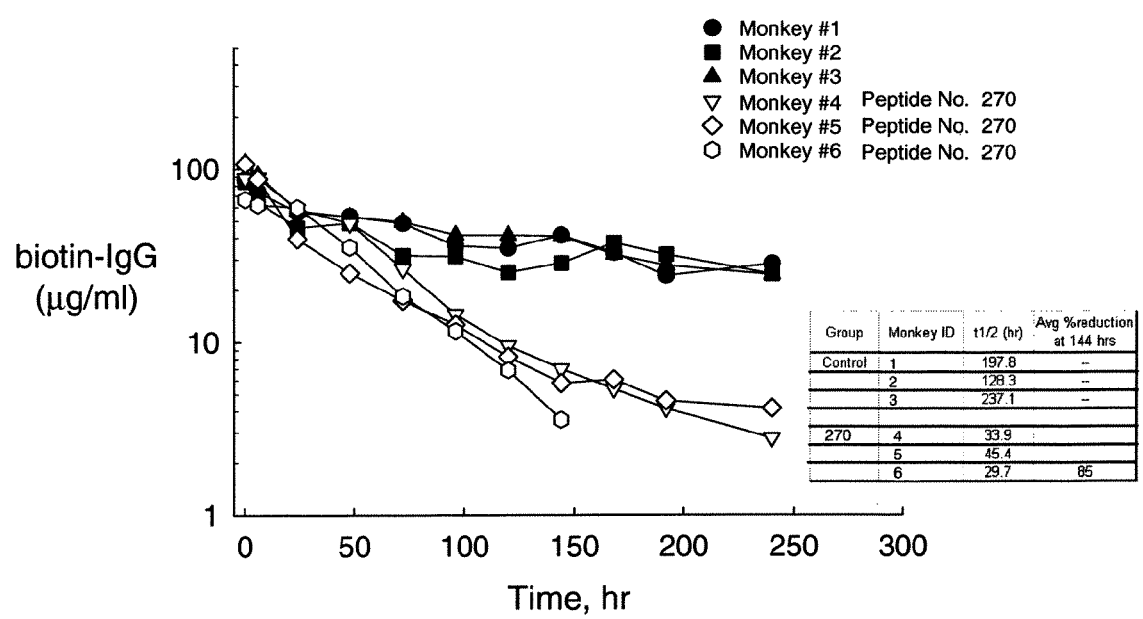
FIG. 10 shows that the catabolism kinetics of biotinylated human IgG in cynomolgous monkeys is accelerated following the intravenous injection of Peptide No. 270.
Figure 11:
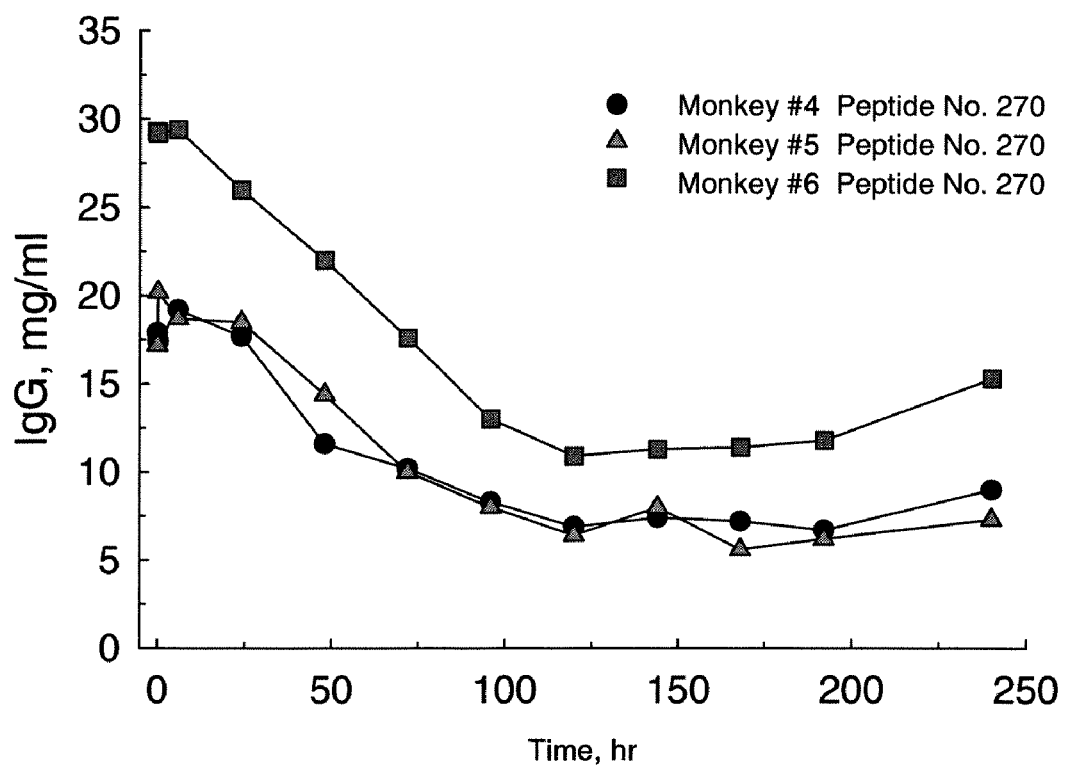
FIG. 11 shows the serum levels of endogenous IgG in cynomolgous monkeys following the intravenous injection of Peptide No. 270.
Figure 12:
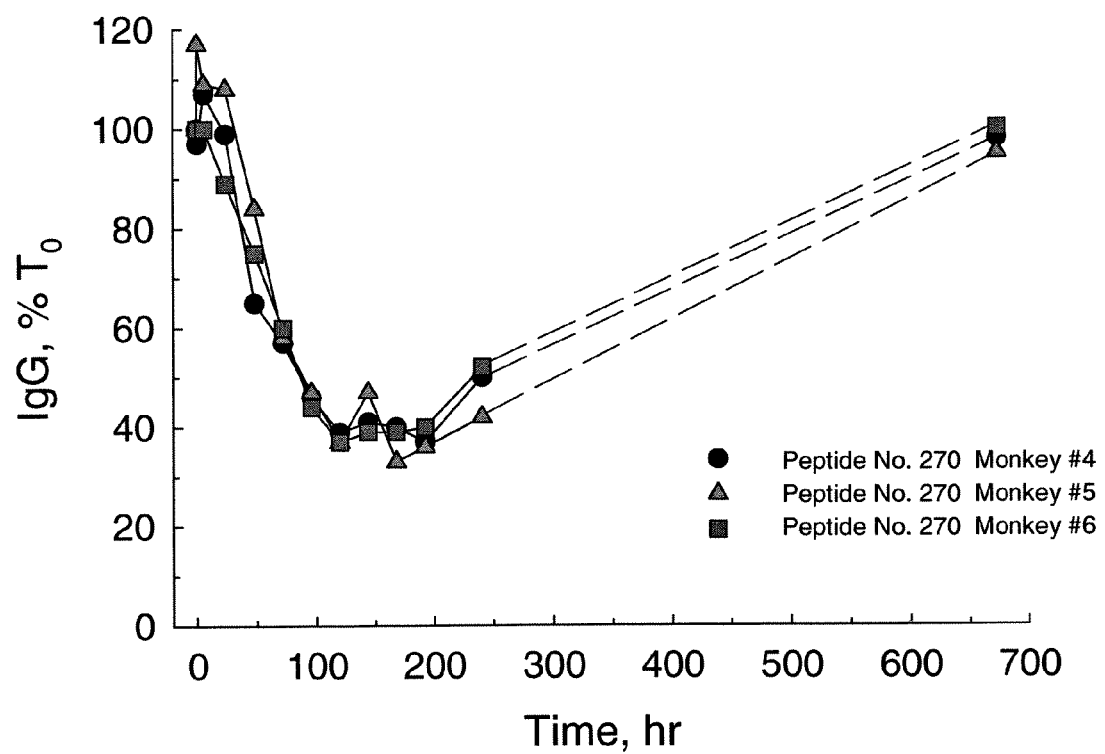
FIG. 12 is a representation of the results shown in FIG. 11, wherein the levels of endogenous cynomologous monkey IgG have been normalized to $T_0$. levels.

Effect of Peptide No. 270 on Human IgG Catabolism as Well As Endogenous IgG, IgM and Albumin in Cynomolgus Monkeys Three adult cynomolgus monkeys with an average weight of 4.8 kg were injected intravenously with an IV dose of 5 mg/kg biotinylated human IgG (MP Biomedicals, Irvine, Calif.) at 0 hours. At 24, 48, 72 and 96 hours, the animals were injected intravenously at a rate of 1 ml/min with either 10 mg/kg of Peptide No. 270 or an equal volume of vehicle (30 mM sodium acetate, pH 5). At 120 hours, animal CO6215 was treated with a fifth dose of 10 mg/kg of Peptide No. 270. Blood samples were taken prior to all injections, as well as at 120, 168, 192, and 244 hrs and at 30 days. Serum was prepared and stored at −20° C. until an ELISA was performed (FIGS. 10-12).

The biotin-hIgG tracer was detected using a Streptavidin-Fc-specific ELISA. Streptavidin-coated plates (Pierce, Rockford, Ill., cat#15121) were washed three times with PBST (phosphate buffered saline+0.05% Tween-20). Serum samples and standards were diluted with PBSB (PBS+2% BSA). A standard curve was established with a range from 1.56 ng/ml to 200 ng/ml. Diluted samples (100 µl) or standards were added per well and incubated for two hours at room temperature. Afterwards, the wells were washed three times with PBST (300 µl/well). Goat anti-human Fc-HRP (Pierce, Rockford, Ill., Cat#31416) was diluted 1:25,000 with PBSB and 100 µl/well was added and the plates were incubated for 30 minutes at room temperature. The plate washed three times with PBST (300 µl/well) and developed with 100 µl/well of BioFx Supersensitive TMB substrate (BioFX, Owing Mills, Md.) for approximately five minutes at room temperature. The development of the reaction was stopped by adding 100 µl/well of 0.25 M sulfuric acid and the absorbance of each well was measured at a wavelength of 450 nm.

Endogenous cynomolgus IgG was detected using the following ELISA protocol. First, rabbit anti-monkey IgG was diluted to 2 µg/ml in coating buffer (coating buffer=1 carbonate-bicarbonate capsule, Sigma-Aldrich, St. Louis, Mo. cat#C-3041, dissolved in 100 mL water). Next, a 96-well plate (Costar/Corning) was coated with 100 µl/well of a 2 µg/ml rabbit anti-monkey IgG (Sigma-Aldrich, St. Louis, Mo.) and incubated for one hour at 37° C. The plate washed four times with PBST (PBS with 0.05% Tween-20) and blocked for one hour at 37° C. with 200 µl/well of PBSB (1% BSA in PBS; diluted from 10% BSA in PBS stock; KPL). The plate washed again four times with PBST. Serum samples and standards were diluted with PBSB. A standard curve was established with a range of 2000 ng/ml to 1.9 ng/ml of monkey IgG (Antibodies Incorporated, Davis, Calif.). Then 100 µl/well of each sample was incubated for one hour at 37° C. The plate washed three times with PBST. 100 µl/well of a 1:30,000 dilution of rabbit anti-Monkey IgG-HRP (Sigma-Aldrich, St. Louis, Mo.) in PBSB was added and incubated for one hour at 37° C. The plate washed three times with PBST and developed with 100 µl/well of SureBlue TMB substrate (KPL, Gaithersburg, Md.) for approximately five minutes at room temperature. The development reaction was stopped with 100 µl/well of TMP stop solution (KPL, Gaithersburg, Md.) and the absorbance of each well was measured at a wavelength of 450 nm.

Figure 13:
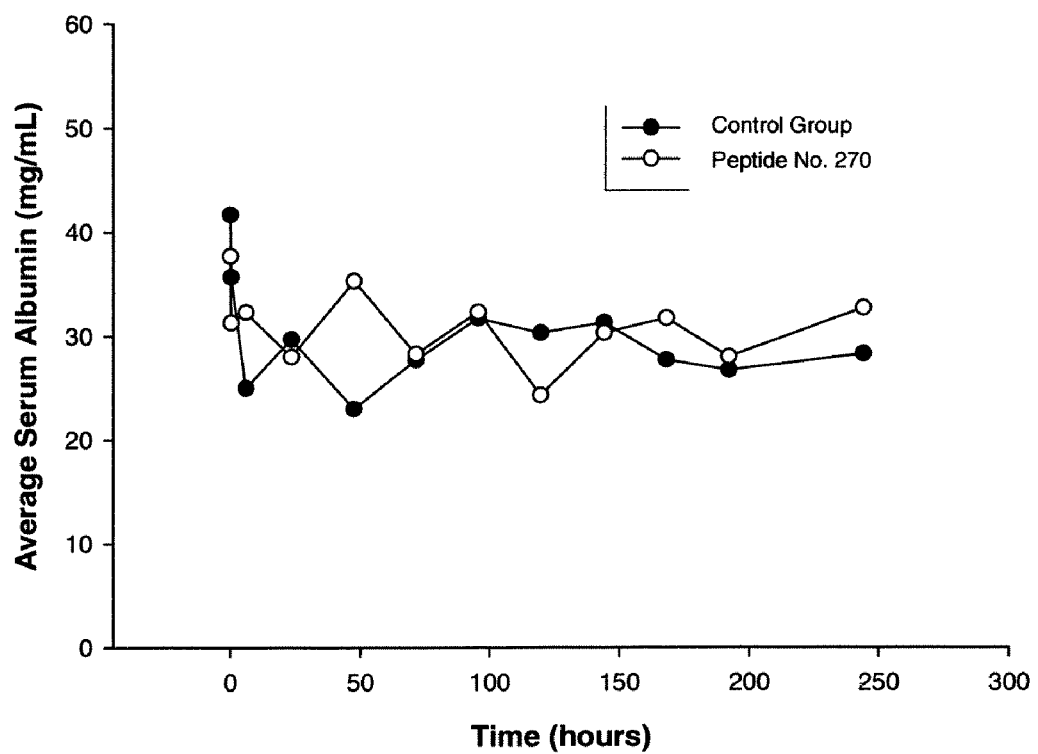
FIG. 13 shows the levels of endogenous serum albumin in cynomolgous monkeys following the intravenous injection of Peptide No. 270.

Endogenous cynomolgus serum albumin was detected using the following ELISA protocol. First, rabbit anti-monkey serum-albumin was diluted to 5 µg/ml in coating buffer (coating buffer=1 carbonate-bicarbonate capsule, Sigma-Aldrich, St. Louis, Mo. cat#C-3041, dissolved in 100 mL water). Next, a 96-well plate (Costar/Corning) was coated with 100 µl/well of the 5 µg/ml rabbit anti-monkey serum-albumin (Nordic Immunology, The Netherlands, cat#RAMon/Alb) and incubated for one hour at 37° C. The plate washed four times with PBST (PBS with 0.05% Tween-20) and blocked for one hour at 37° C. with 300 µl/well of a 5% fish gelatin (Sigma-Aldrich, St. Louis, Mo. cat#G-7765) stock solution in PBS. The plate washed again four times with PBST. Serum samples and standards were diluted with PBSB. A standard curve was established with a range of 200 ng/ml to 0.39 ng/ml of monkey serum albumin (Nordic Immunology, The Netherlands, cat#MonAlb Batch#6082). Then 100 µl/well of each sample was incubated for one hour at 37° C. The plate washed six times with PBST. 100 µl/well of a 1:30,000 dilution of goat anti-human albumin-HRP conjugate (Academy Bio-Medical, Inc., Houston, Tex., cat#AL10H-G1a) in PBSB was added and incubated for one hour at 37° C. The plate washed six times with PBST and developed with 100 µl/well of SureBlue TMB substrate (KPL, Gaithersburg, Md.) for approximately five minutes at room temperature. The development reaction was stopped with 100 µl/well of TMP stop solution (KPL, Gaithersburg, Md.) and the absorbance of each well was measured at a wavelength of 450 nm (FIG. 13).

Figure 14:
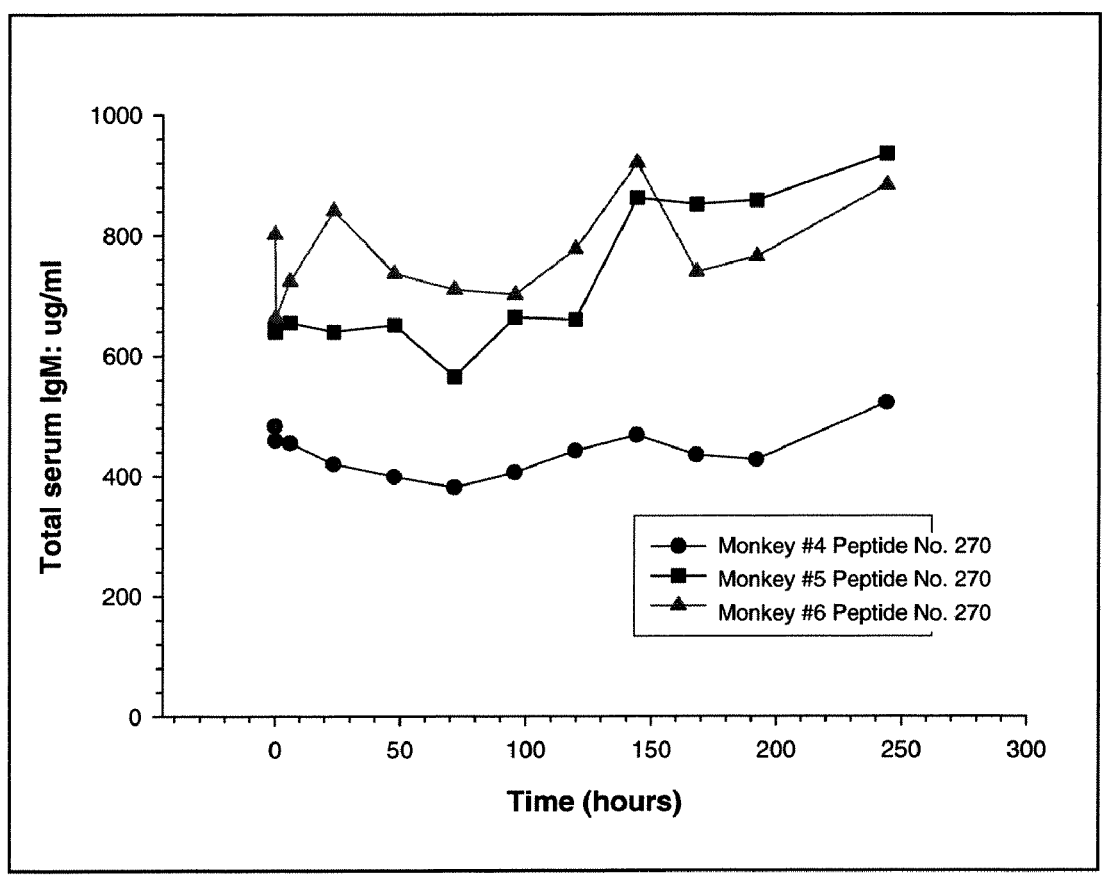
FIG. 14 shows the levels of endogenous IgM in cynomolgous monkeys following the intravenous injection of Peptide ID No. 270.

Endogenous cynomolgus IgM was detected using the following ELISA protocol. First, goat anti-monkey-IgM antibody was diluted to 5 µg/ml in coating buffer (coating buffer=1 carbonate-bicarbonate capsule, Sigma-Aldrich, St. Louis, Mo. cat#C-3041, dissolved in 100 mL water). Next, a 96-well plate (Costar/Corning) was coated with 100 µl/well of the 5 µg/ml goat anti-monkey IgM (KPL, Gaithersburg, Md., cat#071-11-031) and incubated for one hour at 37° C. The plate washed four times with PBST (PBS with 0.05% Tween-20) and blocked for one hour at 37° C. with 200 µl/well of PBSB (1% BSA in PBS; diluted from 10% BSA in PBS stock; KPL). The plate washed again four times with PBST. Serum samples and standards were diluted with PBSB. A standard curve was established with a range of 2000 ng/ml to 15.6 ng/ml of monkey IgM (Alpha Diagnostic International, San Antonio, Tex., cat#2001301). Then 100 µl/well of each sample was incubated for one hour at 37° C. The plate washed four times with PBST. 100 µl/well of a 1:10,000 dilution of goat anti-monkey IgM-HRP conjugate (RDI, Concord, Mass., cat#617103007) in PBSB was added and incubated for one hour at 37° C. The plate washed four times with PBST and developed with 100 µl/well of SureBlue TMB substrate (KPL, Gaithersburg, Md.) for approximately five minutes at room temperature. The development reaction was stopped with 100 µl/well of TMP stop solution (KPL, Gaithersburg, Md.) and the absorbance of each well was measured at a wavelength of 450 nm (FIG. 14).

Example 21

Figure 16:
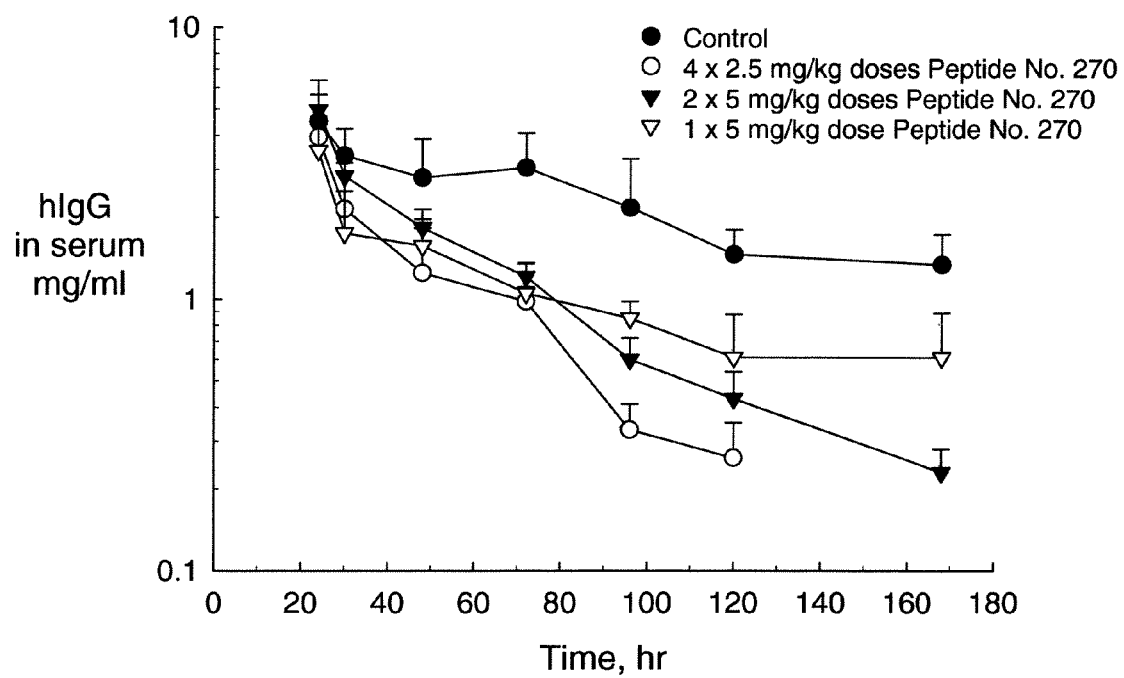
FIG. 16 shows the kinetics of human IgG catabolism in TG32B mice following the intravenous injection of Peptide No. 270.

Effect of Peptide No. 270 on Human IgG Catabolism in TG32B Mice Using Varying Dosing Schedules Adult TG32B mice were injected intravenously with 500 mg/kg of human IgG (MP Biomedicals, Irvine, Calif.) at t=0 hours ($T_0$). One group of four mice were injected intravenously with 5 mg/kg of Peptide No. 270 at t=24 hours; a second group of four mice were injected intravenously with 5 mg/kg of Peptide No. 270 at t=24 and 72 hours; a third group of four mice was injected intravenously with 2.5 mg/kg of Peptide No. 270 at t=24, 48, 72, 96 hours. Control injections were performed at each timepoint using the vehicle PBS with 15 mM sodium acetate, pH 5 using an additional group of mice. Blood samples were taken prior to injections at all timepoints, as well as at 168 hours. Serum was prepared and stored at −20° C. until an ELISA was performed as in Example 18 (FIG. 16).

Example 22

Additional TG32B Mouse Experiments

Additional experiments were performed with Peptide No. 270 in TG32B mice. Using the same experimental design as described in Example 18, Peptide No. 270 was found effective at accelerating the rate of IgG catabolism using subcutaneous (SC) and intraperitoneal (IP) routes of administration. Five daily doses of 5 mg/kg of Peptide No. 270 starting at 24 hours was found to reduce the half-life of IgG to 56 hours following both subcutaneous (SC) and intraperitoneal (IP) injections of Peptide No. 270. These half-lives are significantly shorter than typical control groups which exhibit IgG half-lives of 80 to 100 hours. In addition, the concentration of hIgG was reduced by 56% (SC) and 66% (IP) after 168 hours using Peptide No. 270 as compared to the control group.

Peptide No. 230 was also tested in the TG32B mice using the experimental protocol described in Example 18. Twenty-four hours after the intravenous injection of human IgG, daily intravenous (IV) injections of 5 mg/kg of Peptide No. 230 were administered for a total of five days. The half-life of hIgG was reduced to 39 hr as compared to the control group half-life of 92 hr. In addition, the concentration of hIgG was reduced by 76% after 168 hours as compared to the control group.

Peptide No. 230 was also tested in two experiments designed to evaluate the effect of a single peptide dose as compared to three daily peptide doses. Using the experimental protocol described in Example 18, twenty-four hours after the IV injection of human IgG, one animal group was treated with a single IV dose of 5 mg/kg Peptide No. 230, while a second animal group received three consecutive daily IV doses of 5 mg/kg Peptide No. 230. After 120 hours, the single dose of Peptide No. 230 reduced the concentration of hIgG in the mice by 41%. In the group of mice that received three daily doses of Peptide No. 230 the concentration of hIgG decreased 61% after 120 hours.

Example 23

Effect of Peptide No. 283 on Human IgG Catabolism in TG32B Mice

Adult TG32B mice were injected intravenously with 500 mg/kg of human IgG (MP Biomedicals, Irvine, Calif.) at t=0 hours ($T_0$). At 24, 48, 72 and 96 hours, the mice were injected intravenously with either 0.5, 1, 2.5, 5, or 10 mg/kg of Peptide No. 283. Control injections were performed at each timepoint using 15 mM sodium acetate, pH 5 and served as the vehicle for all injections. Blood samples were taken prior to injections at all timepoints, 120 hours, and 168 hours, as well as at 30 days. Serum was prepared and stored at −20° C. until an ELISA was performed.

Figure 17:
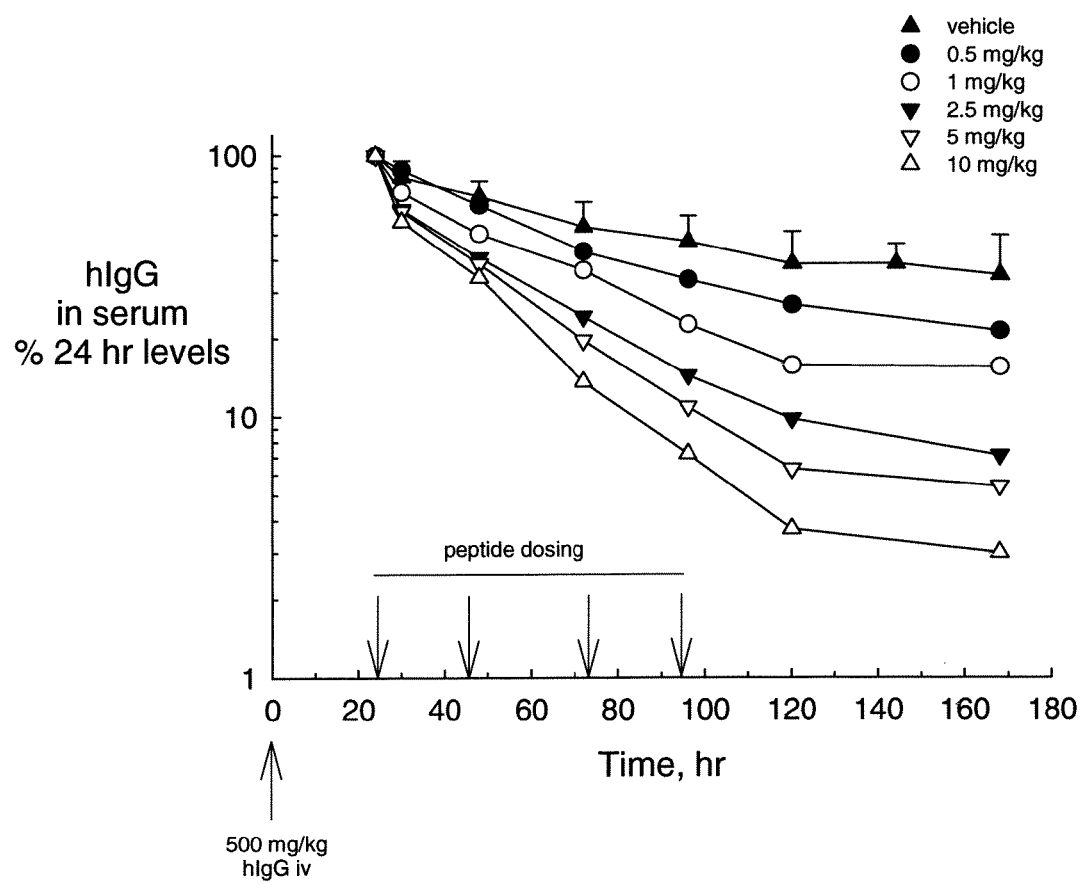
FIG. 17 shows the kinetics of human IgG catabolism in TG32B mice following intravenous injection of Peptide No. 283.

The concentration of human IgG in the serum at each time point were determined as described above in Example 18 (FIG. 17).

Example 24

Synthesis of Pegylated Peptide No. 289

Figure 18:
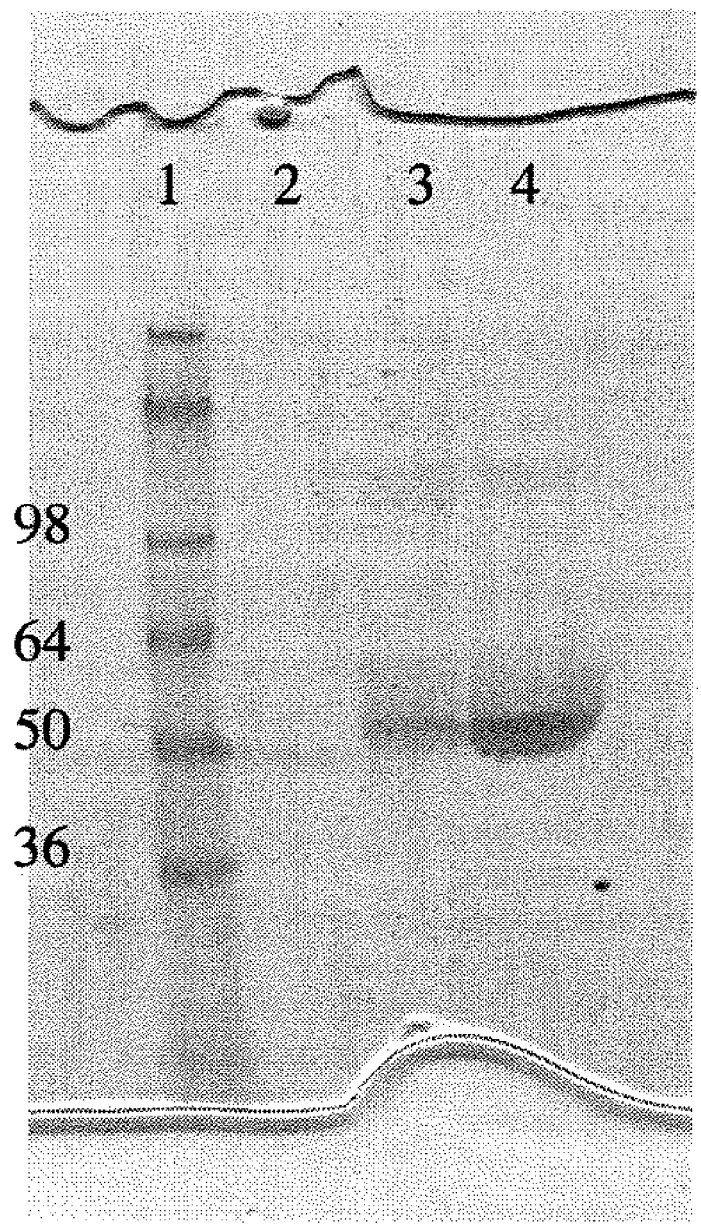
FIG. 18 shows the molecular weight of Peptide No. 289 by SDS-PAGE analysis of purified Peptide No. 289 on a 4-20% Tris-Gly gel. Lane 1 contains molecular weight markers. Lane 2 contains unconjugated $PEG_{30kDa}$ starting material. Lane 3 contains crude reaction mixture. Lane 4 contains purified Peptide No. 289.

Peptide No. 285 was dissolved in 10 mM phosphate pH 7.4 buffer and treated with one equivalent of $PEG_{30\ kDa}$-succinimidyl ester (NOF Corp, Japan, Sunbright MEGC-30TS) for 18 h. The crude reaction mixture was purified on a C4 column (Jupiter, Phenomenex) as described in example 7, lyophilized, and purified again with cation exchange chromatography (Fractoprep $SO_3^-$, Cat No. 1.17972, EMD Chemicals Inc, Gibbstown, N.J.) whereby the peptide bound to the resin in 10 mM sodium acetate pH 5, the resin washed with 10 mM sodium acetate pH 5, and the peptide was eluted with 100 mM sodium chloride in 10 mM sodium acetate pH 5. The peptide solution was dialyzed against 1% acetic acid, and lyophilized. The purified peptide was analyzed by SDS-PAGE demonstrating a peptide staining band at ~50 kDa, and by HPLC demonstrating that there is no residual free peptide. (FIG. 18).

TABLE 26

Pegylated Analog of Peptide No. 285

| | Sequence | IC$_{50}$ nM |
|---|---|---|
| Peptide No. 289 | see below | 18 |

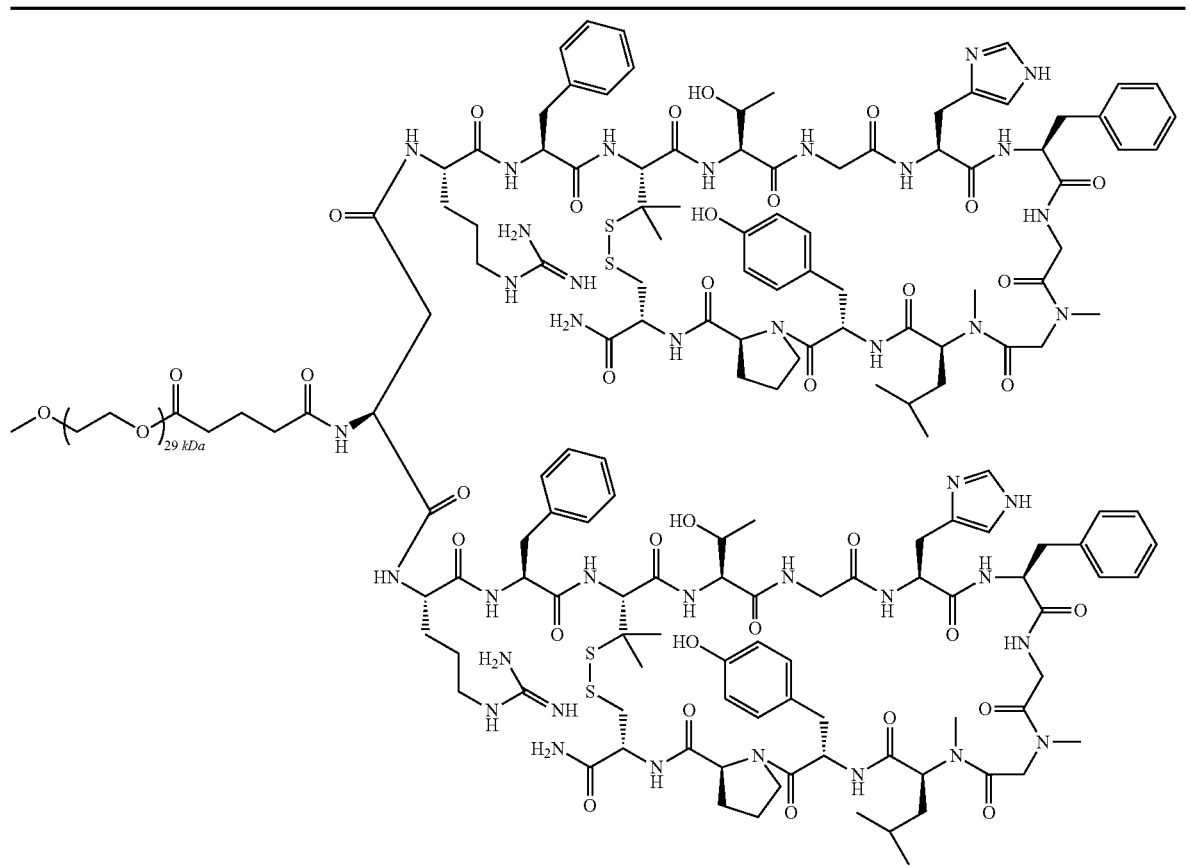

Example 25

Effect of Peptide No. 289 on Human IgG Catabolism in TG32B Mice

Figure 19:
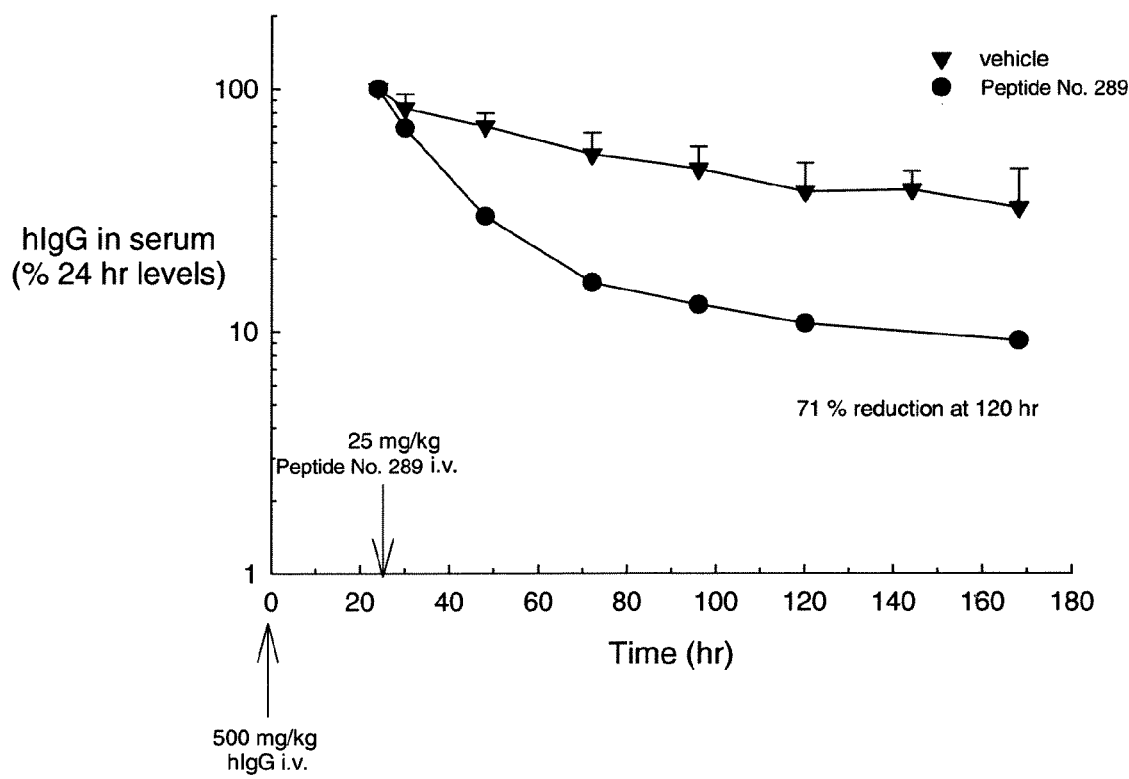
FIG. 19 shows the kinetics of human IgG catabolism in TG32B mice following intravenous injection of Peptide No. 289.
Figure 20:
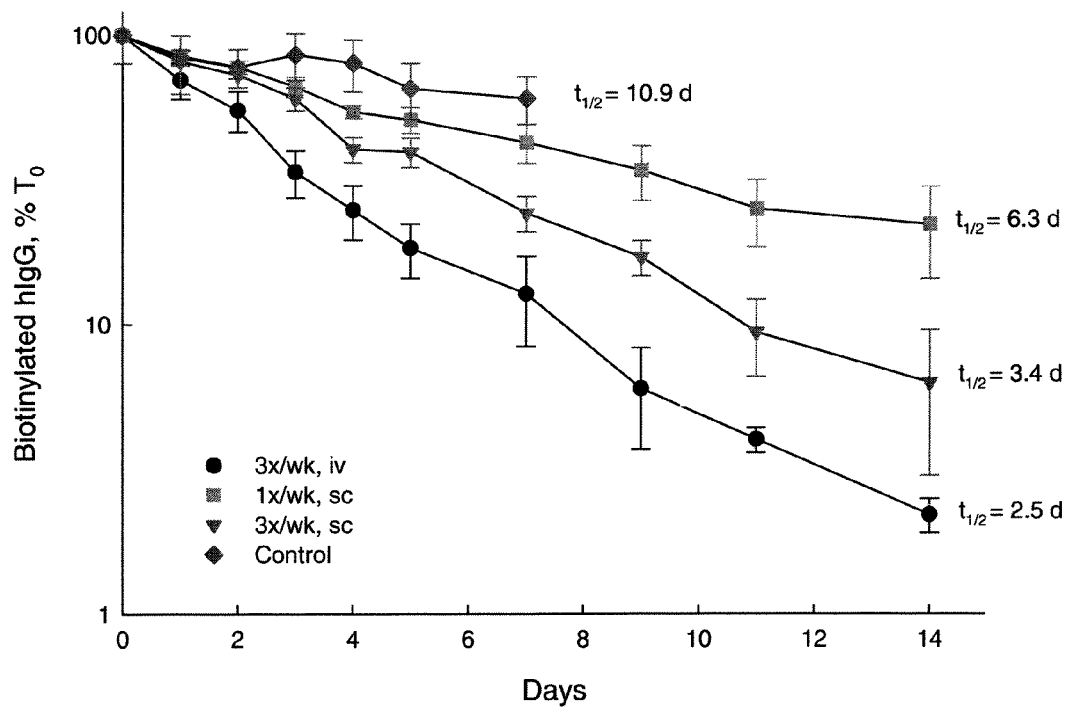
FIG. 20 shows the kinetics of biotinylated human IgG catabolism in cynomolgus monkeys following intravenous injection of 5 mg/kg Peptide No. 283.
Figure 21:
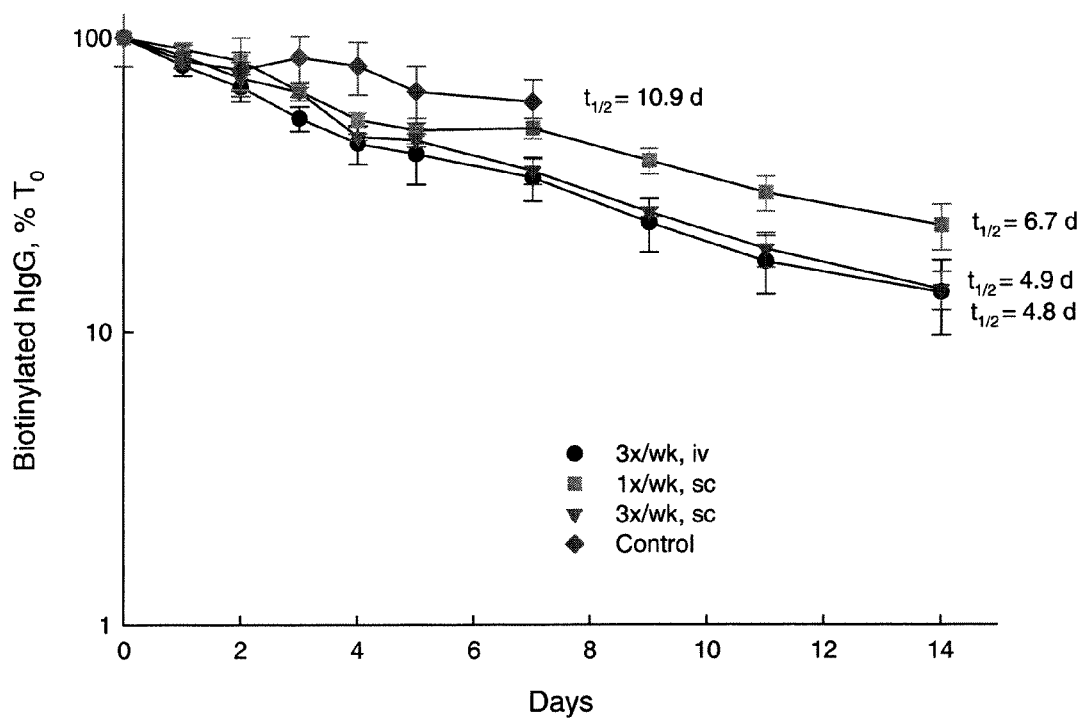
FIG. 21 shows the kinetics of biotinylated human IgG catabolism in cynomolgus monkeys following intravenous injection of 1 mg/kg Peptide No. 283.
Figure 22:
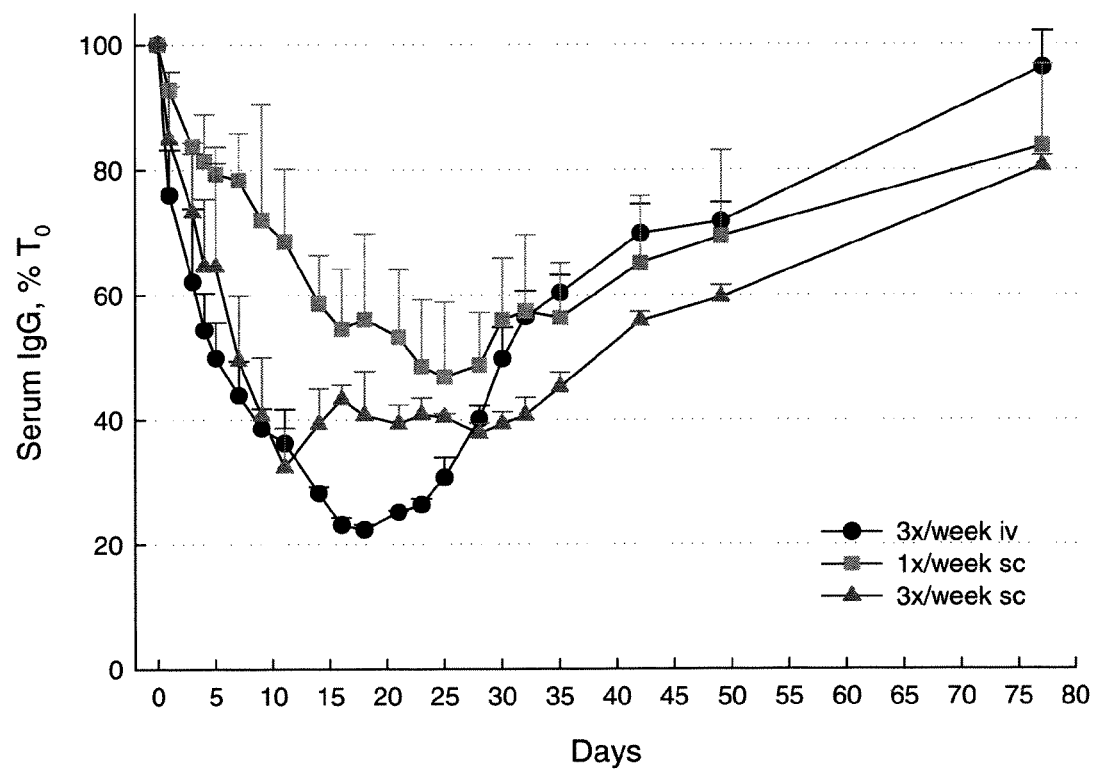
FIG. 22 shows the effect of Peptide No. 283 (5 mg/kg) on the concentration of IgG in cynomolgus monkeys.
Figure 23:
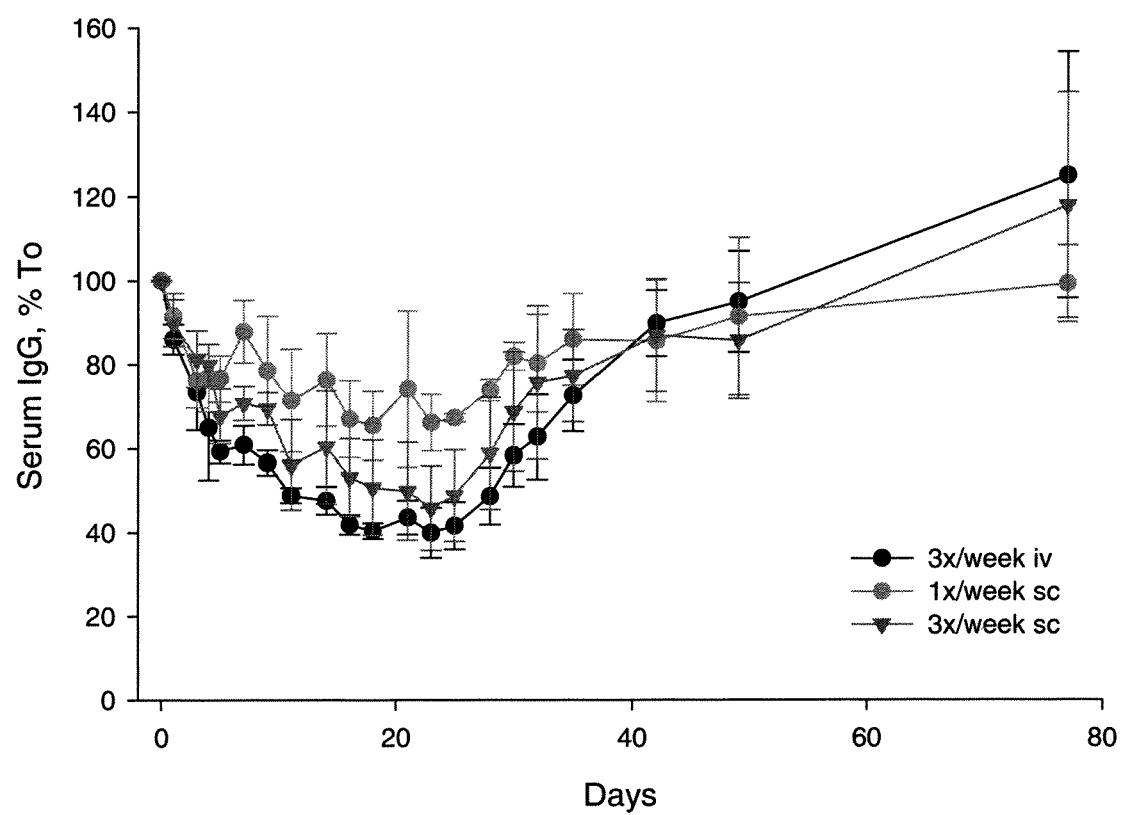
FIG. 23 shows the effect of Peptide No. 283 (1 mg/kg) on the concentration of IgG in cynomolgus monkeys.
Figure 24:
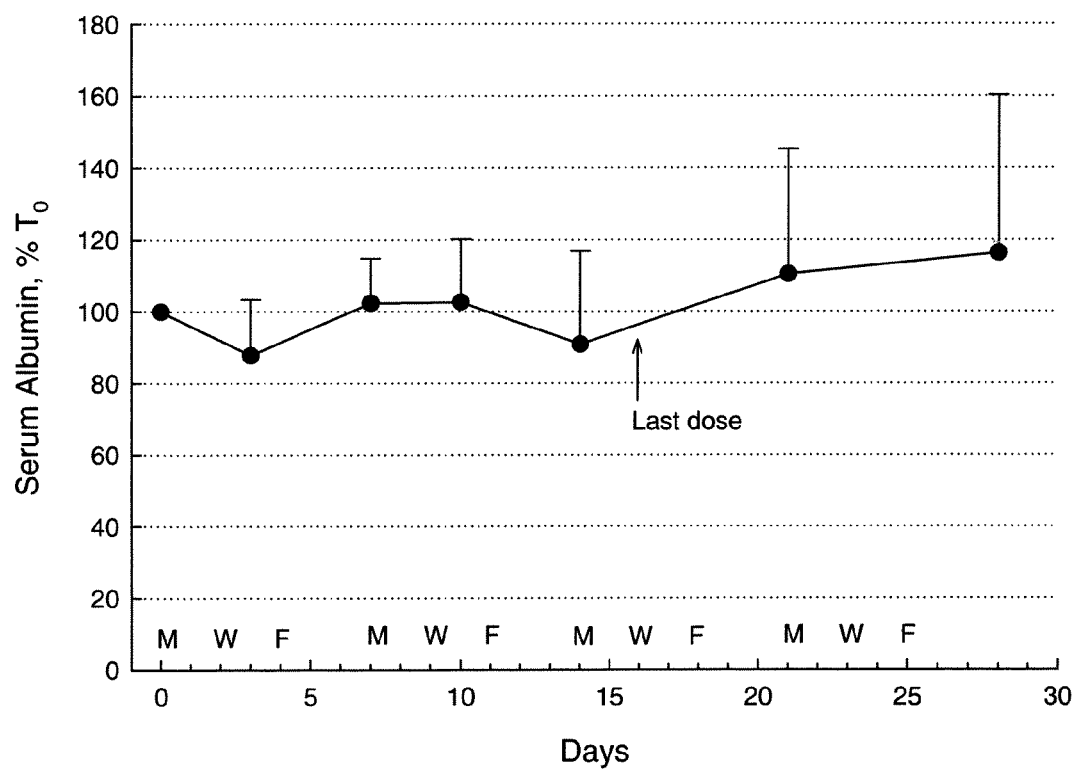
FIG. 24 shows the effect of Peptide No. 283 (5 mg/kg, 3×/week, iv) on the concentration of albumin in cynomolgus monkeys.

Adult TG32B mice were injected intravenously with 500 mg/kg of human IgG (MP Biomedicals, Irvine, Calif.) at t=0 hours (T$_0$). At 24 hours, the mice were injected intravenously with 25 mg/kg of Peptide No. 289. Blood samples were taken at 24, 48, 72, 96, 120 and 168 hours. Serum was prepared and stored at −20° C. until an ELISA was performed. The concentration of human IgG in the serum at each time point were determined as described above in Example 18. (FIG. 19.)

Example 26

Effect of Peptide No. 283 on hIgG Catabolism and Endogenous IgG, IgM, and Albumin Concentrations in Cynomolgus Monkeys Eighteen cynomolgus monkeys were divided into six groups of three animals each and all animals were treated with 5 mg/kg biotinylated human IgG (MP Biomedical) at t=−3 days. Starting at t=0, animals were treated for four weeks with Peptide No. 283 according to the following dosing regimen:

1) 1 mg/kg 3×/week intravenously; 2) 1 mg/kg 1×/week subcutaneously; 3) 1 mg/kg 3×/week subcutaneously; 4) 5 mg/kg 3×/week intravenously; 5) 5 mg/kg 1×/week subcutaneously; 6) 5 mg/kg 3×/week subcutaneously. Note that the last peptide dose for group 4 was at day 16. Serum samples were taken at day −3 d, −15 min, 1 d, 2 d, 3 d, 4 d, 5 d, 7 d, 9 d, 11 d, 14 d, 16 d, 18 d, 21 d, 23 d, 25 d, 28 d, 30 d, 32 d, 35 d, 42 d, 49 d, 77 d. The concentrations of biotinylated human IgG, endogenous IgG, and albumin were determined as described in example 20 and shown in FIGS. 20-24.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supercede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. A peptide capable of binding to human Fc neonatal receptor (FcRn), comprising the sequence:

-Gly-$X_6$—$X_7$—$X_8$—$X_9$—$X_{10}$—$X_{11}$— wherein:
- $X_6$ is selected from the group consisting of a positively charge amino acid, an aromatic amino acid, a positively charged aromatic amino acid and an analog thereof
- $X_7$ is phenylalanine or a phenylalanine analog thereof
- $X_8$ and $X_9$ are each independently selected from the group consisting of glycine, sarcosine, aspartic acid, D-amino acids, α-aminoisobutyric acid, and an analog thereof, or $X_8$, when taken together with $X_9$, forms a dipeptide mimetic;
- $X_{10}$ is an amino acid or an analog thereof, or $X_{10}$, when taken together with $X_9$, forms a dipeptide mimetic;
- $X_{11}$ is a tyrosine or a tyrosine analog thereof; and
wherein the peptide ranges from 7 to 50 amino acids in length, and the peptide binds to human FcRn.

2. The peptide of claim 1, comprising the sequence:

$R_1$-Gly-$X_6$—$X_7$—$X_8$—$X_9$—$X_{10}$—$X_{11}$—$R_2$ wherein:
$R_1$ has the formula $X_1$—$X_2$—$X_3$—$X_4$—
wherein
- $X_1$ is selected from the group consisting of hydrogen, acyl, and amino acid protecting group;
- $X_2$ is absent or is selected from the group consisting of an amino acid, a peptide of 2-15 amino acids in length, and an analog thereof;
- $X_3$ is absent or is an amino acid or analog thereof that is capable of forming a bridge with $X_{10}$, $X_{12}$ or $X_{13}$, wherein the bridge is selected from the group consisting of an amino terminus to carboxy terminus bridge, a side chain to backbone bridge, and a side chain to side chain bridge;
- $X_4$ is absent or is selected from the group consisting of an amino acid, a peptide of 2-15 amino acids in length, and an analog thereof;

$R_2$ has the formula —$X_{12}$—$X_{13}$—$X_{14}$—$X_{15}$
wherein
- $X_{12}$ is absent or is an amino acid or analog thereof;
- $X_{13}$ is absent or is an amino acid or analog thereof;
- $X_{14}$ is absent or is selected from the group consisting of an amino acid, a peptide of 2-15 amino acids in length, and an analog thereof; and
- $X_{15}$ is an amino group or a carboxy protecting group.

3. The peptide of claim 1, comprising the sequence:

Gly-$X_6$-Phe-$X_8$—$X_9$—$X_{10}$-Tyr.

4. The peptide of claim 2, wherein at least one of $X_{10}$, $X_{12}$, and $X_{13}$ is an amino acid or analog thereof that is capable of forming a bridge with $X_3$, wherein the bridge is selected from the group consisting of an amino terminus to carboxy terminus bridge, a side chain to backbone bridge, and a side chain to side chain bridge.

5. The peptide of claim 4, wherein $X_3$ forms a bridge with $X_{10}$, $X_{12}$, or $X_{13}$.

6. The peptide of claim 5, wherein $X_3$ forms a bridge with $X_{13}$.

7. The peptide of claim 5, wherein the bridge is a side chain to side chain bridge.

8. The peptide of claim 7, wherein the side chain to side chain bridge is a disulfide bridge, an ether bridge, a thioether bridge, an alkene bridge, or an amide bridge.

9. The peptide of claim 8, wherein the side chain to side chain bridge is a disulfide bridge between:
- cysteine and cysteine;
- cysteine and homocysteine;
- cysteine and penicillamine;
- homocysteine and homocysteine;
- homocysteine and penicillamine; or
- penicillamine and penicillamine.

10. The peptide of claim 2, comprising at least one cysteine.

11. The peptide of claim 2, comprising at least one cysteine analog selected from the group consisting of:
homocysteine;
D-cysteine; and
penicillamine.

12. The peptide of claim 1 or 2, wherein at least one of $X_8$ and $X_9$ is selected from the group consisting of:
glycine;
D-amino acids;
α-aminoisobutyric acid; and
sarcosine.

13. The peptide of claim 2, wherein $X_2$ is selected from the group consisting of an amino acid, a peptide of 2 or 3 amino acids in length, and an analog thereof.

14. The peptide of claim 1 or 2, wherein $X_6$ is a positively charged aromatic amino acid selected from the group consisting of histidine, 1-methylhistidine, 2-pyridylalanine, 3-pyridylalanine, 4-pyridylalanine, 4-aminophenylalanine, 4-guanylphenylalanine, thiazolylalanine, and an analog thereof.

15. The peptide of claim 14, wherein $X_6$ is selected from the group consisting of histidine, 3-pyridylalanine, 4-pyridylalanine, 4-guanylphenylalanine, and an analog thereof.

16. The peptide of claim 15, wherein $X_6$ is histidine or an analog thereof histidine and analogs thereof.

17. The peptide of claim 1 or 2, wherein $X_{10}$ is selected from the group consisting of neutral and hydrophobic amino acids, and an analog thereof.

18. The peptide of claim 1 or 2, wherein the peptide is a multimer comprising peptide chains that are the same or different.

19. The peptide of claim 18, wherein the peptide is a dimer, a trimer or a tetramer.

20. The peptide of claim 19, wherein the peptide is a dimer.

21. The peptide of claim 20, wherein the dimer is the product of a reaction between individual peptide monomers and a multivalent linker.

22. The peptide of claim 21, wherein the multivalent linker is chosen from thiol, acid, alcohol, and amine linkers.

23. The peptide of claim 1 or 2, wherein the peptide binds specifically to human FcRn and inhibits binding of human FcRn to human IgG.

24. The peptide of claim 23, wherein the affinity of the peptide for human FcRn ranges from 50 fM to 1 mM.

25. The peptide of claim 23, wherein the affinity of the peptide for human FcRn ranges from 500 fM to 100 μM.

26. The peptide of claim 23, wherein the affinity of the peptide for human FcRn ranges from 5 pM to 1 μM.

27. The peptide of claim 1, or 2, wherein the peptide inhibits the binding of human FcRn to human IgG, and has an $IC_{50}$ ranging from 50 fM to 1 mM.

28. A peptide comprising the following structure

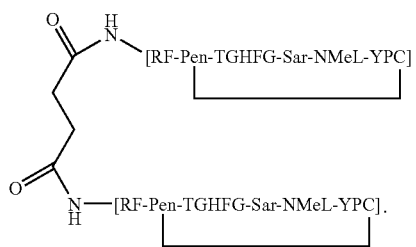

29. A pharmaceutical composition comprising a therapeutically effective amount of the peptide of claim 1 or 2.

30. The composition of claim 29, wherein the therapeutically effective amount of the peptide is capable of decreasing the serum concentration of human IgG as compared to the serum concentration of human IgG before treatment with the peptide.

31. The composition of claim 30, wherein the decrease in the serum concentration of human IgG is at least 5%.

32. The composition of claim 31, wherein the decrease in the serum concentration of human IgG is at least 15%.

33. The composition of claim 32, wherein the decrease in the serum concentration of human IgG is at least 25%.

* * * * *

UNITED STATES PATENT AND TRADEMARK OFFICE
CERTIFICATE OF CORRECTION

| | | |
|---|---|---|
| PATENT NO. | : 8,101,186 B2 | |
| APPLICATION NO. | : 11/676148 | |
| DATED | : January 24, 2012 | |
| INVENTOR(S) | : Adam R. Mezo et al. | |

It is certified that error appears in the above-identified patent and that said Letters Patent is hereby corrected as shown below:

Claim 1, col. 287, line 34, "charge amino acid" should read --charged amino acid--

Claim 1, col. 287, line 36, "thereof" should read --thereof;--

Claim 1, col. 287, line 37, "thereof" should read --thereof,--

Claim 16, col. 289, line 25, "analog thereof histidine and analogs thereof." should read --analog thereof.--

Claim 27, col. 290, line 10, "claim 1, or 2" should read --claim 1 or 2--

Signed and Sealed this
Third Day of April, 2012

David J. Kappos
*Director of the United States Patent and Trademark Office*